(12) United States Patent
Sun et al.

(10) Patent No.: US 9,598,690 B2
(45) Date of Patent: Mar. 21, 2017

(54) METHOD FOR FORMING NANOPARTICLES HAVING PREDETERMINED SHAPES

(75) Inventors: Wei Sun, Boston, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 24 days.

(21) Appl. No.: 14/128,028

(22) PCT Filed: Jun. 29, 2012

(86) PCT No.: PCT/US2012/044846
§ 371 (c)(1),
(2), (4) Date: Mar. 31, 2014

(87) PCT Pub. No.: WO2013/006411
PCT Pub. Date: Jan. 10, 2013

(65) Prior Publication Data
US 2014/0220655 A1    Aug. 7, 2014

Related U.S. Application Data

(60) Provisional application No. 61/504,066, filed on Jul. 1, 2011.

(51) Int. Cl.
| C07H 21/04 | (2006.01) |
| C12N 9/98 | (2006.01) |
| B82B 3/00 | (2006.01) |

(52) U.S. Cl.
CPC .............. *C12N 9/98* (2013.01); *B82B 3/0033* (2013.01)

(58) Field of Classification Search
None
See application file for complete search history.

(56) References Cited

U.S. PATENT DOCUMENTS

| 7,745,594 B2 | 6/2010 | Seelig et al. |
| 7,842,793 B2 | 11/2010 | Rothemund |

(Continued)

FOREIGN PATENT DOCUMENTS

| CN | 1483662 A | 3/2004 |
| EP | 1 388 521 A1 | 2/2004 |
| JP | 2005-255582 A | 9/2005 |

OTHER PUBLICATIONS

Alberts et al "Molecular Biology of the Cell", Garland Publishing, NY, NY, 1994, p. 343.*

(Continued)

*Primary Examiner* — Betty Forman
(74) *Attorney, Agent, or Firm* — Wolf, Greenfield & Sacks, P.C.

(57) ABSTRACT

Articles and methods for forming nanostructures having unique and/or predetermined shapes are provided. The methods and articles may involve the use of nucleic acid containers as structural molds. For instance, a pre-designed nucleic acid container including a cavity may be used to control the shape-specific growth of nanoparticles. Growth of the nanoparticles within the cavities may be confined by the specific shape of the nucleic acid container. In some embodiments, the resulting nucleic acid-nanoparticle structures can be used to control the orientation and numbers of surface ligands on the surface of nanoparticles. The addressability of the surface ligands can be used to form higher ordered assemblies of the structures.

21 Claims, 21 Drawing Sheets

(56) References Cited

U.S. PATENT DOCUMENTS

| | | |
|---|---|---|
| 2005/0112578 A1 | 5/2005 | Matsuura et al. |
| 2010/0069621 A1 | 3/2010 | Maune et al. |
| 2011/0033706 A1* | 2/2011 | Krishnan ............... 428/402 |
| 2012/0244230 A1* | 9/2012 | Mirkin ............... B82Y 5/00 424/649 |
| 2014/0066610 A1 | 3/2014 | Schaus et al. |

OTHER PUBLICATIONS

International Search Report and Written Opinion for PCT/US2012/044846 mailed Nov. 15, 2012.
International Preliminary Report on Patentability for PCT/US2012/044846 mailed Jan. 16, 2014.
Dietz et al., Folding DNA into twisted and curved nanoscale shapes. Science. Aug. 7, 2009;325(5941):725-30. doi: 10.1126/science.1174251.
Douglas et al., Self-assembly of DNA into nanoscale three-dimensional shapes. Nature. May 21, 2009;459(7245):414-8. doi: 10.1038/nature08016.
Goodman et al., Reconfigurable, braced, three-dimensional DNA nanostructures. Nat Nanotechnol. Feb. 2008;3(2):93-6. doi: 10.1038/nnano.2008.3. Epub Feb. 3, 2008.
Preston et al., Formation of gold particles on nanoscale toroidal DNA assembled with bis(ethylenediamine)gold(III). Langmuir. Jun. 15, 2010;26(12):10250-3. doi: 10.1021/la100402j.
Rothemund, Folding DNA to create nanoscale shapes and patterns. Nature. Mar. 16, 2006;440(7082):297-302.
Samson et al., Fabrication of metal nanoparticles using toroidal plasmid DNA as a sacrificial mold. ACS Nano. Feb. 24, 2009;3(2):339-44. doi: 10.1021/nn800758n.
Tan et al., Building plasmonic nanostructures with DNA. Nat Nanotechnol. May 2011;6(5):268-76. doi: 10.1038/nnano.2011.49. Epub Apr. 17, 2011.
Zhao et al., Encapsulation of gold nanoparticles in a DNA origami cage. Angew Chem Int Ed Engl. Feb. 25, 2011;50(9):2041-4. doi: 10.1002/anie.201006818. Epub Jan. 21, 2011.

* cited by examiner

Number control

Distance control

Conformation control

Height control

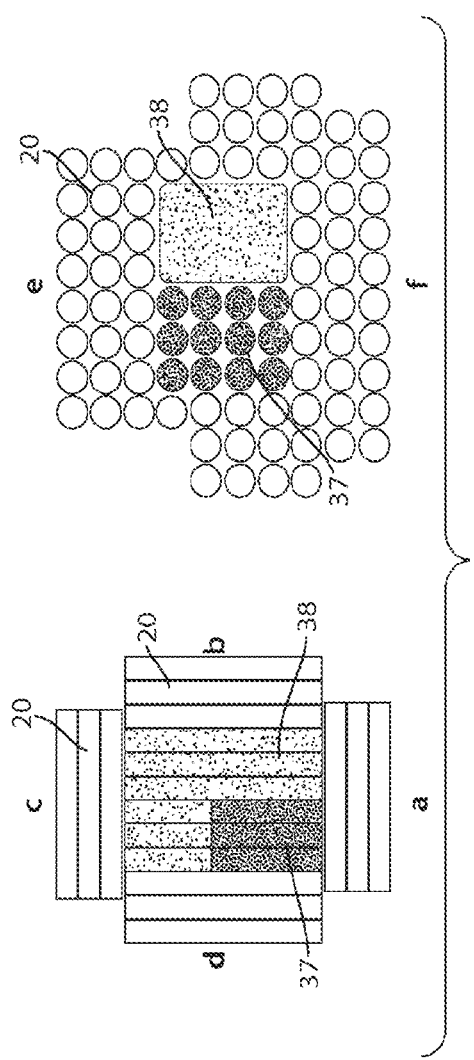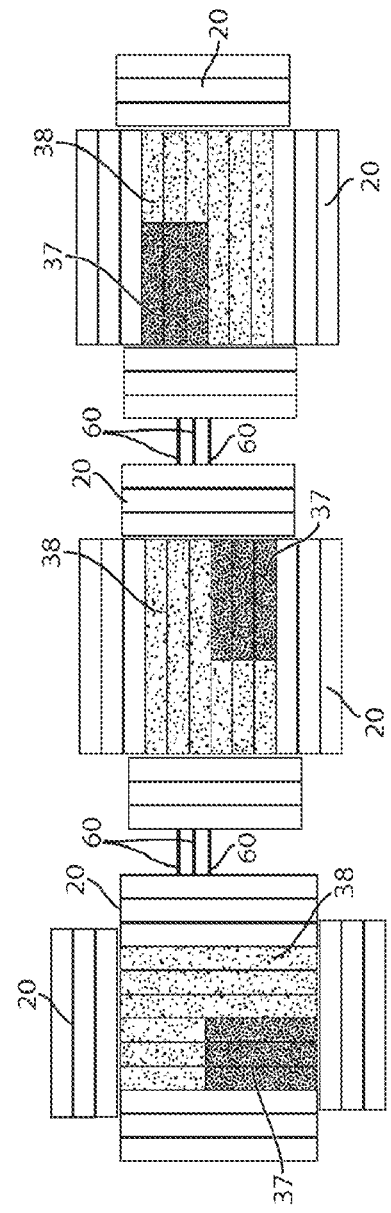

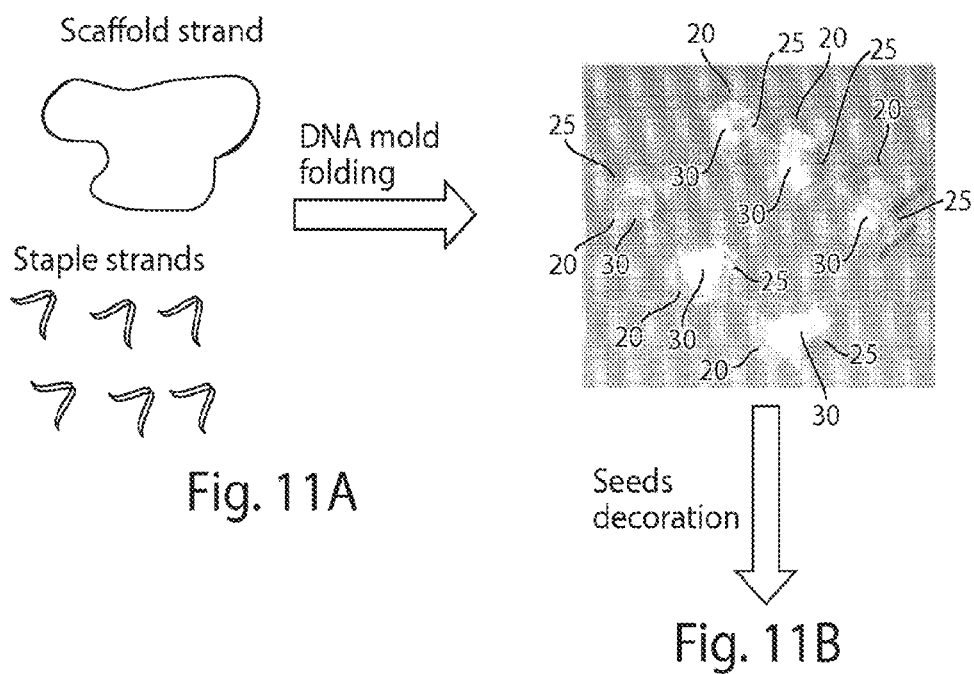
Fig. 11A
Fig. 11B
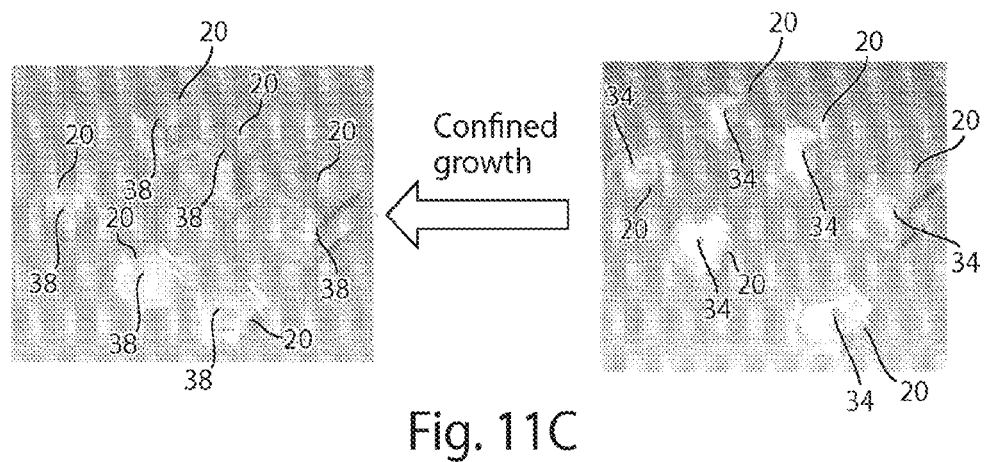
Fig. 11C

METHOD FOR FORMING NANOPARTICLES HAVING PREDETERMINED SHAPES

RELATED APPLICATIONS

This application is a national stage filing under 35 U.S.C. §371 of International Application No. PCT/US2012/044846 filed Jun. 29, 2012, which was published under PCT Article 21(2) in English, and which claims the benefit of U.S. Provisional Application Ser. No. 61/504,066, filed on Jul. 1, 2011, entitled "METHOD FOR FORMING NANOPARTICLES HAVING PREDETERMINED SHAPES", the entire contents of each of which are incorporated by reference herein.

GOVERNMENT SPONSORSHIP

This invention was made with U.S. Government support under N00014-10-1-0827 awarded by the U.S. Office of Naval Research under N66001-11-1-4136 awarded by the U.S. Department of Defense/SPAWAR. The Government has certain rights in the invention.

FIELD OF INVENTION

The present invention relates generally to articles and methods for forming nanostructures, and more specifically to articles and methods for forming nanostructures having unique and/or predetermined shapes.

BACKGROUND

Rational synthesis of monodispersed shape-controllable nanoparticles is the first step towards applications in biodetection that use shape-specific properties of nanoparticles for detection. To direct the growth of nanoparticles (including inorganic nanoparticles such as gold or silver) with specific shapes, templates encoded with the designed geometry are often used. Soft templates, e.g., structures self-assembled from amphiphilic surfactant molecules, have succeeded in creating diverse shapes. However, it is generally difficult to predict the shape of the resultant structure (partially due to the flexible nature of the template), and hence it is challenging to design structures with prescribed shapes using this approach and program the growth of inorganic materials. Hard templates, such as oxides or viruses, have also been utilized to direct the growth of nanowires or nanorods, with better predictability of the resultant structures. However, these approaches may only produce a small number of shapes, which may limit the programmability of shape diversity. Improved methods and articles that could address some or all of these issues, and/or other challenges in the art, would be beneficial in a number of different fields.

SUMMARY OF THE INVENTION

The present invention relates generally to articles and methods for forming nanostructures, and more specifically to articles and methods for forming nanostructures having unique and/or predetermined shapes. The subject matter of the present invention involves, in some cases, interrelated products, alternative solutions to a particular problem, and/or a plurality of different uses of one or more articles, compositions and/or methods.

In one set of embodiments, a series of articles are provided. In one embodiment, an article comprises a nanoparticle positioned inside a nucleic acid container having a predetermined three-dimensional structure, wherein the nanoparticle comprises at least one surface portion having a shape that is complementary to a shape of an inner surface portion of the nucleic acid container.

In another embodiment, an article comprises a nanoparticle comprising at least two opposing surface portions, each of the at least two opposing surface portions having a shape that is complementary to a shape of a surface portion of a nucleic acid nano structure.

In another embodiment, an article comprises an inorganic nanoparticle comprising an isolated nucleic acid strand attached to a surface of the inorganic nanoparticle, wherein the inorganic nanoparticle has a non-spherical shape.

In another embodiment, an article comprises an inorganic nanoparticle coated with a nucleic acid container, wherein the nucleic acid container comprises pores; and a nucleic acid strand attached to a surface of the inorganic nanoparticle, and extending from the surface of the inorganic nanoparticle, through a pore of the nucleic acid container.

In another embodiment, an article comprises an assembly of nucleic acid-coated nanoparticles, wherein the nucleic acid-coated nanoparticles are attached to one another by complementary binding sites.

In another set of embodiments, a series of methods are provided. In one embodiment, a method comprises forming a nanoparticle comprising at least one surface portion having a shape that is complementary to a shape of an inner surface portion of a nucleic acid container having a predetermined three-dimensional structure at the sub-nanometer level.

In another embodiment, a method comprises forming a nanoparticle from a nanoparticle precursor positioned inside a nucleic acid container having a predetermined three-dimensional structure.

In another embodiment, a method comprises providing a nucleic acid container as a template for forming a nanoparticle, wherein the nucleic acid container comprises a plurality of components attached to an inner wall of the nucleic acid container in a predetermined pattern, forming a nanoparticle inside the nucleic acid container, and attaching the plurality of components to the nanoparticle.

In another embodiment, a method comprises attaching an isolated nucleic acid strand to a surface of an inorganic nanoparticle having a non-spherical shape.

In another embodiment, a method comprises providing an inorganic nanoparticle coated with a nucleic acid container, wherein the nucleic acid container comprises pores, introducing a nucleic strand through a pore of the nucleic acid container, and attaching a portion of the nucleic strand to a surface of the inorganic nanoparticle.

In another embodiment, a method comprises forming an assembly of nucleic acid-coated nanoparticles, wherein the nucleic acid-coated nanoparticles are attached to one another by complementary binding sites.

In another embodiment, a method comprises using two nonspherical nanoparticles to detect at least 12 different target molecules.

In another set of embodiments, a series of compositions are provided. In one embodiment, a composition comprises a plurality of nanoparticles, wherein two of the plurality of nanoparticles can be used to detect at least 12 different target molecules.

In another embodiment, a composition comprises a plurality of nanoparticles, wherein at least 90% of the nanoparticles vary in a maximum cross-sectional dimension by less than 0.5 standard deviation of the median maximum cross-sectional dimension of all the nanoparticles in the composition, and wherein each of the plurality of nanoparticles includes at least 6 different sides.

Various configurations of the articles, compositions, and methods described above and herein are provided. For example, in some cases, the nanoparticle precursor comprises an inorganic nanoparticle. In some embodiments, the nanoparticle precursor comprises a metal, a semiconductor, or a monomer of an organic polymer. In one embodiment, the nanoparticle precursor comprises Au, Ag, Cd, Zn, Cu, Pb, Mn, Ni, Mg, Fe, Pd, and/or Pt. The nanoparticle precursor may have a cross-sectional dimension of, for example, less than or equal to 50 nm, less than or equal to 25 nm, less than or equal to 10 nm, less than or equal to 5 nm, less than or equal to 3 nm, less than or equal to 2 nm, less than or equal to 1 nm, or less than or equal to 0.1 nm.

In some embodiments, the nanoparticle comprises at least one surface portion having a shape that is complementary to a shape of an inner surface portion of the nucleic acid container. The nanoparticle may have a shape that is complementary to a shape of the inner surfaces of the nucleic acid container. The nanoparticle may have a three-dimensional shape that includes at least 4, at least 5, at least 6, at least 7, at least 8, at least 9, or at least 10 different sides. The nanoparticle comprises a cross-section in the shape of a rectangle, rod, T, L, branched structure, diamond, star, square, parallelogram, triangle, pentagon, hexagon, ring, or polyhedron. In some embodiments, the nanoparticle has a non-spherical shape or an asymmetric shape. In some cases, the nanoparticle is an inorganic nanoparticle. The nanoparticle may comprises a metal, a semiconductor, or a polymer. In some cases, the nanoparticle is an alloy. In some embodiments, the nanoparticle has at least one cross-sectional dimension that is less than or equal to 1 micron, less than or equal to 500 nm, less than or equal to 250 nm, less than or equal to 100 nm, less than or equal to 75 nm, less than or equal to 50 nm, less than or equal to 40 nm, less than or equal to 30 nm, less than or equal to 20 nm, less than or equal to 10 nm, or less than or equal to 1 nm. In certain embodiments, the nanoparticle has at least one cross-sectional dimension that is greater than or equal to 1 nm, greater than or equal to 5 nm, greater than or equal to 10 nm, greater than or equal to 50 nm, or greater than or equal to 100 nm. The nanoparticle may have an aspect ratio of at least 2:1, at least 3:1, at least 5:1, at least 10:1, or at least 20:1. The nanoparticle may be encapsulated by a nucleic acid nanostructure. In some embodiments, the nanoparticle comprises an isolated binding site attached to a surface of the nanoparticle. In some cases, the nanoparticle comprises at least 2, at least 4, at least 6, at least 8, at least 10, at least 12, at least 14, at least 16, at least 18, or at least 20 different isolated binding sites attached to a surface of the nanoparticle. The nanoparticle may comprises an isolated nucleic acid strand attached to a surface of the nanoparticle. The isolated binding sites may be positioned at least 2 nm, at least 5 nm, at least 10 nm, at least 15 nm, at least 20 nm, or at least 30 nm apart from one another. In some embodiments, the nucleic acid strand is a DNA strand or DNA analog, or a RNA strand or RNA analog.

In some embodiments, the nanoparticle may have a cross-sectional shape that includes different numbers of vertexes. A cross-sectional shape of the nanoparticle may have, for example, at least 3, at least 4, at least 5, at least 6, at least 7, at least 8, at least 9, or at least 10 vertexes. In some embodiments, at least 1, at least 2, at least 3, at least 4, at least 5, at least 6, at least 7, at least 8, at least 9, or at least 10 vertexes of the cross-sectional shape of the nanoparticle are rounded. In other embodiments, at least 1, at least 2, at least 3, at least 4, at least 5, at least 6, at least 7, at least 8, at least 9, or at least 10 vertexes of the cross-sectional shape of the nanoparticle are substantially sharp. Combinations of rounded and sharp vertexes are also possible.

In some embodiments, the nucleic acid container comprises a cavity having a volume, and at least 60%, or at least 80% of the volume is filled with the nanoparticle. In some cases, the nucleic acid container comprises a cavity having a volume, and substantially all of the volume is filled with the nanoparticle. In some embodiments, the nucleic acid container comprises a cavity in the shape of a polyhedron, has a non-spherical shape, or has an asymmetric shape. In some cases, the nucleic acid container comprises at least one open side, or at least two open sides. In certain cases, the nucleic acid container is substantially closed. In some embodiments, the nucleic acid container comprises at least one lid that can be open or closed.

The nucleic acid container may comprise a cavity, and a cross-sectional dimension of the cavity may be less than or equal to 1 micron, less than or equal to 500 nm, less than or equal to 250 nm, less than or equal to 100 nm, less than or equal to 75 nm, less than or equal to 50 nm, less than or equal to 40 nm, less than or equal to 30 nm, less than or equal to 20 nm, less than or equal to 10 nm, or less than or equal to 1 nm. In some embodiments, the nucleic acid container comprises a cavity, and a cross-sectional dimension of the cavity is greater than or equal to 1 nm, greater than or equal to 5 nm, greater than or equal to 10 nm, greater than or equal to 20 nm, greater than or equal to 30 nm, greater than or equal to 40 nm, greater than or equal to 50 nm, greater than or equal to 100 nm, greater than or equal to 500 nm, or greater than or equal to 1 micron. In some embodiments, the nucleic acid container comprises walls that surround a cavity, and the average thickness of the walls is less than or equal to 1 micron, less than or equal to 500 nm, less than or equal to 250 nm, less than or equal to 100 nm, less than or equal to 75 nm, less than or equal to 50 nm, less than or equal to 40 nm, less than or equal to 30 nm, less than or equal to 20 nm, less than or equal to 10 nm, or less than or equal to 1 nm. In some cases, the nucleic acid container comprises walls that surround a cavity, and wherein the average thickness of the walls is greater than or equal to 1 nm, greater than or equal to 10 nm, greater than or equal to 25 nm, greater than or equal to 50 nm, greater than or equal to 100 nm, greater than or equal to 500 nm, or greater than or equal to 1 micron.

In some cases, the nucleic acid container comprises more than one layer. The nucleic acid container may be formed of a nucleic acid having a molecular weight of at least 640 kDa. In some embodiments, the nucleic acid container is formed of a nucleic acid having a length of at least 1,000 bases. In some embodiments, a nucleic acid container comprises an inorganic nanostructure.

In some embodiments, an assembly is formed by assembling nucleic acid containers, each of the nucleic acid containers having a nanoparticle precursor positioned therein, and then synthesizing the nanoparticle from the nanoparticle precursor inside the nucleic acid container to form the nucleic acid-coated nanoparticles. The assembly may be formed by synthesizing a plurality of nucleic acid-coated nanoparticles, each of the nucleic-acid coated nanoparticles formed by growing a nanoparticle from a nanoparticle precursor positioned inside a nucleic acid container, and then assembling the nucleic acid-coated nanoparticles. The nucleic acid-coated nanoparticles may be attached to one another by binding sites that are attached to a nucleic acid portion of the nucleic acid-coated nanoparticles. In some embodiments, the nucleic acid-coated nanoparticles are attached to one another by binding sites that are attached to a nanoparticle portion of the nucleic acid-coated nanoparticles. In some cases, the nucleic acid-coated nanoparticles are attached to one another using a thermal process, a photophysical process, and/or a binding process.

In some embodiments, a method involves removing a portion of the nucleic acid from the nucleic acid-coated nanoparticles. In some cases, a method involves substantially removing the nucleic acid coating from the nucleic acid-coated nanoparticles. In some embodiments, a method involves passivating a surface of the nanoparticle prior to, during, or after the removal step. The nanoparticles may remain attached to one another in the assembly after the removal step.

In embodiments involving assemblies, the assembly may be an electronic circuit. The assembly may be in the form of a two-dimensional array, or a three-dimensional array. The assembly may have at least one length and/or at least one cross-sectional dimension that is less than or equal to 1 mm, less than or equal to 100 microns, less than or equal to 50 microns, less than or equal to 10 microns, less than or equal to 1 micron, less than or equal to 500 nm, less than or equal to 100 nm, less than or equal to 50 nm, less than or equal to 10 nm, or less than or equal to 1 nm. The assembly may have at least one length and/or at least one cross-sectional dimension that is greater than or equal to 1 nm, greater than or equal to 10 nm, greater than or equal to 100 nm, greater than or equal to 1 micron, greater than or equal to 10 microns, greater than or equal to 50 microns, greater than or equal to 100 microns, or greater than or equal to 1 mm.

In some cases, the nanoparticle comprises a marker attached to a surface of the nanoparticle. In some embodiments, the marker is isolated on the surface of the nanoparticle. The marker may comprises a nucleic acid strand, a fluorophore, a nanoparticle, an antibody, a peptide, or a reporter molecule. In some embodiments, the marker is a surface-enhanced Raman scattering reporter molecule. In some cases, the marker is a luminescent probe. In certain embodiments, each marker is adjacent a binding site attached to the surface of the nanoparticle. In some embodiments, the nanoparticle comprises a plurality of marker and binding site pairs, wherein each of the markers are different from one another, and each of the binding sites are different from one another. An article, a composition, or a method may comprise at least 4, at least 5, at least 6, at least 7, at least 8, at least 9, at least 10, at least 12, at least 15, or at least 20 different markers positioned on the surface of the nanoparticle. In some cases, each of the components or markers are isolated from one another and are positioned at predetermined distances from one another. A method may involve attaching a predetermined number of components or markers to the nanoparticle.

In some embodiments, an article to detect a biomolecule, e.g., the multiplexed detection of biomolecules. Detection may comprise introducing a target molecule to a plurality of nanoparticles, and allowing the target molecule to bind to surfaces of at least two different nanoparticles. Binding may enhance a Raman signal from two reporter molecules associated with the surfaces of the nanoparticles. A method may involve using two nanoparticles to detect at least 5, at least 10, at least 20, at least 30, at least 40, at least 50, at least 70, or at least 100 different target molecules in parallel.

In some embodiments, each of the nucleic acid-coated nanoparticles is in the form of a nanoparticle positioned inside a nucleic acid container. A method may involve forming, in parallel, at least 10, at least 15, at least 20, at least 30, at least 50, or at least 100 inorganic nanoparticles each having different shapes.

A method may comprise synthesizing the nanoparticle from a seed-mediated growth process. In some cases, the nanoparticle is synthesized in the absence of a surfactant, or in the absence of an oxide template. The nucleic acid container may be designed to include a cavity having a pre-designed three-dimensional structure, and the shape of the nanoparticle is formed, at least in part, by molding against the cavity.

In some embodiments, a method involves controlling ion diffusion kinetics to control the growth kinetics and/or composition of the nanoparticle. A method may comprise controlling the distribution of components in an nanoparticle alloy.

In some cases, the inorganic nanoparticle is hollow and comprises a cavity. The inorganic nanoparticle may be used as a template to fabricate a secondary nanostructure in the cavity of the nanoparticle. The nanoparticle or nanostructure may have a complex arbitrary shape.

The combination of programmable nucleic acid containers with nanoparticle synthesis enables the programmability of arbitrary shaped materials by using the containers as molds. Target structural information may be encoded into the cavity design of specifically shaped nucleic acid containers. In some embodiments, growth of certain materials (e.g., inorganic materials) within the cavities may start using small nanoparticle precursors (e.g., nanocrystals) for the nucleation of inorganic materials, on the interior surface of nucleic acid cavity, and is stopped or significantly slowed down when the growing lattices encounter the nucleic acid sidewalls. These approaches may enable a wide variety of applications that take advantage of the nucleic acid-programmed synthesis of inorganic materials, such as in multiplexed surface enhanced Raman scattering (SERS) detection, in DNA-directed self-assembly of electronic circuits, in surface-specific catalyst and in structural constrain for electrode materials in lithium-based fuel cells. Notably, the syntheses described herein can be executed not only ex-vivo (e.g., in test tubes), but also under in-vitro/in-vivo conditions, such as in bacteria and cells.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 4A-4F show control of surface addressability of nanostructures according to one set of embodiments;

FIGS. 11A-11C show a method involving the use of a nucleic acid container as a mold to form nanoparticles having different shapes according to one set of embodiments;

DETAILED DESCRIPTION

Articles and methods for forming nanostructures having unique and/or predetermined shapes are provided. In some embodiments, the methods and articles involve the use of nucleic acid containers as structural molds. For instance, a pre-designed nucleic acid container including a cavity may be used to control the shape-specific growth of nanoparticles. Growth of the nanoparticles within the cavities may be confined by the specific shape of the nucleic acid container. Using such a method, nanoparticles having complex and predetermined shapes and sizes can be formed. The resulting nanoparticle that is coated with a nucleic-acid container may be used as is, or the nucleic acid coating may be removed partially or completely if desired.

Additionally, the methods described herein allow the material composition of the grown nanoparticles to be controlled by using different nanoparticle precursors and/or by controlling the thickness of the walls of the nucleic acid containers. In some embodiments, controlling such parameters can allow the formation of nanoparticle alloys having predetermined and controlled ratios of material components. In some embodiments, the resulting nucleic acid-nanoparticle structures can be used to control the orientation, numbers, types, and positioning of components such as binding sites, markers, and surface ligands on the surface of the nanoparticles or the surface of the nucleic acid containers. Advantageously, nanoparticles having a predetermined number and orientation of unique components attached to the nanoparticle or nucleic acid container surface may allow addressability of the structures for applications such as multiplexed detection of target molecules. Moreover, the addressability of the structures can be used to form higher ordered assemblies of the structures in some embodiments.

The articles and methods provided herein have applications in a number of different fields, including the areas of bio-sensing, electronics, environment sciences, and energy. Other advantages of the articles and methods described herein are provided in more detail below.

Figure 1A:
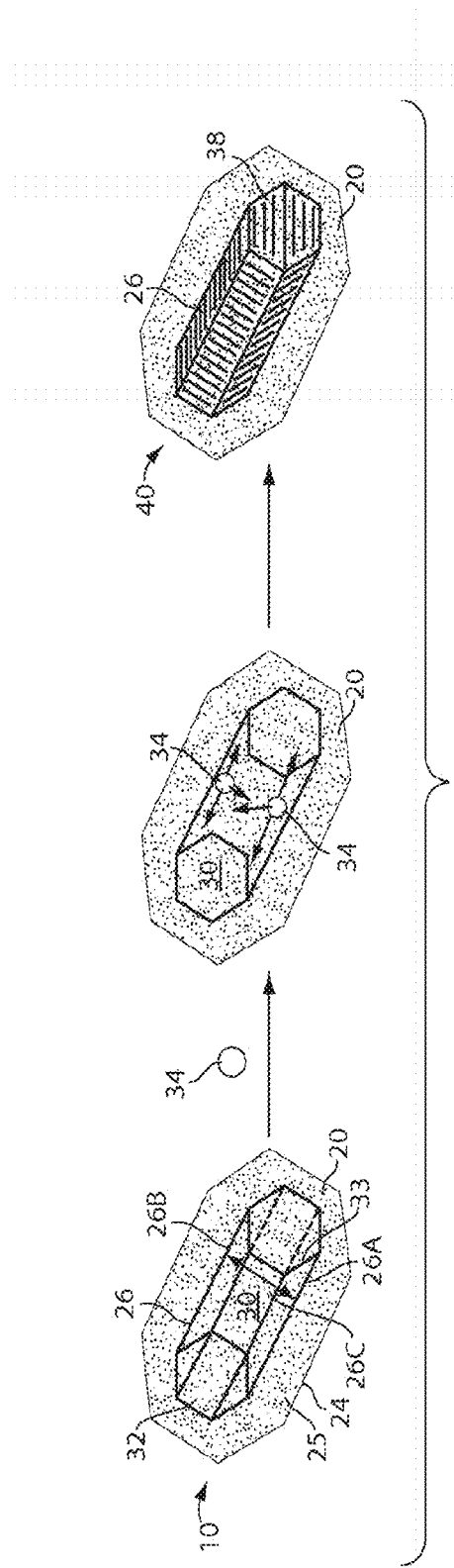
FIG. 1A shows a method involving the use of a nucleic acid container as a mold to form a nanoparticle according to one set of embodiments.

An example of a method for forming nanoparticles having unique and/or predetermined shapes in shown in FIG. 1A. As shown illustratively in FIG. 1A, scheme 10 involves the use of a nucleic acid container 20 as a mold for the templated synthesis of a nanoparticle. Nucleic acid container 20 includes an outer surface 24, an inner surface 26, and a wall 25 formed between the outer and inner surfaces. The nucleic acid container also includes a cavity 30 enclosed by the inner surface portions of the nucleic acid container. As shown illustratively in FIG. 1A, the nucleic acid container may also include an end 32 and an end 33, which may be open in some embodiments, or closed in other embodiments. An opening into the cavity may allow one or more nanoparticle precursors 34 to be inserted into the cavity. Alternatively, one or more nanoparticle precursors can be present inside a cavity that is completely closed, e.g., by attaching the one or more nanoparticle precursors to the nucleic acid used to form the container during formation of the container itself. Once inserted into the cavity, the one or more nanoparticle precursors may be associated with the nucleic acid container by, for example, being covalently attached, physisorbed, chemisorbed, or attached to the nucleic acid container through ionic interactions, hydrophobic and/or hydrophilic interactions, electrostatic interactions, van der Waals interactions, or combinations thereof. In other embodiments, one or more nanoparticle precursors may be floating inside the cavity.

The walls of the nucleic acid container may also allow nanoparticle precursor solutions to flow through it in order to facilitate the formation of a nanoparticle. Generally, the walls of the nucleic acid container are porous and may allow penetration and/or transport of certain molecules and components into or out of the container, but may prevent penetration and/or transport of other molecules and components into or out of the container. The ability of certain molecules to penetrate and/or be transported into and/or across a wall of the container may depend on, for example, the packing density of the nucleic acids forming the wall, the thickness of the walls, and the chemical and physical properties of the wall, as described in more detail below. Accordingly, a nucleic acid container need not be open, and in some embodiments may be substantially closed, while still allowing certain nanoparticle precursors to enter into the cavity via the pores and facilitating the formation of a nanoparticle in the container.

Figure 1B:
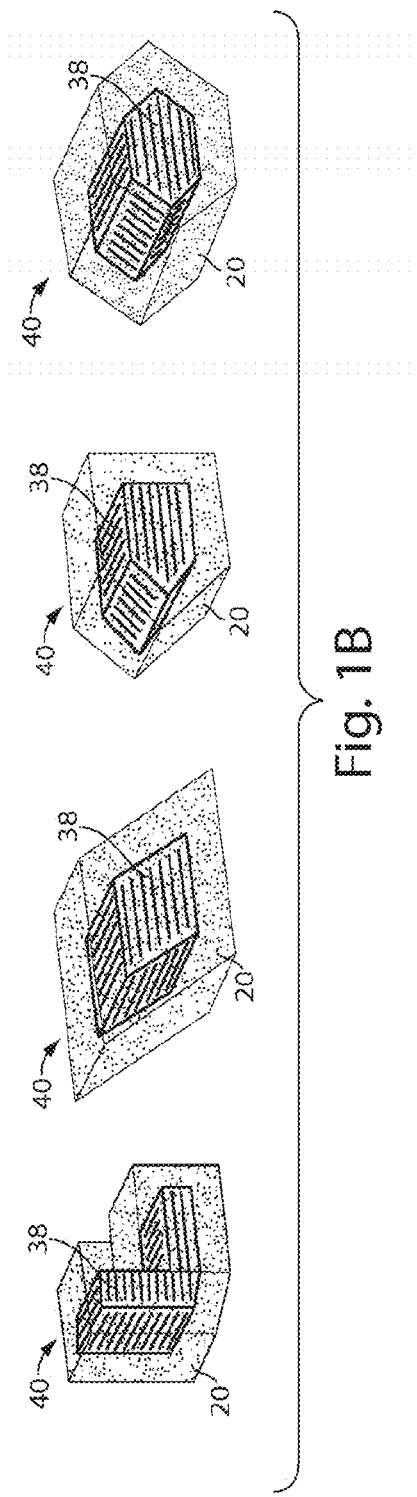
FIG. 1B shows different shapes of nanoparticles that can be formed using different shapes of nucleic acid containers according to one set of embodiments.

Once one or more nanoparticle precursor are positioned in the cavity, they can facilitate the formation of a nanoparticle 38 that may fill all portions of the cavity. The shape of nanoparticle 38 may be determined, at least in part, by the shape of the cavity of the nucleic acid container. The shape of the cavity of the nucleic acid container, in turn, may be varied by controlling the configuration and orientation of the nucleic acid strands that form the inner surfaces of the container, as described in more detail below. FIG. 1B shows examples of nucleic acid containers having cavities with different shapes that can be used to form nanoparticles 38 having different shapes. Advantageously, a wide variety of unique and/or predetermined shapes of nanoparticles can be formed using the methods described herein.

In certain embodiments, growth of a nanoparticle in a cavity of the container continues until the nanoparticle encounters an inner surface or wall of the container. Chemical and/or physical interactions between the growing nanoparticle and the inner surface of the container may stop or significantly slow down the growth of nanoparticle. In certain embodiments involving nucleic acid containers that are substantially closed, the entire size and/or shape of nanoparticle 38 may be controlled by the size and/or shape of the cavity of the container, as described in more detail below. In other embodiments, the growth of all or portions of a nanoparticle stops before it is in contact with an inner surface portion of the container.

Growing the nanoparticle inside a cavity of a nucleic acid container generally involves more than simply the addition of surface ligands to the surface of the nanoparticle precursor. For example, in some embodiments in which a nanoparticle precursor is used to grow a nanoparticle, the nanoparticle precursor may have a shape that is substantially different from the shape of the resulting nanoparticle that is grown from the nanoparticle precursor. In some instances, the resulting nanoparticle has a more complex shape than that of the nanoparticle precursor. In addition, as described in more detail below, the volume of the resulting nanoparticle may be substantially different (e.g., substantially greater) than that of the nanoparticle precursor.

The combined nucleic acid container 20 and nanoparticle 38 shown in FIG. 1A may form a composite nanostructure 40 that may be used in a variety of different applications, as described in more detail below.

Although FIG. 1A shows the introduction of nanoparticle precursor 34 into the cavity of the nucleic acid container after the nucleic acid container has been formed, in other embodiments, a nanoparticle precursor can be associated with a nucleic acid container while the container is being formed. For example, design of the nucleic acid container may involve including a binding site on a portion of a nucleic acid that will form an inner surface portion of the container. During annealing of the nucleic acids to form the shape of the container, a nanoparticle precursor having a binding site complementary to the binding site attached to nucleic acid can be introduced to allow binding between the interior surface of the container and the nanoparticle precursor.

As shown illustratively in FIG. 1A, nanoparticle 38 may be formed by a seed-mediated growth process involving the use of nanoparticle precursor 34. That is, the nanoparticle precursor, which may itself be in the form of a nanoparticle, may be used as a seed to grow a larger nanoparticle in the presence of other precursors (e.g., nanoparticle precursor solutions) that may determine the material composition of nanoparticle 38. Any suitable combinations of nanoparticle precursors and nanoparticle precursor solutions can be used. For example, to form a nanoparticle formed of gold, a gold nanoparticle precursor and precursor solutions of $HAuCl_4$ and ascorbic acid may be used. To form a nanoparticle of silver, a gold nanoparticle and precursor solutions of $AgNO_3$ and ascorbic acid may be used. Accordingly, the material composition of the resulting nanoparticle can be controlled by varying the types of precursors used. Examples of additional types of nanoparticle precursors are provided in more detail below.

In some embodiments, nanoparticles can be formed by a method other than a seed-mediated process. For example, one or more nanoparticle precursors may fill all or portions of the cavity of a nucleic acid container and optionally an external force such as heat, light, pressure, electrical potential, magnetic force, and/or electromagnetic force can be applied to facilitate the growth or formation of the nanoparticle. In some cases, a chemical component can be added to facilitate the growth of the nanoparticle. In one particular embodiment, a nanoparticle precursor such as a monomer (e.g., a monomer of an organic polymer, such as a synthetic organic polymer), and optionally one or more catalysts to trigger the growth of the monomer, can be introduced in solution form into the cavity of a nucleic acid container. Polymerization of the monomers can take place in the cavity of the nucleic acid container by, for example, applying heat, light or other stimulus to allow formation of a polymeric nanoparticle. Monomers such as nucleotides and amino acids can be used.

The resulting nanoparticle may have a physical state that is different from that of the nanoparticle precursor. For example, the formation of a nanoparticle may involve applying a stimulus to cause transformation of a nanoparticle precursor into a different form so as to form the resulting nanoparticle. For example, a nanoparticle precursor may be in the form of a liquid, and the resulting nanoparticle may be in the form of a solid or solid-like substance (e.g., a gel). In other embodiments, the resulting nanoparticle has the same physical state as that of the nanoparticle precursor. For example, both the nanoparticle and the nanoparticle precursor may be in the form of solids.

As described herein, in some embodiments the formation of a nanoparticle in a cavity of a nucleic acid container is stopped or significantly slowed down by confinement of the nanoparticle in the container. For example, the formation of the nanoparticle may be stopped by chemical interaction between a surface of the nanoparticle and an inner surface of the nucleic acid container. It should be appreciated, however, that in some embodiments, synthesis of the nanoparticle can be stopped or significantly slowed down before the nanoparticle fills the entire volume of the nucleic acid container. For example, where an external force such as those described herein are used to facilitate formation of the nanoparticle, application of an external force may be stopped prior to the nanoparticle filling the entire volume of a nucleic acid container.

Accordingly, in some embodiments, the nucleic acid container comprises a cavity having a volume, and only a portion of the volume is filled with the nanoparticle. For example, less than 100%, less than 80%, less than 60%, less than 40%, less than 20%, or less that 10% of the volume of a cavity may be filled with the nanoparticle. In certain embodiments, at least 5%, at least 10%, at least 15%, at least 20%, at least 40%, at least 60%, or at least 80%, at least 90%, at least 95%, or at least 99% of the volume of cavity is filled with a nanoparticle. Combinations of the above-noted ranges are also possible (e.g., less than 100% but at least of 20% of the volume of the container may be filled with the nanoparticle). In yet other embodiments, substantially all of the volume of a nucleic acid container is filled with a nanoparticle.

Methods described herein may be used to form a population of nanoparticles having relatively high uniformity in size, shape, and/or mass. For example, in some embodiments, a composition includes nanoparticles wherein at least 60%, at least 80%, at least 90%, at least 95%, at least 98%, at least 99%, or 100% of the nanoparticles vary in dimension (e.g., a cross-sectional dimension, a maximum cross-sectional dimension, a width, a height, or a length) or mass by less than three standard deviations, less than two standard deviations, less than one standard deviation, less than 0.5 standard deviation, or less than 0.2 standard deviation of the median or average dimension or mass of all the nanoparticles in the composition. In certain embodiments, a composition may include nanoparticles that have a distribution of dimensions (e.g., cross-sectional dimension, width, height or length) or mass such that no more than 20%, no more 15%, no more than 10%, no more than 5%, no more than 3%, no more than 2%, or no more than 1% of the nanoparticles have a dimension or mass that differs by more than 20%, by more than 15%, by more than 10%, by more than 5%, by more than 3%, by more than 2%, or by more than 1% of the median or average value of the corresponding dimension or mass of all the nanoparticles in the composition.

The methods described herein may also be used to control and tune the material composition of the nanoparticle at different regions of the nanoparticle. For example, in a gold/silver nanoparticle alloy formed by the methods described herein, the ratio of gold to silver may be 8:1 (wt:wt) at a first region and a ratio of 1:8 (wt:wt) at a second region. Generally, an alloy including a first and second component may have a ratio of the first to the second component of, for example, between 1:20 and 20:1 (wt:wt). In some embodiments, the ratio of the first to the second component of an nanoparticle alloy may be at least 1:20, at least 1:15, at least 1:10, at least 1:8, at least 1:6, at least 1:4, at least 1:2, at least 1:1, at least 2:1, at least 4:1, at least 6:1, at least 8:1, at least 10:1, at least 15:1, or at least 20:1 at a first region of the nanoparticle, and a ratio of the first to the second component of at least 1:20, at least 1:15, at least 1:10, at least 1:8, at least 1:6, at least 1:4, at least 1:2, at least 1:1, at least 2:1, at least 4:1, at least 6:1, at least 8:1, at least 10:1, at least 15:1, or at least 20:1 at a second region, wherein the ratios are different between the first and second regions. Alloys including a third component may also be possible. In some cases, the ratio between the first to third components, or the second to third components, have one of the above-noted ratios.

Methods described herein may also be used to form nanoparticles having relatively high uniformity in material composition. For example, in some embodiments, a composition includes nanoparticles wherein at least 60%, at least 80%, at least 90%, at least 95%, at least 98%, at least 99%, or 100% of the nanoparticles vary in material composition by less than three standard deviations, less than two standard deviations, less than one standard deviation, less than 0.5 standard deviation or less than 0.2 standard deviation of the median or average material composition of all the nanoparticles in the composition. In some embodiments, such compositions having a relatively high uniformity in material composition include nanoparticle alloys having the above-noted ratios between first and second components.

In other embodiments in which a mixture of different nanoparticles having different shapes is desired, a method may include using different nucleic acid containers to form a variety of different nanoparticles in parallel. For example, in some instances between 2 and 1,000 nanoparticles (e.g., between 2 and 500, between 2 and 200, or between 2 and 100 nanoparticles), each having different predetermined shapes, may be formed in parallel. In some embodiments, a method may include using different nucleic acid containers to form, in parallel, at least 10, at least 15, at least 20, at least 30, at least 50, or at least 100 nanoparticles (e.g., inorganic nanoparticles) each having different shapes. A composition may include such numbers of differently shaped nanoparticles and/or nanostructures.

In some embodiments, the methods described herein can be used to form nanoparticles in the absence of certain materials such as surfactants (e.g., cetyltrimethylammonium bromide). As such, a variety of different materials, including materials that are not compatible with surfactants, may be used in the methods described herein. In certain embodiments, the nanoparticle may be synthesized in the absence of an oxide template.

In certain embodiments, the methods described herein can be performed ex-vivo (e.g., in test tubes). In other embodiments, the methods can be performed under in-vitro or in-vivo conditions, such as in bacteria and cells.

Other features of nucleic acid containers, nanoparticles, and combinations thereof are described in more detail below.

As described herein, nucleic acid containers can be used as a template to form nanoparticles within one or more cavities of the container. The nucleic acid container may have a predetermined three-dimensional shape or structure (e.g., a non-random three-dimensional shape or structure).

The nucleic acid containers described herein can be formed using any suitable method. In some embodiments, a nucleic acid container may be constructed using a non-random process, such as process that involves deliberate folding and/or bending of nucleic acid strands to form the shape of the nucleic acid container. In some embodiments, a DNA "origami" method may be used. Using such a method, 3-dimensional (3D) nucleic acid containers with arbitrary user specified shapes can be formed. In some embodiments, the nucleic acid container is formed primarily of a single strand of nucleic acid, with optional multiple shorter strands that may help define the resulting shape of the container. For example, in some embodiments involving the use of a DNA "origami" method, a long "scaffold" DNA strand "rasterizes" a target structure shape, while many short "staple" strands hybridize to the scaffold and hold it in the target shape. Other methods of constructing nucleic acid containers using similar polymers are also possible. For example, in the field known as structural DNA nanotechnology (e.g., DNA origami and designs involving single-stranded tiles), self-assembled nucleic acids (particularly, DNA) have been used to construct diverse synthetic molecular structures and devices such as ribbons, tubes, lattices, and arbitrary 2D and 3D shapes. Moreover, channels can be introduced into hollow DNA nanostructures, e.g., DNA nanotubes and 3D barrels. These synthetic molecular structures and hollow DNA nanostructures may include cavities for nanoparticle growth according to the present invention and as described herein.

Nucleic acid containers can be designed with or without software packages such as caDNAno and other software known in the art. In some embodiments, the scaffold strand may be naturally occurring such as that of the M13 virus. In other embodiments, the scaffold strand may be non-naturally occurring. In either instance, the sequence of the scaffold strand should be known. Software packages such as NUPACK can also be used to design dynamic sequence components. Those of ordinary skill in the art are familiar with these methods as evidenced by the disclosures in U.S. Pat. Nos. 7,745,594 and 7,842,793; U.S. Patent Publication No. 2010/00696621; and Goodman et al. Nature Nanotechnology, doi 10.1038/nnano.2008.3, the entire contents of which including the methods for generating nucleic acid based structures are incorporated by reference herein.

As described herein, in some embodiments, a nucleic acid container is formed primarily of a single strand of nucleic acid (i.e., a "scaffold"). For example, in some embodiments, a single strand of nucleic acid used to form the nucleic acid container makes up at least 50%, at least 60%, at least 70%, at least 80%, at least 90%, or at least 95% of the total molecular weight of the overall nucleic acid container. In certain embodiments, the molecular weight of a single strand of nucleic acid that forms the primary structure of the nucleic acid container may have a molecular weight of, for example, between 100 kDa and 10,000 kDa. In some embodiments, the molecular weight of a single strand of nucleic acid that forms the primary structure of the nucleic acid container may be, for example, at least 300 kDa, at least 600 kDa, at least 640 kDa, at least 800 kDa, at least 1,000 kDa, at least 2,000 kDa, at least 4,000 kDa, or at least 6,000 kDa. In some cases, the molecular weight of a single strand of nucleic acid that forms the primary structure of the nucleic acid container may be, for example, less than 6,000 kDa, less than 4,000 kDa, less than 2,000 kDa, less than 1,000 kDa, less than 800 kDa, less than 600 kDa, or less than 300 kDa. Other molecular weight values are also possible. Combinations of the above-referenced ranges are also possible (e.g., a molecular weight of at least 300 kDa and less than 1,000 kDa).

In some cases, a single strand of a nucleic acid used to form a nucleic acid container has a length of, for example, between 1000 bases (1 kb) and 300 kilobases (300 kb). The single strand of nucleic acid may have a length of, for example, at least 1,000 bases long (1 kb), at least 2 kb, at least 5 kb, at least 10 kb, at least 15 kb, at least 20 kb, at least 25 kb, at least 30 kb, at least 40 kb, at least 50 kb, at least 60 kb, at least 70 kb, at least 100 kb, at least 150 kb, or at least 200 kb. In certain embodiments, the single strand of nucleic acid may have a length of, for example, less than 200 kb, less than 150 kb, less than 100 kb, less than 70 kb, less than 60 kb, less than 50 kb, less than 40 kb, less than 30 kb, less than 20 kb, less than 10 kb, less than 5 kb, or less than 3 kb. Combinations of the above-referenced ranges are also possible.

Furthermore, it should be appreciated that the formation of a nucleic acid container using two or more (e.g., 2, 3, 4, 5, 6, etc.) single strands of nucleic acids that act as "scaffolds" is also contemplated. The two or more single strands of nucleic acids may have molecular weights and/or lengths in the ranges noted above, or they may have different ranges of molecular weights and/or lengths.

Figure 2A:
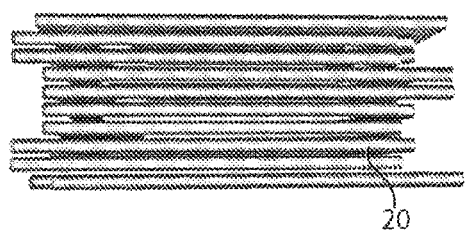
FIGS. 2A-2F show examples of different nucleic acid containers according to one set of embodiments.
Figure 2B:
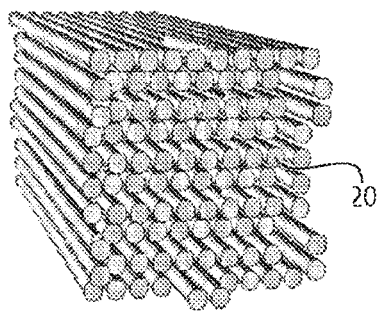
Figure 2C:
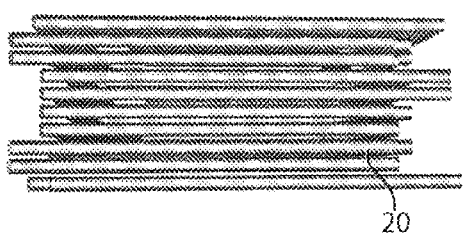
Figure 2D:
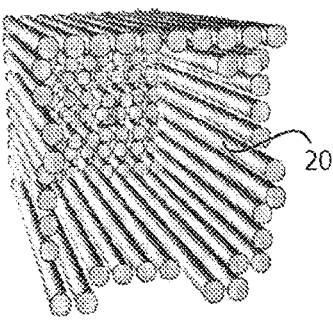
Figure 2E:
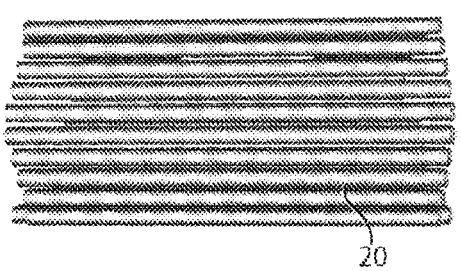
Figure 2F:
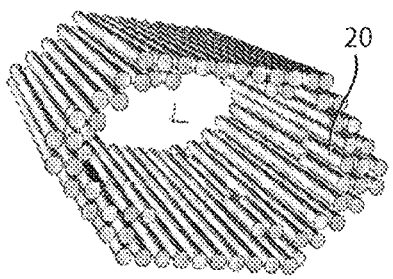

A nucleic acid container may include, in some embodiments, one or more portions that are open relative to other portions of the structure. For example, in one particular embodiment, a nucleic acid container includes two opposite ends that are open such that fluid and certain molecules can flow through its interior. An example of such a structure is shown in FIGS. 2A and 2B, which show top and side views of a container, respectively. In other embodiments, a nucleic acid container may have one open and, as shown in the embodiment illustrated in FIGS. 2C and 2D which show top and side views of a container, respectively. In other embodiments, a nucleic acid container may include more than two openings. In yet other embodiments, a nucleic acid container may be substantially closed, as shown illustratively in FIGS. 2E and 2F, which show top and side views of a container, respectively. Generally, the nucleic acid container may be made sufficiently rigid to maintain its shape under thermal and/or other external forces typical in solution and/or during nanoparticle growth conditions.

A nucleic acid container, and a cavity within a nucleic acid container, may have any suitable shape. Advantageously, nucleic acid containers can be designed to include a cavity having particular shapes that may act as a template for forming all the portions of the nanoparticle. As described herein, the shape of the cavity of a nucleic acid container may be used, in some embodiments, for forming a nanoparticle having a complementary shape. Non-limiting examples of shapes of nucleic acid container cavities include tubes, boxes, barrels, rectangles, rods, "T"s, "L"s branched structures, diamonds, stars, squares, parallelograms, rhomboids, triangles, pentagons, hexagons, and polyhedrons, including shapes substantially similar thereto. Portions of the cavity may be linear in some cases, and curved in other cases. In some instances, one or more channels are present in the nanostructure. In some cases, the cavity of a nucleic acid container has a non-spherical shape. In other cases, the cavity of a nucleic acid container has an arbitrary or irregular shape. In some embodiments, the cavity of a nucleic acid container has a symmetric shape. In some embodiments, the cavity of a nucleic acid container has an asymmetric shape (e.g., no axis of symmetry). It is to be understood that a nucleic acid container may have a variety of shapes and forms provided its structure is suitable for the application contemplated.

It should be appreciated that the cavity of the nucleic acid container may have the same shape, or a different shape, compared to the shape of the outer surface of the nucleic acid container. For instance, while the cavity of the nucleic acid container may be designed so that it has no axis of symmetry, the outer surface of the container may have a shape that does have an axis of symmetry.

A cross-section of a cavity of a nucleic acid container may have any suitable shape. For example, a cross-section may be in the shape of a rectangle, rod, "T," "L," branched structure, diamond, star, square, parallelogram, triangle, pentagon, or hexagon, including shapes substantially similar thereto. Other shapes are also possible. In some cases, a cross-section of a cavity has a non-spherical shape. In some embodiments, each cross-section of a cavity of a nucleic acid container has a non-spherical shape. In other cases, a cross-section of a cavity has an arbitrary or irregular shape, a symmetric shape, or an asymmetric shape. In certain embodiments, each cross-section of a cavity has a symmetric shape. In other embodiments, each cross-section of a cavity has an asymmetric shape.

A nucleic acid container may, in some embodiments, have a 3-dimensional shape that includes various numbers of different sides. For example, a nucleic acid container may have a cavity that is in the shape of a prism that includes five sides in its overall shape, and a cross-section that includes 3 sides. In certain embodiments, a cavity of a nucleic acid container may include, for example, between 3 and $10^6$ sides (e.g., between 3 and 100, between 3 and 70, between 3 and 50, or between 3 and 30, between 3 and 25, between 3 and 20, between 3 and 15, between 6 and 15, between 3 and 10, between 6 and 10, between 3 and 9, between 3 and 5, between 100 and $10^3$, between $10^3$ and $10^4$, between $10^4$ and $10^5$, or between $10^5$ and $10^6$ sides) in its overall shape. In some embodiments, a cavity of a nucleic acid container may include, for example, at least 4, at least 5, at least 6, at least 7, at least 8, at least 9, at least 10, at least 11, at least 12, at least 15, at least 20, at least 25, or at least 50 different sides. In certain embodiments, a cavity of a nucleic acid container may have a cross-section that includes, for example, between 3 and $10^6$ sides (e.g., between 3 and 100, between 3 and 70, between 3 and 50, or between 3 and 30, between 3 and 25, between 3 and 20, between 3 and 15, between 6 and 15, between 3 and 10, between 6 and 10, between 3 and 9, between 3 and 5, between 100 and $10^3$, between $10^3$ and $10^4$, between $10^4$ and $10^5$, or between $10^5$ and $10^6$ sides) in its overall shape. In some embodiments, a cavity of a nucleic acid container may have a cross-section that includes at least 4, at least 5, at least 6, at least 7, at least 8, at least 9, at least 10, at least 11, at least 12, at least 15, at least 20, at least 25, or at least 50 different sides. Combinations of the above-noted ranges are also possible. In some cases, a side may be non-curved (e.g., linear), although curved sides or faces may also be possible. Advantageously, nucleic acid containers including cavities having complex shapes can be formed using the methods described herein, and can be used to form nanoparticles having arbitrary complex shapes.

The angle between two sides may be, for example, between 1° and 180° (e.g., between 1° and 120°, between 1° and 90°, or between 1° and 45°). In some cases, the angle between two sides may be, for example, greater than 1°, greater than 10°, greater than 30°, greater than 45°, greater than 60°, greater than 90°, greater than 120°, or greater than 150°. In certain cases, the angle between two sides may be, for example, less than 180°, less than 150°, less than 120°, less than 90°, less than 60°, less than 45°, less than 30°, or less than 10°. Other angles are also possible. A combination of the above-noted ranges are also possible.

A nucleic acid container may comprise any suitable number of open sides. For example, a nucleic acid container may include at least one open side, at least two open sides, at least three open sides, or at least four open sides. In some cases, the nucleic acid container includes two opposing sides that are open.

Figure 3A:
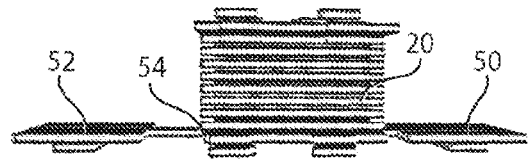
FIGS. 3A-3D show nucleic acid containers that may include one or more lids according to another set of embodiments.
Figure 3B:
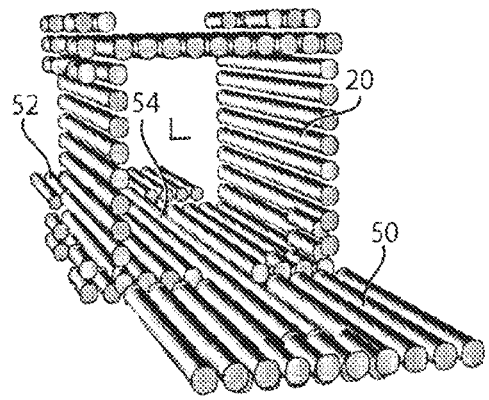
Figure 3C:
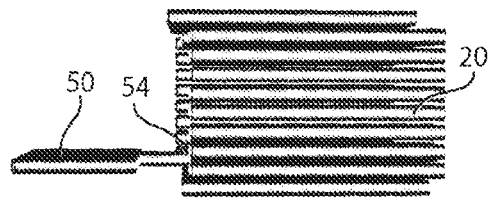
Figure 3D:
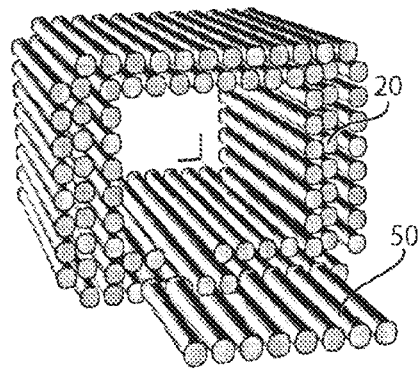

In some embodiments, a nucleic acid container comprises one or more lids that can be open or closed (e.g., reversibly or irreversibly). For example, as shown in the embodiments illustrated in FIGS. 3A and 3B, which show side and perspective views, respectively, nucleic acid container 20 may include lids 50 and 52 that may be open or closed. FIGS. 3A and 3B show the lids being in an open configuration, and may be closed by varying the position of hinge 54. Similarly, the nucleic acid container shown in FIGS. 3C and 3D include a lid 50 and a hinge 54 that may allow the opening and the closing of the lids. In some cases, the nucleic acid container includes a switchable lid. The nucleic acid container may be designed such that the lid can be switched on or off (e.g., open or closed) depending on the presence or absence of a specific nucleic acid strand, producing different dimensional controllability of the nucleic acid container. For example, in some embodiments, when the lid is open, the nucleic acid container may control the diameter of the growing nanoparticle, whereas when the lid is closed, both the diameter and length of nanoparticles may be controlled. Examples of articles and methods involving nucleic acid containers that include lids are described in more detail in U.S. Provisional Application No. 61/481,542, which is incorporated herein by reference in its entirety for all purposes.

In certain embodiments, nucleic acid containers may have suitable configurations for forming nanoparticles that are at least partially hollow. For example, as shown illustratively in FIGS. 3E and 3F, nucleic acid container 20 includes an outer wall 27 and an inner wall 55 that define the shape of cavity 30. The inner wall blocks the formation of the nanoparticle at this region, thereby allowing the formation of a nanoparticle having cross-section in the shape of a ring. It should be appreciated that other configurations of inner and outer walls of nucleic acid containers are possible to make more complex-shaped nanoparticles that are at least partially hollow.

Figure 3E:
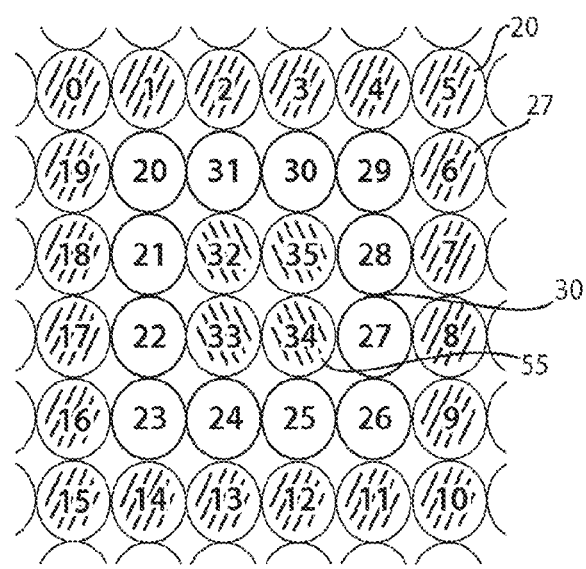
FIGS. 3E-3F show nucleic acid containers that may be used to form hollow nanoparticles according to another set of embodiments.
Figure 3F:
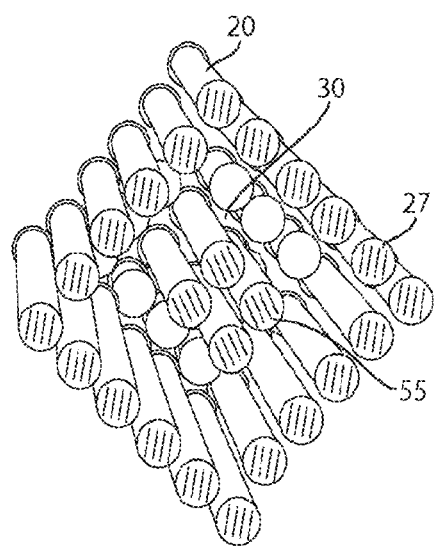

Different methods may be used to fabricate the nucleic acid containers shown in FIGS. 3E and 3F. One exemplary method involves direct folding of DNA via structural DNA nanotechnology methods, such as DNA origami or single-stranded tiles as described herein. Another exemplary method is based on the self-assembly of different DNA sub-units. For instance, DNA tube (e.g., outer wall 27) and rods (e.g., inner wall 55) may be prepared separately, and then assembled together via DNA hybridization or other interactions, to form a rod-in-tube structure like that shown in FIGS. 3E and 3F.

In some embodiments, a lid may include at least 1 binding site for binding to a complementary binding site positioned on at least a portion (e.g., a surface) of a container. The binding sites may allow secure attachment of the lid to the container, as described in more detail herein. In some cases, a lid or a surface of the container to be closed by a lid comprises at least 2, at least 4, at least 6, at least 8, at least 10, at least 12, at least 14, at least 16, at least 18, or at least 20 binding sites. The binding sites may be isolated from one another in some embodiments. The binding sites may include, for example, nucleic acid strands, although other binding units may be used.

Although many of the figures show nucleic acid containers having a single cavity, it should be appreciated that in some embodiments a nucleic acid container may include more than one cavity (and, therefore, multiple positions for the formation of multiple nanoparticles). For example, a nucleic acid container may have, in some cases, between 2 and 200 cavities (e.g., between 2 and 100, between 2 and 50, between 2 and 20, between 2 and 10, or between 2 and 5 cavities). In some embodiments, a nucleic acid container includes at least 2, at least 5, at least 10, or at least 15 cavities. In certain embodiments, a nucleic acid container includes less than 20, less than 15, less than 10, less than 5, or less than 3 cavities. Other numbers of cavities are also possible. Combinations of the above-noted ranges are also possible.

The size of a cavity of a nucleic acid container can be varied as desired. In some embodiments, a cross-sectional dimension of a cavity (e.g., as measured by the distance between two inner surface portions of the container that surround a cavity), is between 2 nm and 1 micron (e.g., between 2 nm and 500 nm, or between 2 nm and 250 nm). In some embodiments, a cross-sectional dimension of a cavity may be, for example, less than or equal to 1 micron, less than or equal to 500 nm, less than or equal to 250 nm, less than or equal to 100 nm, less than or equal to 75 nm, less than or equal to 50 nm, less than or equal to 40 nm, less than or equal to 30 nm, less than or equal to 20 nm, less than or equal to 10 nm, or less than or equal to 2 nm. In certain embodiments, a cross-sectional dimension of a cavity is greater than or equal to 1 nm, greater than or equal to 2 nm, greater than or equal to 5 nm, greater than or equal to 10 nm, greater than or equal to 20 nm, greater than or equal to 30 nm, greater than or equal to 40 nm, greater than or equal to 50 nm, greater than or equal to 100 nm, greater than or equal to 500 nm, or greater than or equal to 1 micron. Other values are also possible. Combinations of the above-noted ranges are also possible. In some embodiments, the above-noted cross-sectional dimension of the cavity is a maximum cross-sectional dimension of the cavity.

Although nucleic acid containers and cavities of nucleic acid containers having sizes generally on the order of nanometers are primarily described, in some embodiments, a variety of nucleic acid containers may be used that have significantly different sizes. For example, in some embodiments, the a plurality of containers is used with some containers being small enough to be positioned partially or fully within other containers.

The thickness of the walls of the nucleic acid container can also vary as desired. In some embodiments, the nucleic acid container comprises walls that surround a cavity, and the average thickness of the walls may be between 1 nm and 1 micron (e.g., between 1 nm and 500 nm, or between 1 nm and 250 nm). The average thickness of the walls may be, for example, less than or equal to 1 micron, less than or equal to 500 nm, less than or equal to 250 nm, less than or equal to 100 nm, less than or equal to 75 nm, less than or equal to 50 nm, less than or equal to 40 nm, less than or equal to 30 nm, less than or equal to 20 nm, less than or equal to 10 nm, or less than or equal to 1 nm. In certain embodiments, the average thickness of the walls of a nucleic acid container is greater than or equal to 1 nm, greater than or equal to 10 nm, greater than or equal to 25 nm, greater than or equal to 50 nm, greater than or equal to 100 nm, greater than or equal to 500 nm, or greater than or equal to 1 micron. Other values are also possible. Combinations of the above-noted ranges are also possible.

In some embodiments, the walls of a nucleic acid container may be formed of more than one layer of nucleic acids. Increasing the number of layers of nucleic acids may increase the rigidity (and thickness) of the wall. In some embodiments, increased wall rigidity may result in the container walls maintaining their shape during growth of a nanostructure inside the container. For instance, increased wall rigidity may confine the expansion of a nanostructure grown inside the container (e.g., by compressing the nanostructure during growth) such that the nanostructure does not grow beyond the size of the cavity of the container prior to expansion. In other embodiments, fewer number of layers may allow a nanostructure to grow beyond the size of the cavity of the container prior to expansion, and may cause the walls of the container to expand (e.g., bend) during nanostructure growth. In some embodiments, a wall of a nucleic acid container may have at least 2, at least 3, at least 4, at least 5, at least 6, at least 8, or at least 10 layers. In some cases, a wall of a nucleic acid container may have less than or equal to 20, less than or equal to 15, less than or equal to 10, less than or equal to 8, or less than or equal to 5 layers. Other values are also possible. Combinations of the above-noted ranges are also possible. The layers of the walls may have any suitable design such as a square-lattice design or a honeycomb design.

Advantageously, by controlling the thickness of walls of the nucleic acid container, diffusion kinetics, such as the diffusion kinetics of ions or molecules, across the wall of the container can be controlled. Such control may allow the tuning of the growth kinetics of the nanoparticle and/or the material composition of nanoparticle alloys. For example, in some cases, a first portion of a wall of the nucleic acid container has a first thickness, and a second portion of the wall has a second thickness, wherein the first and second thicknesses are defined by one of the above-noted ranges. A first, thicker wall portion may, for example, impede a first nanoparticle precursor solution from entering into the cavity to a greater extent than a second nanoparticle precursor solution, thereby allowing more of the second nanoparticle precursor solution to enter into the cavity at the first wall portion. As a result, the nanoparticle may have a higher amount of a material formed from the second nanoparticle precursor at the first wall portion.

Those of ordinary skill in the art are familiar with techniques to determine sizes of structures and particles. Examples of suitable techniques include dynamic light scattering (DLS), transmission electron microscopy (TEM), scanning electron microscopy, electroresistance counting, and laser diffraction. Other suitable techniques are known to those or ordinary skill in the art. Although many methods for determining sizes of nanostructures are known, the sizes described herein (e.g., cross-sectional dimensions, thicknesses) refer to ones measured by transmission electron microscopy.

The nucleic acid containers may also include other components such as those described herein (e.g., markers, binding sites, quantum dots, nanoparticles, nucleic acids, proteins, etc.). For example, in some embodiments, a nucleic acid container includes one or more inorganic structures (e.g., inorganic nanostructures), such as an inorganic nanoparticle or a quantum dot. The one or more components may fill a portion of the cavity in some embodiments, e.g., such that a nanoparticle formed by templated synthesis inside the cavity forms around the component or is combined with the component. In some cases, the component is incorporated into the nanoparticle being formed. In other embodiments, the inorganic structure is embedded in the nucleic acid container walls and does not fill a portion of the cavity.

Any suitable nanoparticle precursor can be used to form a nanoparticle as described herein. A nanoparticle precursory may be used to initiate, catalyze and/or grow a nanoparticle. In some cases, all or portions of the material of the nanoparticle precursor may be incorporated into the resulting nanoparticle. In some embodiments, a nanoparticle precursor may be used for forming a nanoparticle using a seed-mediated growth process. In some such embodiments, a nanoparticle precursor may be in a solid form. For example, the nanoparticle precursor may be in the form of a nanoparticle, such as an inorganic nanoparticle. In some cases, a nanoparticle precursor comprises a crystal. In certain cases, a nanoparticle precursor comprises a metal. Non-limiting examples of metals include Au, Ag, Cd, Cr, Co, Ti, Zn, Cu, Pb, Mn, Ni, Mg, Fe, Pd, and Pt. In other embodiments, a nanoparticle precursor comprises a semiconductor (e.g., Rh, Ge, silicon, silicon compounds and alloys, cadmium selenide, cadmium sulfide, indium arsenide, and indium phosphide). In some cases, the nanoparticle precursor may comprise a Group II-VI (e.g., IV-VI) element. In certain embodiments, the nanoparticle precursor comprises a metal oxide or a metal fluoride. In some cases, the nanoparticle precursor comprises an alloy. In some cases, the nanoparticle precursor comprises a doped compound. Combinations of such and other materials are also possible.

Non-limiting examples of nanoparticle precursors include the following. For the formation of Au, Ag, Pt and Pd nanoparticles, gold nanoparticles can be used as a precursor. Alternatively, Ag, Pt and Pd nanoparticles can be used as a precursor. For the formation of semiconductors and metal oxide nanoparticles (e.g., nanoparticles including one or more of Cd, Cr, Co, Ti, Zn, Mn, Ni, Mg, Fe, or a different material described herein), clusters or small-sized nanoparticles of corresponding materials can be used as seeds. In other embodiments, enzymes or peptides can be used as nucleation sites if they can trigger the growth of nanoparticles (e.g., organic nanoparticles). Some catalysts can also be used to trigger the growth of polymers or nanoparticles, such as $Pt(PPh_3)_2Cl_2$.

As described herein, nanoparticle precursors can also be in the form of solutions. The material composition of the resulting nanoparticle can be controlled by varying the types of precursor solutions used. Any suitable solution can be used to form a nanoparticle, and can be chosen using the description provided herein in combination with general knowledge in the art. For instance, a $HAuCl_4$ precursor solution may be used to form gold nanoparticles and a $AgNO_3$ precursor solution may be used to form silver nanoparticles (optionally in combination with other solutions such as ascorbic acid). Combinations of nanoparticle precursors and precursor solutions can also be determined by those of ordinary skill in the art in combination with the description provided herein.

In other embodiments, a nanoparticle precursor may be used for forming a nanoparticle using a non-seed-mediated growth process. For example, in some embodiments, nanoparticle precursors may be in the form of a monomer or a polymer, and the formation of a nanoparticle may comprise polymerizing and/or cross-linking of monomer and/or polymer units.

In some cases, a nanoparticle precursor may comprise an amino acid, a peptide, a nucleotide, or a nucleic acid (e.g., to form a nanoparticle that is formed substantially of amino acids, peptides, or nucleic acids).

In other cases, a nanoparticle precursor may include other functionalities such as binding sites, or may be imparted with certain surface functionalities. For example, the nanoparticle precursor may comprise a self-assembled monolayer to impart a particular surface chemistry to the precursor. In certain embodiments, the nanoparticle precursor may include a binding site or other suitable component to allow it to be attached to a portion of the nucleic acid container. In other embodiments, the nanoparticle precursor may be suspended in the cavity of the container and not attached to a surface of the container.

A nanoparticle precursor may have any suitable size. In some embodiments, a nanoparticle precursor has at least one cross-sectional dimension that is between 0.5 nm and 1 micron (e.g., between 0.5 nm and 500 nm, or between 0.5 nm and 250 nm). In some embodiments, a nanoparticle precursor has at least one cross-sectional dimension that is, for example, less than or equal to 1 micron, less than or equal to 500 nm, less than or equal to 250 nm, less than or equal to 100 nm, less than or equal to 75 nm, less than or equal to 50 nm, less than or equal to 40 nm, less than or equal to 30 nm, less than or equal to 20 nm, less than or equal to 10 nm, less than or equal to 5 nm, less than or equal to 1 nm, or less than or equal to 0.5 nm. In some embodiments, a nanoparticle precursor has at least one cross-sectional dimension that is greater than or equal to 0.5 nm, greater than or equal to 1 nm, greater than or equal to 2 nm, greater than or equal to 5 nm, greater than or equal to 10 nm, greater than or equal to 20 nm, or greater than or equal to 50 nm. Other sizes are also possible. Combinations of the above-noted ranges are also possible.

In some cases, the size (e.g., volume) of a nanoparticle precursor is at least 500 times, at least 300 times, at least 200 times, at least 100 times, at least 50 times, at least 20 times, at least 10 times, at least 5 times, or at least 2 times smaller than the nanoparticle that is formed from the precursor or than the cavity of the container. Other sizes are also possible.

In certain embodiments, a nanoparticle precursor has an average molecular weight of, for example, between 20 Da and 10 kDa (e.g., between 20 Da and 5 kDa, or between 20 Da and 1 kDa). A nanoparticle precursor has an average molecular weight of, for example, less than or equal to 10 kDa, less than or equal to 5 kDa, less than or equal to 1 kDa, less than or equal to 500 Da, less than or equal to 200 Da, less than or equal to 100 Da, less than or equal to 50 Da, or less than or equal to 20 Da. In some embodiments, a nanoparticle precursor has an average molecular weight of greater than or equal to 10 Da, greater than or equal to 20 Da, greater than or equal to 50 Da, greater than or equal to 100 Da, greater than or equal to 200 Da, greater than or equal to 500 Da, greater than or equal to 1 kDa, or greater than or equal to 10 kDa. Other molecular weights are also possible. Combinations of the above-noted ranges are also possible.

As described herein, a nanoparticle having a unique and/or predetermined shape can be formed using the methods described herein. For instance, a nanoparticle having a specific shape (and/or size) can be formed by designing a cavity of a nucleic acid container to have the complement of the desired shape (and/or size) of the nanoparticle. The cavity may then act as a template for forming all the portions of the nanoparticle. Non-limiting examples of shapes of nanoparticles include tubes, boxes, barrels, rectangles, rods, "T"s, "L"s branched structures, diamonds, stars, squares, parallelograms, triangles, pentagons, hexagons, polyhedrons, and rings, including shapes substantially similar thereto. In some cases, a nanoparticle has a non-spherical shape. In other cases, a nanoparticle has an arbitrary or irregular shape. In some embodiments, a nanoparticle has a symmetric shape. A symmetric shape may include, in some embodiments, at least 1, at least 2, at least 3, or at least 4 axes of symmetry. In some embodiments, a nanoparticle has an asymmetric shape (e.g., no axis of symmetry).

In some embodiments, the nanoparticles formed by the methods described herein are solid or solid-like (e.g., with solid cores), and are not hollow structures. In other embodiments, portions of the nanoparticle may be hollow, e.g., as described herein with respect to FIGS. 3E and 3F. The hollow portion (e.g., cavity) of the nanoparticle may be completely enclosed by the walls of the nanoparticle, or partially enclosed (e.g., having one or more ends that are opened).

A cross-section of a nanoparticle may have any suitable shape. For example, a cross-section may be in the shape of a rectangle, rod, "T," "L," branched structure, diamond, star, square, parallelogram, triangle, pentagon, hexagon, or ring, including shapes substantially similar thereto. Other shapes are also possible. In some cases, a cross-section of a nanoparticle has a non-spherical shape. In some embodiments, each cross-section of a nanoparticle has a non-spherical shape. In other cases, a cross-section of a nanoparticle has an arbitrary or irregular shape, a symmetric shape, or an asymmetric shape. In certain embodiments, each cross-section of a nanoparticle has a symmetric shape. In other embodiments, each cross-section of a nanoparticle has an asymmetric shape.

A nanoparticle may, in some embodiments, have a 3-dimensional shape that includes various numbers of different sides. For example, a nanoparticle may be in the shape of a prism that includes four sides. In certain embodiments, a nanoparticle may include, for example, between 3 and $10^6$ sides (e.g., between 3 and 100, between 3 and 70, between 3 and 50, or between 3 and 30, between 3 and 25, between 3 and 20, between 3 and 15, between 6 and 15, between 3 and 10, between 6 and 10, between 3 and 9, between 3 and 5, between 3 and 8, between 20 and 50, between 50 and 100, between 100 and $10^3$, between $10^3$ and $10^4$, between $10^4$ and $10^5$, or between $10^5$ and $10^6$ sides). In some cases, a nanoparticle includes at least 4, at least 5, at least 6, at least 7, at least 8, at least 9, at least 10, at least 11, at least 12, at least 15, at least 20, at least 25, at least 50, at least 100, at least $10^3$, at least $10^4$, or at least $10^5$ different sides.

As described herein, in some embodiments, a nanoparticle comprises at least one surface portion having a shape that is complimentary to a shape of an inner surface portion of a nucleic acid container. A surface portion generally refers to a portion of a surface that has a surface area that is greater than the surface area of a single atom. In some instances, a surface portion may have a surface area of at least 1 nm$^2$, at least 2 nm$^2$, at least 5 nm$^2$, at least 10 nm$^2$, at least 15 nm$^2$, at least 20 nm$^2$, at least 25 nm$^2$, at least 30 nm$^2$, at least 50 nm$^2$, at least 200 nm$^2$, at least 200 nm$^2$, at least 500 nm$^2$, or at least 1000 nm$^2$ (where the largest surface portion is the surface area of the entire nanoparticle).

In some cases, a nanoparticle has at least one surface portion that is complimentary to a shape of an inner surface portion of a nucleic acid container at the sub-nanometer (e.g., 0.5 nm) level. For example, growth of a nanoparticle inside a container may stop or significantly slow down upon reaching the confines of the inner surface portion of the container. In some such embodiments, the surface chemistry and/or physical interactions between the nanoparticle and the inner surface of the container prevents further growth of the nanoparticle. For example, electrostatic interactions between the negatively charged phosphate groups of the nucleic acid container and the positively charged groups of the nanoparticle or nanoparticle precursor may prevent further growth of the nanoparticle. The particular orientation of the atoms of the inner surface portion of the nucleic acid container may determine the final shape of the resulting nanoparticle, where the inner surface portion and the shape of a surface portion of the resulting nanoparticle are complementary, e.g., at the sub-nanometer level.

In some embodiments, a relatively high percentage of the surface area of a nanoparticle is complementary to a shape of an inner surface (e.g., cavity) of a nucleic acid container at the sub-nanometer (e.g., 0.5 nm) level. For example, at least 50%, at least 60%, at least 70%, at least 80%, at least 90%, at least 95%, at least 97%, at least 98%, or at least 99% of the surface area of the nanoparticle may be complementary to a shape of an inner surface of a nucleic acid container at the sub-nanometer level. In other embodiments, 100% of the surface area of the nanoparticle is complementary to a shape of an inner surface of the nucleic acid container at the sub-nanometer level.

In other embodiments, the resulting nanoparticle has at least one surface portion that is complementary to a shape of an inner surface portion of a nucleic acid container at the nanoscale level (e.g., 1 nm or greater). For example, growth of a nanoparticle inside a container may stop or significantly slow down before reaching the confines of the inner surface of the container such that the resulting nanoparticle has a volume less than the volume of the cavity. In some such embodiments, the nanoparticle has a substantially similar shape as that of the cavity, and is complementary with the inner walls of the container at the nanoscale level, but is not complementary with the inner walls of the container at the sub-nanometer level.

In some embodiments, a relatively high percentage of the surface area of a nanoparticle is complementary to a shape of an inner surface portion of a nucleic acid container at the nanoscale level (e.g., 1 nm or greater) level. For example, at least 50%, at least 60%, at least 70%, at least 80%, at least 90%, at least 95%, at least 97%, at least 98%, or at least 99% of the surface area of the nanoparticle is complementary to a shape of an inner surface portion of the a nucleic acid container at the nanoscale level. In other embodiments, 100% of the surface area of the nanoparticle is complementary to a shape of an inner surface portion of the nucleic acid container at the nanoscale level.

A nanoparticle having complementarity at both the molecular (e.g., Angstrom) and nanoscale level for different portions of the nanoparticle is also possible.

In yet other embodiments, the resulting nanoparticle includes one or more surface portions that are not complementary to the inner surface portions of a nucleic acid container. For example, fabrication of a nanoparticle in a nucleic acid container that includes two open ends may result in a nanoparticle that has a middle portion that is complementary (e.g., at the molecular level or at a nanoscale level) with inner surface portions of the nucleic acid container, but having ends that are not complementary to any portions of the nucleic acid container. In some such embodiments, the nanoparticle may grow outside of the cavity of the nucleic acid container and may be shaped by other factors.

In certain embodiments, a nanoparticle comprises at least two opposing surface portions, each of the at least two opposing surface portions having a shape that is complementary to a shape of an inner surface portion of the nucleic acid container. The complementarity may be at the molecular level or at the nanoscale level as described above. For example, as shown in the embodiment illustrated in FIG. 1A, two opposing surface portions of the cavity of the nucleic acid container are shown as inner surface portions 26A and 26B. The opposing surface portions may be parallel to one another in some embodiments. Upon formation of nanoparticle 38, surface portions of the nanoparticle at these positions may be complementary to inner surface portions 26A and 26B of the nucleic acid container.

In other embodiments, the nanoparticle comprises at least two adjacent surface portions, each of the at least two adjacent surface portions having a shape that is complementary to a shape of an inner surface portion of the nucleic acid container. For example, as shown in the embodiment illustrated in FIG. 1A, adjacent inner surface portions 26A and 26C of the nucleic acid cavity may be used to facilitate the formation of nanoparticle 38. Accordingly, nanoparticle 38 may include adjacent surface portions that are complementary to the inner surface portions of the cavity at these positions.

A nanoparticle can be formed of any suitable material. A nanoparticle formed by the methods described herein may be an inorganic nanoparticle in some embodiments. In some cases, a nanoparticle comprises a metal. Non-limiting examples of metals include Au, Ag, Cd, Cr, Co, Ti, Zn, Cu, Pb, Mn, Ni, Mg, Fe, Pd, and Pt. In other embodiments, a nanoparticle comprises a semiconductor (e.g., Rh, Ge, silicon, silicon compounds and alloys, cadmium selenide, cadmium sulfide, indium arsenide, and indium phosphide). In some cases, the nanoparticle may comprise a Group II-VI (e.g., IV-VI) element. In certain embodiments, the nanoparticle comprises a metal oxide or a metal fluoride. In some cases, the nanoparticle a comprises an alloy. In some cases, the nanoparticle a comprises a doped compound. Combinations of such and other materials are also possible. The nanoparticle may be electronically and/or thermally conductive in some embodiments, or non-electronically and/or non-thermally conductive in other embodiments.

In other embodiments, a nanoparticle formed by the methods described herein may be an organic nanoparticle. In some cases, a nanoparticle may comprise a polymer, which may be cross-linked or non-crosslinked. The polymer may be, for example, a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen. Conductive polymers may be used in some embodiments. In certain embodiments, the nanoparticle does not include a polymeric material (e.g., it is non-polymeric). In some cases, a nanoparticle may comprise a protein, an enzyme, or a peptide.

The surface of the nanoparticle may include the material used to form the interior portions of nanoparticle, or may otherwise be imparted with certain surface functionalities such as binding sites or other components. For example, the nanoparticle may comprise a self-assembled monolayer to impart a particular surface chemistry to the nanoparticle. In some cases, a nanoparticle surface may be passivated by one or more chemicals to facilitate attachment of components.

A nanoparticle may have any suitable size. In some embodiments, a nanoparticle has at least one cross-sectional dimension (or at least two cross-sectional dimensions) that is/are between 2 nm and 1 micron (e.g., between 2 nm and 500 nm, or between 2 nm and 250 nm). In some embodiments, a nanoparticle has at least one cross-sectional dimension (or at least two cross-sectional dimensions) that is/are less than or equal to 1 micron, less than or equal to 500 nm, less than or equal to 250 nm, less than or equal to 100 nm, less than or equal to 75 nm, less than or equal to 50 nm, less than or equal to 40 nm, less than or equal to 30 nm, less than or equal to 20 nm, less than or equal to 10 nm, or less than or equal to 5 nm. In certain embodiments, the nanoparticle has at least one cross-sectional dimension (or at least two cross-sectional dimensions) that is/are greater than or equal to 2 nm, greater than or equal to 5 nm, greater than or equal to 10 nm, greater than or equal to 50 nm, or greater than or equal to 100 nm. Combinations of the above-noted ranges are also possible. In some cases, the above-noted cross-sectional dimension is a maximum cross-sectional dimension.

In some cases, a nanoparticle has a volume of, for example, between 8 $nm^3$ and 1 $\mu m^3$ ($1*10^9$ $nm^3$). In certain embodiments, a nanoparticle has a volume of, for example, at least 20 $nm^3$, at least 50 $nm^3$, at least 100 $nm^3$, at least 500 $nm^3$, at least $1\times10^3$ $nm^3$, at least $5\times10^3$ $nm^3$, at least $1\times10^4$ $nm^3$, at least $5\times10^4$ $nm^3$, at least $1\times10^5$ $nm^4$, at least $5\times10^5$ $nm^3$, at least $1\times10^6$ $nm^3$, at least $5\times10^6$ $nm^3$, at least $1\times10^7$ $nm^3$, at least $5\times10^7$ $nm^3$, at least $1\times10^8$ $nm^3$, or at least $5\times10^8$ $nm^3$. In some embodiments, a nanoparticle has a volume of, for example, less than $1\times10^9$ $nm^3$, less than $5\times10^8$ $nm^3$, less than $1\times10^8$ $nm^3$, less than $5\times10^7$ $nm^3$, less than $1\times10^7$ $nm^3$, less than $5\times10^6$ $nm^3$, less than $1\times10^6$ $nm^3$, less than $5\times10^5$ $nm^3$, less than $1\times10^5$ $nm^3$, less than $5\times10^4$ $nm^3$, less than $1\times10^4$ $nm^3$, less than $5\times10^3$ $nm^3$, less than $1\times10^3$ $nm^3$, less than 500 $nm^3$, less than 100 $nm^3$, less than 50 $nm^3$, or less than 20 $nm^3$. Other ranges are also possible. A combination of the above-noted ranges are also possible. In certain embodiments, such volumes are based on the use of a single nucleic acid scaffold. Larger volumes may be possible using multiple nucleic acids scaffolds.

As described herein, a nanoparticle may have a size, dimension (e.g., length, width, height), cross-sectional dimension, and/or volume that is substantially similar to that of a cavity of a container in which the nanoparticle is grown. In other embodiments, a nanostructure may have a size, dimension (e.g., length, width, height), cross-sectional dimension, and/or volume that is less than that of a cavity of a container in which the nanoparticle is grown. For example, growth of the nanoparticle may be stopped prior to the nanoparticle reaching one or more sides of the container. In other embodiments, a nanostructure may have a size, dimension (e.g., length, width, height), cross-sectional dimension, and/or volume that is greater than that of a cavity of a container in which the nanoparticle is grown. For example, the walls of the container may be designed to be flexible such that the nanoparticle grown within causes the walls of the container to expand during growth. Other configurations of the nanoparticle and/or container are also possible.

In some cases, the volume of the nanoparticle may be at least two times, at least five times, at least 10 times, at least 20 times, at least 30 times, at least 50 times, at least 100 times, at least 200 times, at least 500 times, or at least 1,000 times the volume of a nanoparticle precursor used to form the nanoparticle. The resulting volume of the nanoparticle may depend, at least in part, on the size of the cavity of a nucleic acid container, which may be varied as described herein. It should be appreciated that nanoparticles having sizes smaller or larger than the volume of the cavity of the nucleic acid container are also possible. For example, portions of a nanoparticle may be fabricated inside a container, and other portions of the nanoparticle may grow outside of the container.

In some cases, a nanoparticle has an aspect ratio of at least 2:1, at least 3:1, at least 5:1, at least 10:1, or at least 20:1. Other values of aspect ratio are also possible. As used herein, "aspect ratio" refers to the ratio of a length to a width, where length and width measured perpendicular to one another, and the length refers to the longest linearly measured dimension.

As described herein, in some cases all or portions of a nanoparticle may be encapsulated or coated by a nucleic acid nanostructure. For example, at least 50%, at least 60%, at least 70%, at least 80%, at least 90%, at least 95%, at least 97%, at least 98%, or at least 99% of the surface area of a nanoparticle may be encapsulated or coated by a nucleic acid nanostructure. In some instances, the entire surface area of a nanoparticle is encapsulated or coated by a nucleic acid nanostructure. In some such embodiments, all or portions of the nanoparticle may be attached to the nucleic acid nanostructure. For example, all or portions of the nanoparticle may be physisorbed onto the nucleic acid nanostructure. In other embodiments, all or portions of the nanoparticle are not attached to the nucleic acid nanostructure but are merely adjacent to the nucleic acid nanostructure. The nanoparticle may be in contact with, or not in contact with, the nucleic acid nanostructure during encapsulation.

Compositions including nanoparticles that have one or more of the features described herein are also provided. For example, in some cases, a composition includes nanoparticles such that at least 80%, at least 90%, at least 95%, at least 97%, at least 98%, or at least 99% of the nanoparticles in the composition are non-spherical, have no axis of symmetry, are complementary to an inner surface portion of a nucleic acid container (at a molecular level or at an atomic level), or are encapsulated/coated by a nucleic acid container.

In another set of embodiments, one or more surfaces of a nanoparticle can be patterned (e.g., in two dimensions and/or in three dimensions) with one or more components. This can be done by, for example, fabricating a pattern of one or more components onto the interior surface of the nucleic acid container used to form the nanoparticle, and then triggering the growth of the nanoparticle within the container. The growth of the nanoparticle within the container can result in the incorporation of the pattern of the one or more components onto the surface of the nanoparticle. With this method, nano-scaled structures with details at the nanometer or sub-nanometer level can be fabricated. Examples of such structures include metallic coins and arbitrary shaped nano-scaled electronic devices. Other structures such as core-shell type structures in the form of alloys or polymer/metal hybrid structures can also be formed. In some such embodiments, the shape of the shell layer may be different from the general shape of the core. For example, a hexagonal shell may surround a pentagon core. The methods described herein are a more rational way of fabricating arbitrary pre-designed structures compared to certain existing methods.

In some embodiments, a fabricated nanoparticle may be used as a template to fabricate other materials that cannot be directly prepared by DNA-directed synthesis (e.g., those requiring high temperatures or pressures, and/or those formed in organic solutions). In some embodiments, nanoparticles formed by the methods described herein that are at least partially hollow may be used as a template to form a secondary nanostructure within the hollow portion (e.g., cavity) of the nanoparticle. In other embodiments, the outer surface of the nanoparticle can be used as a template to form a larger secondary nanostructure. The nanoparticle that is used as a template may be optionally removed after forming the secondary nanostructure. Nanoparticles formed of or comprising, for example, gold, silver, or platinum may be suitable for use as templates. Other materials for use as templates may also be possible. A secondary nanostructure formed using a nanoparticle as a template may be made of any suitable material, including those materials described herein for nanoparticles in general. The material of the secondary nanostructure may be the same as, or different from, the material of the nanoparticle used as the template.

The hollow portion (e.g., cavity) of a nanoparticle and/or a secondary nano structure formed using a nanoparticle may have any suitable size. In some embodiments, a hollow portion (e.g., cavity) of a nanoparticle and/or a secondary nanostructure has at least one cross-sectional dimension (or at least two cross-sectional dimensions) that is/are between 1 nm and 1 micron (e.g., between 1 nm and 500 nm, or between 1 nm and 250 nm). In some embodiments, a hollow portion (e.g., cavity) of a nanoparticle and/or a secondary nanostructure has at least one cross-sectional dimension (or at least two cross-sectional dimensions) that is/are less than or equal to 1 micron, less than or equal to 500 nm, less than or equal to 250 nm, less than or equal to 100 nm, less than or equal to 75 nm, less than or equal to 50 nm, less than or equal to 40 nm, less than or equal to 30 nm, less than or equal to 20 nm, less than or equal to 10 nm, or less than or equal to 5 nm. In certain embodiments, a hollow portion (e.g., cavity) of a nanoparticle and/or a secondary nanostructure has at least one cross-sectional dimension (or at least two cross-sectional dimensions) that is/are greater than or equal to 2 nm, greater than or equal to 5 nm, greater than or equal to 10 nm, greater than or equal to 50 nm, or greater than or equal to 100 nm. Combinations of the above-noted ranges are also possible. In some cases, the above-noted cross-sectional dimension is a maximum cross-sectional dimension.

In some cases, a hollow portion of a nanoparticle and/or a secondary nanostructure has a volume of, for example, between 1 $nm^3$ and 1 $\mu m^3$ ($1*10^9$ $nm^3$). In certain embodiments, a hollow portion of a nanoparticle and/or a secondary nanostructure has a volume of, for example, at least 20 $nm^3$, at least 50 $nm^3$, at least 100 $nm^3$, at least 500 $nm^3$, at least $1 \times 10^3$ $nm^3$, at least $5 \times 10^3$ $nm^3$, at least $1 \times 10^4$ $nm^3$, at least $5 \times 10^4$ $nm^3$, at least $1 \times 10^5$ $nm^4$, at least $5 \times 10^5$ $nm^3$, at least $1 \times 10^6$ $nm^3$, at least $5 \times 10^6$ $nm^3$, at least $1 \times 10^7$ $nm^3$, at least $5 \times 10^7$ $nm^3$, at least $1 \times 10^8$ $nm^3$, or at least $5 \times 10^8$ $nm^3$. In some embodiments, a hollow portion of a nanoparticle and/or a secondary nanostructure has a volume of, for example, less than $1 \times 10^9$ $nm^3$, less than $5 \times 10^8$ $nm^3$, less than $1 \times 10^8$ $nm^3$, less than $5 \times 10^7$ $nm^3$, less than $1 \times 10^7$ $nm^3$, less than $5 \times 10^6$ $nm^3$, less than $1 \times 10^6$ $nm^3$, less than $5 \times 10^5$ $nm^3$, less than $1 \times 10^5$ $nm^3$, less than $5 \times 10^4$ $nm^3$, less than $1 \times 10^4$ $nm^3$, less than $5 \times 10^3$ $nm^3$, less than $1 \times 10^3$ $nm^3$, less than 500 $nm^3$, less than 100 $nm^3$, less than 50 $nm^3$, or less than 20 $nm^3$. Other ranges are also possible. A combination of the above-noted ranges are also possible.

As described herein, nanoparticles, which may be optionally coated or encapsulated by a nucleic acid container or nanostructure, may have a variety of different shapes. In some embodiments, the unique shapes of the nanoparticles can be used to position one or more components (e.g., binding sites, markers, ligands, etc.) on different portions of a nanoparticle surface and/or a surface of the nucleic acid container to allow the nanoparticle or nanostructure to be addressed in different ways. For example, a nanoparticle having eight different sides may be functionalized with one or more different components at each of the eight different sides. In some cases, the components are in the form of isolated components that can be added to unique positions on the nanoparticle or nanostructure. For instance, a single, isolated component may be positioned on a single side of the nanoparticle, with each of the different sides of the nanoparticle including a different single, isolated component. These and other embodiments may be useful for detecting a variety of different targets as described in more detail below.

In some embodiments, the positioning of a component on precise locations of a nanoparticle and/or nanostructure may be controlled by the particular chemistry of the nucleic acid container. For example, a nanoparticle that has eight different sides may be surrounded (partially or fully) by a nucleic acid container that has an inner cavity having eight different sides, and walls with different chemistry at each of the different sides. A component may be designed such that it has an affinity for a certain portion of the nucleic acid container or nanostructure at one of the sides that coats or encapsulates a side of the nanoparticle. Thus, by designing the nucleic acid container to have specific sequences or chemistry at particular positions, the addition of a specific component to the surface of the nucleic acid container and/or the surface of the nanoparticle at one of those positions can be performed. Similarly, additional components can be specifically added to different positions of the surface of the nucleic acid container and/or the surface of the nanoparticle using this method.

As described herein, the nucleic acid container is typically porous such that small pores or holes through the thickness of the walls of the container allow access to the outer surface of the nanoparticle. The outer surface of the nucleic acid container and/or the pores of the nucleic acid container can be designed to include a particular nucleic acid sequence, hydrophilicity, hydrophobicity, charge and/or size that favors positioning of a particular component into the pore or onto the surface of the container. Likewise, the component to be added may be designed to include a complementary nucleic acid sequence, hydrophilicity, hydrophobicity, charge, and/or size such that it has an affinity for a particular portion of the nucleic acid container. In some cases, upon the component being matched with a particular portion of the nucleic acid container, the component may be inserted all the way through the pore such that it contacts a portion of the surface of the nanoparticle.

In some such embodiments, the end of the component may have a particular chemistry that allows it to be attached to the surface of the nanoparticle. For example, a component may be functionalized with a thiol that allows it to be physisorbed to a gold nanoparticle. In some embodiments in which the component is attached directly to the nanoparticle, all or portions of the nucleic acid container that surrounds the nanoparticle (partially or fully) may be optionally removed, while the component remains attached to the surface of the nanoparticle. In other embodiments, however, the nucleic acid container may remain surrounding the nanoparticle even after attachment of the component. In yet other embodiments, the component is not attached to the surface of the nanoparticle but is attached to a portion of the nucleic acid container. Attachment to both the surface of the nanoparticle and a portion of the nucleic acid container is also possible. Any suitable method of attachment, e.g., to the surface of the nanoparticle and/or to a portion of the nucleic acid container, may be used such as covalent bonding, physisorption, chemisorption, or attachment through ionic interactions, hydrophilic and/or hydrophobic interactions, electrostatic interactions, van der Waals interactions, or combinations thereof.

A component may have any suitable orientation with respect to the nanoparticle or nucleic acid container. For instance, a component may be oriented substantially perpendicular to a wall of the nanoparticle or nucleic acid container. In some embodiments, a component may be oriented at a particular angle or range of angles with respect to a wall of the nanoparticle or nucleic acid container (e.g., between 0° and 90°, between 0° and 15°, between 15° and 45°, between 45° and 60°, or between 60° and 90°).

In certain embodiments, an inorganic nanoparticle comprising an isolated nucleic acid strand attached to a surface of the inorganic nanoparticle is provided, wherein the inorganic nanoparticle has a non-spherical shape. In certain embodiments, an inorganic nanoparticle coated with a nucleic acid container is provided, wherein the nucleic acid container comprises pores. A binding site, such as an isolated nucleic acid strand may be attached to a surface of the inorganic nanoparticle, and may extend from the surface of the inorganic nanoparticle, through a pore of the nucleic acid container. In some cases, the length of the binding site (e.g., isolated nucleic acid strand) is longer than the thickness of the nucleic acid container, such that the binding site extends outwards from the nucleic acid container.

By using the unique chemistry of the nucleic acid container that surrounds all or portions of the nanoparticle to direct positioning of the components (either directly to the surface of the nanoparticle or to the nucleic acid container), control of many different parameters can be provided. FIGS. 4A-4D show examples of different parameters that can be controlled when adding a component to a nucleic acid nanostructure and/or a nanoparticle.

Figure 4A:
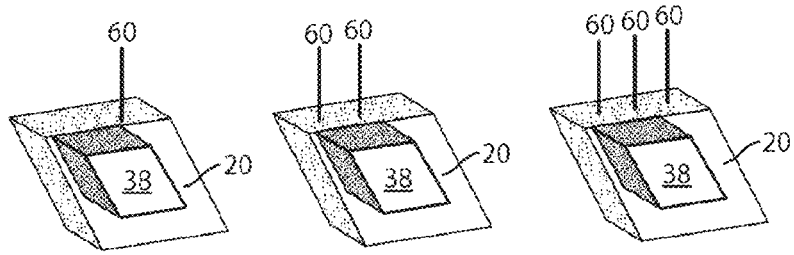

As shown in the embodiments illustrated in FIG. 4A, the number of components 60 may be varied along one or more surface portions of the nucleic acid container and/or the nanoparticle. For example, in some embodiments, a single isolated component 60 may be positioned on a single side of the nucleic acid container and/or nanoparticle. In other embodiments, two isolated components can be positioned on a single side of the nucleic acid container and/or the nanoparticle. In yet other embodiments, three or more components 60 can be positioned on a single side of a nucleic acid container and/or a nanoparticle.

Figure 4B:
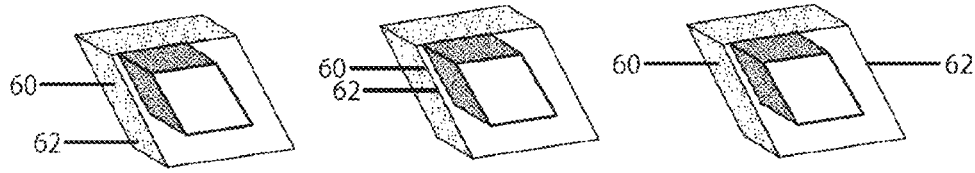

As shown in the embodiments illustrated in FIG. 4B, the distance between two or more components can also be controlled. For example, a first component 60 and a second component 62 may be positioned relatively far apart from each other at a side of a nucleic acid container and/or nanoparticle. In other embodiments, two components can be positioned relatively close to one another, or on opposite sides of the nucleic acid container and/or nanoparticle.

Figure 4C:
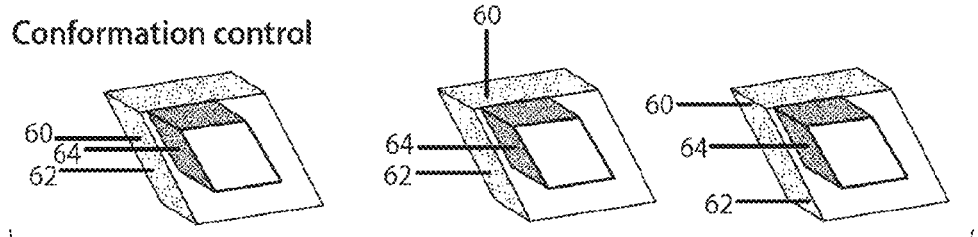

As shown in the embodiments illustrated in FIG. 4C, conformational control can also be provided. For instance, the positioning of different components at unique positions on one or more sides of a nucleic acid container and/or a nanoparticle may allow the components to interact with each other, and/or with portions of the nucleic acid container, so as to provide a particular structural configuration of the components and/or to change the structural configuration of the container.

Figure 4D:
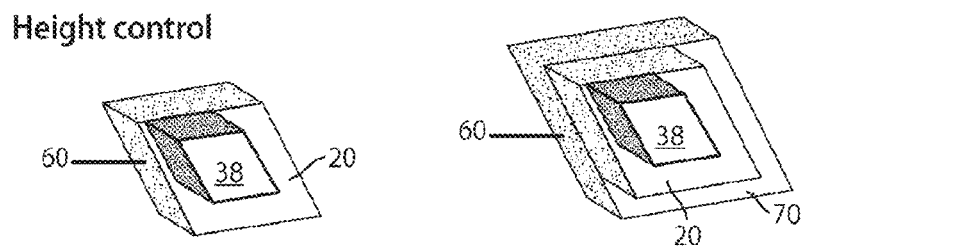

Furthermore, as shown in the embodiments illustrated in FIG. 4D, the length of the components and/or the distance of the component from the surface of the nanoparticle can also be controlled. For example, if it is desirable to include a component 60 that is positioned a short distance away from the surface of nanoparticle 38, the nucleic acid container having a relatively thin wall can be used. If it is desirable to include a component 20 that is relatively further away from the surface of nanoparticle 38, a relatively thick wall can be used. In some embodiments, a relatively thick wall may be obtained by using a second layer 70 to coat all or portions of nucleic acid container 20. The second layer may be formed using a nucleic acid polymer or any other material described herein that may be suitable for use as a coating. Additionally or alternatively, the length of component 60 may be varied to control the distance between the end of the component and a surface of the nucleic acid container and/or the surface of the nanoparticle.

It should be appreciated that the types of parameters that can be controlled as shown in FIGS. 4A-4D are merely examples, and that other parameters with respect to the positioning of components relative to nucleic acid containers and/or nanoparticles may be possible. Additionally, it should be appreciated that multiple components (e.g., binding sites), either homogeneous or heterogeneous, may be positioned on the same surface with controlled conformation or relative orientation.

FIGS. 4E and 4F show examples of how the surface addressability of the structures can be used to form assemblies (e.g., higher ordered structures) using specific orientations of the structures. For instance, nucleic acid container 20 having different sides a-f may include a nanostructure 37 attached to an inner surface of the container. The nanostructure may fill a portion of the cavity of the nucleic acid container. Nanoparticle 38 may be formed inside a cavity using the nucleic acid container and nanostructure 37 as a template as described herein. Components 60 at each side of the structure may be unique and designed to bind with specific components on the sides of other structures to form an assembly having a specific configuration, as shown illustratively in FIG. 4F. Additional examples of assembles using surface-specific interactions are described in more detail below.

In certain embodiments involving the positioning of isolated components on a nucleic acid container and/or nanoparticle, a component may be "isolated" in the sense that it is positioned a certain distance away from another component that is attached to the same nucleic acid container and/or nanoparticle such that the isolated component can be uniquely identified and distinguished from the other components (e.g., at the nanoscale level). In some cases, an isolated component may facilitate binding or attachment of other entities to the component, since it is isolated and avoids or reduces the amount of steric interactions with other nearby components attached to the same nucleic acid container and/or nanoparticle.

In some cases, a first component (e.g., an isolated component) is positioned at a distance of least 2 nm, at least 5 nm, at least 10 nm, at least 15 nm, at least 20 nm, at least 30 nm, at least 40 nm, or at least 50 nm apart from the nearest second component attached to the same nucleic acid container and/or nanoparticle. In certain cases, a first component (e.g., an isolated component) is positioned at a distance of less than or equal to 500 nm, less than or equal to 200 nm, less than or equal to 100 nm, less than or equal to 50 nm, less than or equal to 40 nm, less than or equal to 30 nm, less than or equal to 20 nm, less than or equal to 15 nm, less than or equal to 10 nm, or less than or equal to 50 nm apart from the nearest second component. Other distances are also possible. Combinations of the above-noted ranges are also possible. In other embodiments, components may be positioned directly adjacent to one another (e.g., in the form of a self-assembled monolayer) such that the individual components are not isolated and/or not distinguishable from one another (e.g., at the nanoscale level).

Any suitable number of components (whether isolated or not isolated) may be attached to a nucleic acid container and/or nanoparticle. In some embodiments, the nucleic acid nanostructure and/or a nanoparticle may include, for example, between 2 and 500 components (e.g., between 2 and 100, between 2 and 50, or between 2 and 20 components). In some embodiments, the nucleic acid nanostructure and/or a nanoparticle may include at least 2, at least 4, at least 6, at least 8, at least 10, at least 12, at least 14, at least 20, at least 30, at least 40, at least 50, at least 70, or at least 100 different components. In other embodiments, the nucleic acid nanostructure and/or a nanoparticle includes less than 100, less than 70, less than 50, less than 40, less than 30, less than 20, less than 10, less than 7 different components. In some embodiments, each of the components are isolated from one another as described herein. Other numbers of components are also possible. Combinations of the above-noted ranges are also possible.

As described herein, two or more components positioned on a surface of a nucleic acid container and/or a nanoparticle may be positioned at any suitable orientation with respect to one another. In some embodiments, at least two components are attached to opposite surface portions of the nucleic acid container and/or nanoparticle. In other embodiments, at least two components are positioned on adjacent surface portions of the nucleic acid container and/or nanoparticle. In some cases, a first component is positioned on a surface of a nanoparticle and a second component is attached to the surface of a nucleic acid container. Other configurations and orientations are also possible.

The methods described herein may be used to "print" components such as proteins, organic molecules, and inorganic nanoparticles, onto surfaces of the nanoparticles that are formed by the methods described herein. Components may first be decorated onto the interior surface of nucleic acid container in a pre-designed pattern, and later transferred onto the exterior surface of the nanoparticle grown inside the nucleic acid container through the interactions described herein (e.g., physisorption, covalent bonding, van der Waal interactions, etc.), while retaining the pre-designed pattern. For example, nanoparticles that grow inside the container may reach the inner walls of the container where they contact the component and allow attachment of the component to the nanoparticle surface. In some embodiments, even after the removal of nucleic acid container, the component may remain on the surface of the nanoparticle. In other embodiments, components can be attached to staple strands (e.g., nucleic acids) that are hybridized to the container scaffold and hold the scaffold in the target shape. Since different staple strands may be used for holding together different parts of the container, the staple strands may be targeted individually for attaching different components.

A variety of different components can be attached to a surface of a nucleic acid container and/or a nanoparticle as described herein. In some embodiments, the component comprises a binding site. Sometimes, a component can comprise two binding sites—one for the nanoparticle and one for a target separate from the nanoparticle. The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of biological molecules including proteins, peptides, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, aptamer/protein, etc. Such molecules are examples of components that can be used with the nanoparticles and nucleic acid containers described herein.

In some embodiments, the binding site comprises a nucleic acid. For example, the nucleic acid may be in the form of DNA, RNA, other nucleic acids, or combinations thereof, as described in more detail herein. In some embodiments, the nucleic acid comprises a single stranded portion. In other embodiments, the nucleic acid comprises a double stranded portion. Combinations of single and double stranded portions are also possible. Examples of nucleic acids are provided in more detail below.

In certain embodiments, a component comprises a marker. Examples of markers include readout (or detectable) markers such as luminescent probes, fluorophores or fluorophore labeled molecules or compounds, chromophores or chromophore labeled molecules or compounds, and the like. In some cases, the marker comprises a nanoparticle (e.g., a quantum dot). In certain embodiments, the marker comprises a reporter molecule, such as a surface-enhanced Raman scattering (SERS) reporter molecule.

In some embodiments, a marker and a corresponding binding site are attached to the surface of the nanoparticle and/or nucleic acid container. The marker/binding site pair may be specific and unique for a target molecule, as described in more detail below. In some such embodiments, each marker may be used to represent a specific binding site. In some cases, the nanoparticle and/or nucleic acid container comprises a plurality of marker/binding site pairs, wherein each of the marker/binding site pairs is different from one another, thereby allowing multiplexing. Other combinations of marker and binding sites are also possible.

In some embodiments, the positioning of components at particular orientations with respect to the nucleic acid container and/or nanoparticle surface allows controlled self-assembly of multiple nanostructures into higher-ordered assemblies. For example, as shown in the embodiment illustrated in FIG. 5, assembly 75 includes a plurality of nanostructures 40A-40D that are positioned relative to one another in specific arrangements. The specific arrangements of nanostructures relative to one another may be obtained by using unique components that are placed at specific positions on the nucleic acid container and/or nanoparticle. For example, a nanostructure 40A may be assembled with a nanostructure 40B using components 60A and 60B, which are attached to nanostructures 40A and 40B, respectively. Components 60A and 60B may, in some embodiments, be binding sites that are complimentary to one another such that they selectively bind to one another and not to other components such as components 61A, 61B, 62A, or 62B. As described herein, the components may be designed to include a suitable length, to be positioned at a suitable distance from a surface of the coated nanoparticle, and/or to be positioned on a particular side of the nucleic acid container and/or nanoparticle. Similarly, a nanostructure 40B may be assembled with a nanostructure 40C using a pair of components 61A and 61B, and nanostructure 40B may be assembled with a nanostructure 40D using a pair of components 62A and 62B. As shown in this exemplary embodiment, each surface of the nanostructures can be tagged with different binding sites, allowing the attachment of different nanostructures at each distinct surface within a three-dimensional space.

As described herein, each nanostructure (including a nucleic acid container and/or nanoparticle) used in an assembly may have any suitable shape. For example, as shown illustratively in FIG. 5, nanostructure 40A may be in the form of a rhomboid, nanostructure 40B may be in the form of a pentagon, nanostructure 40C may be in the form of a rhomboid having a different orientation with respect to nanostructure 40A, and nanostructure 40D may be in the form of a hexagon. Other shapes may be used in other embodiments. Additionally, it should be appreciated that any suitable materials may be used in each of the nanostructures. For instance, nanoparticles 38A-38D may be formed of the same materials, or different materials, such as those described herein. Additionally, components 60-62 may vary, and may be components of the same type or of different types.

Figure 5:
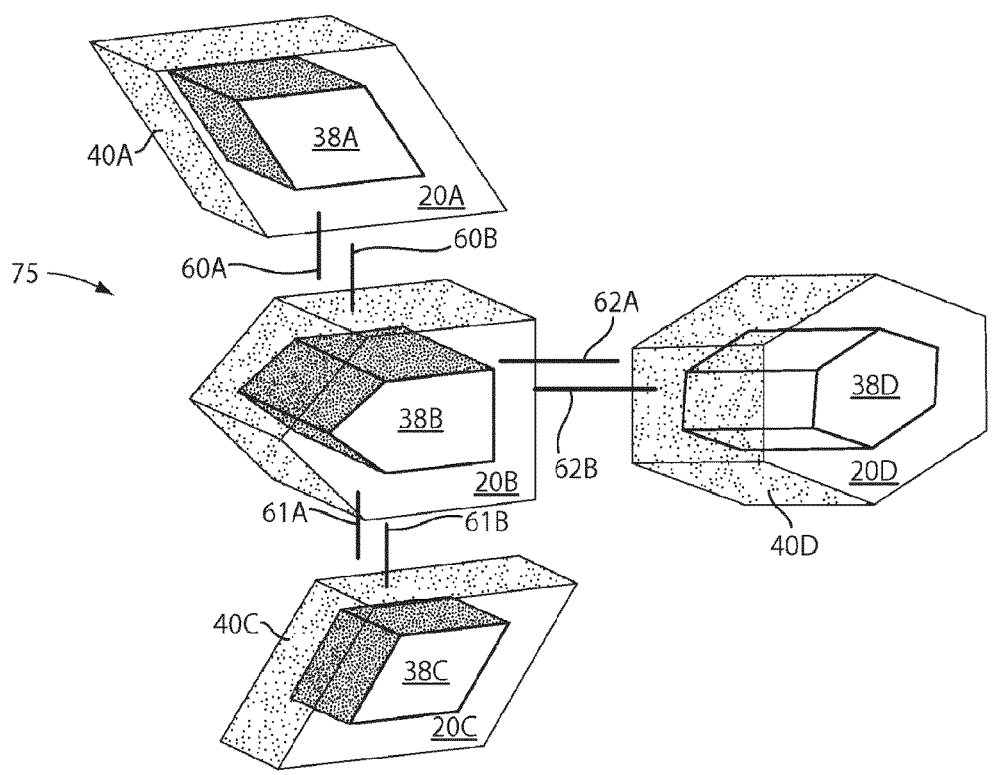
FIG. 5 shows an example of surface-specific self-assembly of nanostructures according to one set of embodiments.

In some embodiments, an assembly such as the one shown in FIG. 5 can be formed by synthesizing a plurality of nucleic acid-coated nanoparticles, each of the nucleic-acid coated nanoparticles formed by growing a nanoparticle from a nanoparticle precursor positioned inside a nucleic acid container, and then assembling the nucleic acid-coated nanoparticles. In other embodiments, a higher order structure can be formed by assembling nucleic acid containers, each of the nucleic acid containers having a nanoparticle precursor positioned therein, and then synthesizing the nanoparticle from the nanoparticle precursor inside the nucleic acid container to form the nucleic acid-coated nanoparticles. A combination of such methods is also possible.

As described herein, any suitable component or binding site may be used for assembly, and the component or binding site may be associated with the nanoparticle and/or the nucleic acid portion of the nanostructure. In some embodiments, the nucleic acid-coated nanoparticles are attached to one another by components or binding sites that are attached to a nucleic acid portion of the nucleic acid-coated nanoparticles. In other embodiments, the nucleic acid-coated nanoparticles are attached to one another by components or binding sites that are attached to a nanoparticle portion of the nucleic acid-coated nanoparticles. In some cases, the nucleic acid-coated nanoparticles are attached to one another using a thermal process (e.g., using heat to cause attachment or binding between two nanoparticles, or two or more components associated with the nanoparticles). In other cases, the nucleic acid-coated nanoparticles are attached to one another using a photophysical process. In certain cases, the nucleic acid-coated nanoparticles are attached to one another using a binding process.

After assembly, all or portions of the nucleic acid container may be optionally removed from the nucleic acid-coated nanoparticles. In some such embodiments, a surface of the nanoparticle may be passivated prior to, during, or after the removal step. The nanoparticles may remain attached to one another in the assembly after the removal step. In other embodiments, the nucleic acid container is not removed after assembly of multiple nanostructures.

Different types of assemblies can be formed. In some cases, the assembly comprises an electronic circuit. In some embodiments, the assembly is in the form of a two-dimensional array. In other embodiments, the assembly is in the form of a three-dimensional array. In some cases, nanostructures can be assembled hierarchically based on surface-specific binding.

Figure 6A:
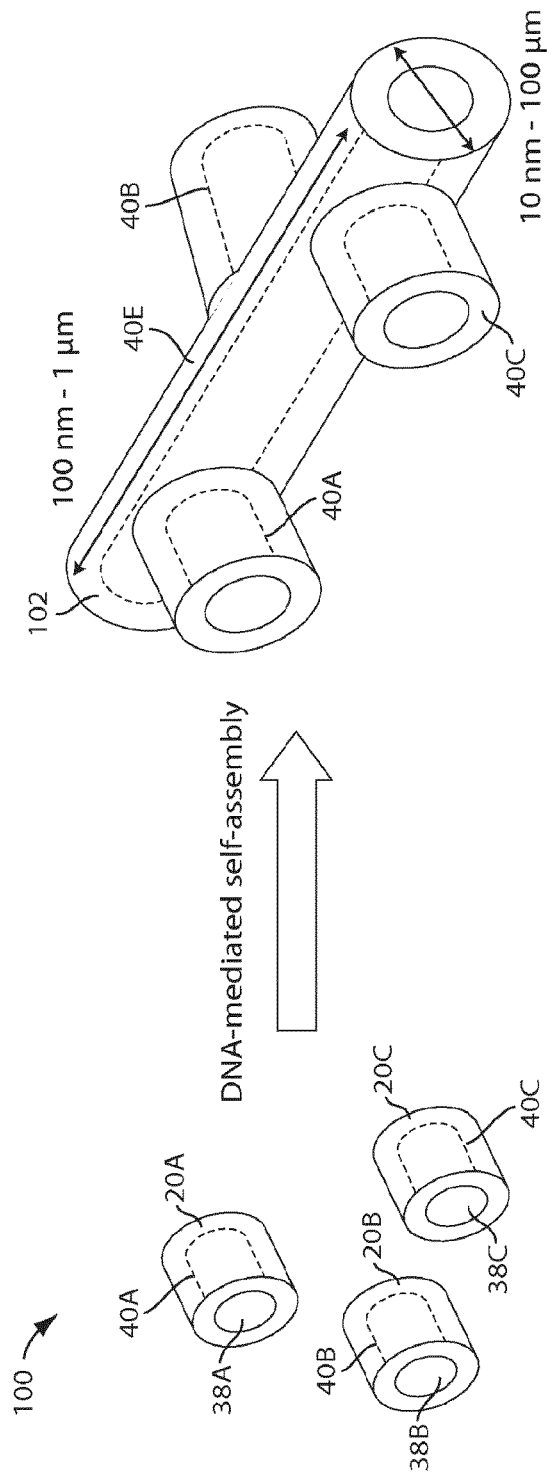
FIGS. 6A and 6B shows self-assembly of nanostructures into an electronic circuit according to one set of embodiments.
Figure 6B:
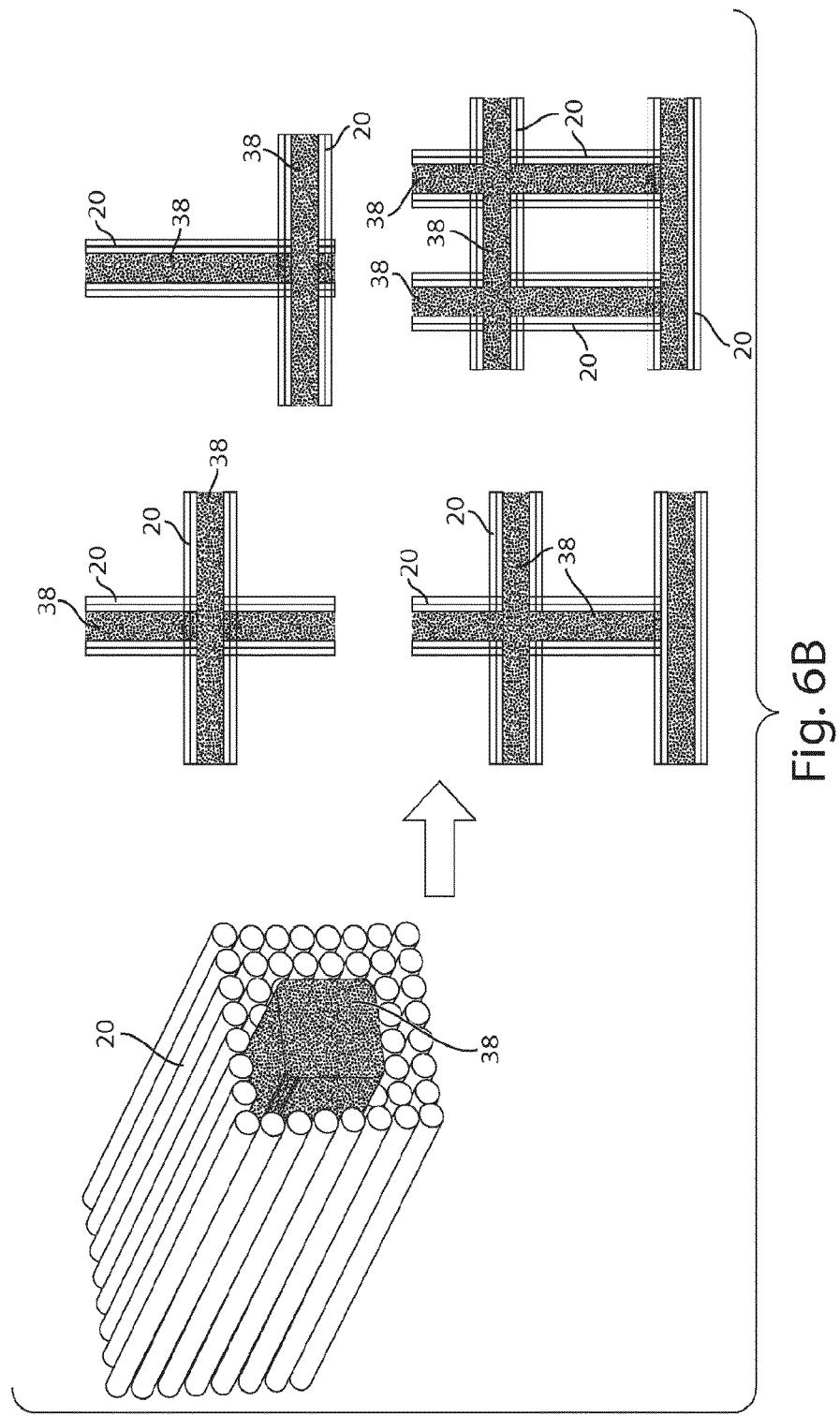

An example of a process for forming a circuit is shown in the embodiments illustrated in FIGS. 6A and 6B. FIG. 6A shows a process 100 including the assembly of nanostructures 40A, 40B, and 40C with a nanostructure 40E to form an electronic circuit. FIG. 6B shows a different orientation of structures in the form of nanorods, which include conductive nanoparticles 38, that can be used to form an electronic circuit. As shown illustratively in the figures, a plurality of nanostructures can be used as building blocks to be placed at designated positions, in some embodiments due to the specificity of binding between different surfaces, as described herein. For example, in FIG. 6B, the linkage points between the structures can be specifically arranged at designed position on nanorods. Also as described herein, different strategies can be utilized to form different structures. For example, in one embodiment an assembly can be formed by assembling nucleic acid containers, and then triggering the growth of a conductive material within the container. In another embodiment, a conductive material can be grown in each of the building blocks using nucleic acid containers, and then the resulting nanostructures can be assembled into a larger structure. In some cases, merging of the ends of the building blocks, e.g., via thermal/photophysical methods, may produce continuous conductive networks that can be used as electronic circuits.

An assembly may have any suitable size and may be on the nano-, micro-, meso- or macro-scale. In some cases, an assembly has a length and/or at least one cross-sectional dimension that is less than or equal to 1 mm, less than or equal to 100 microns, less than or equal to 50 microns, less than or equal to 10 microns, less than or equal to 1 micron, less than or equal to 500 nm, less than or equal to 100 nm, less than or equal to 50 nm, less than or equal to 10 nm, or less than or equal to 1 nm. In other cases, the assembly has a length and/or at least one cross-sectional dimension that is greater than or equal to 1 nm, greater than or equal to 10 nm, greater than or equal to 100 nm, greater than or equal to 1 micron, greater than or equal to 10 microns, greater than or equal to 50 microns, greater than or equal to 100 microns, or greater than or equal to 1 mm. Other values are also possible. Combinations of the above-noted ranges are also possible. A length may of the assembly may be determined by measuring the distance between two outermost portions of furthest-spaced apart nanostructures forming the assembly. Similarly, a cross-sectional dimension of the assembly may be determined by taking a cross-section between two outermost portions of nanostructures forming the assembly and measuring the distance between the outermost portions.

An assembly of nanostructures may have any suitable configuration. For example, in some embodiments, an assembly may have a linear shape (e.g., AAAAAABBBBBBB, where A and B are different nanostructure building blocks, or an alternative chain such as ABABABAB). In other cases, an assembly may have a star shape (e.g., five B around one A). In other embodiments, an assembly may form a three-dimensional structure such as a tube, box, barrel, rectangle, rod, "T", "L", branched structure, diamond, square, parallelogram, rhomboid, triangle, pentagon, hexagon, or polyhedron, including shapes substantially similar thereto. Other configurations are also possible.

Figure 7:
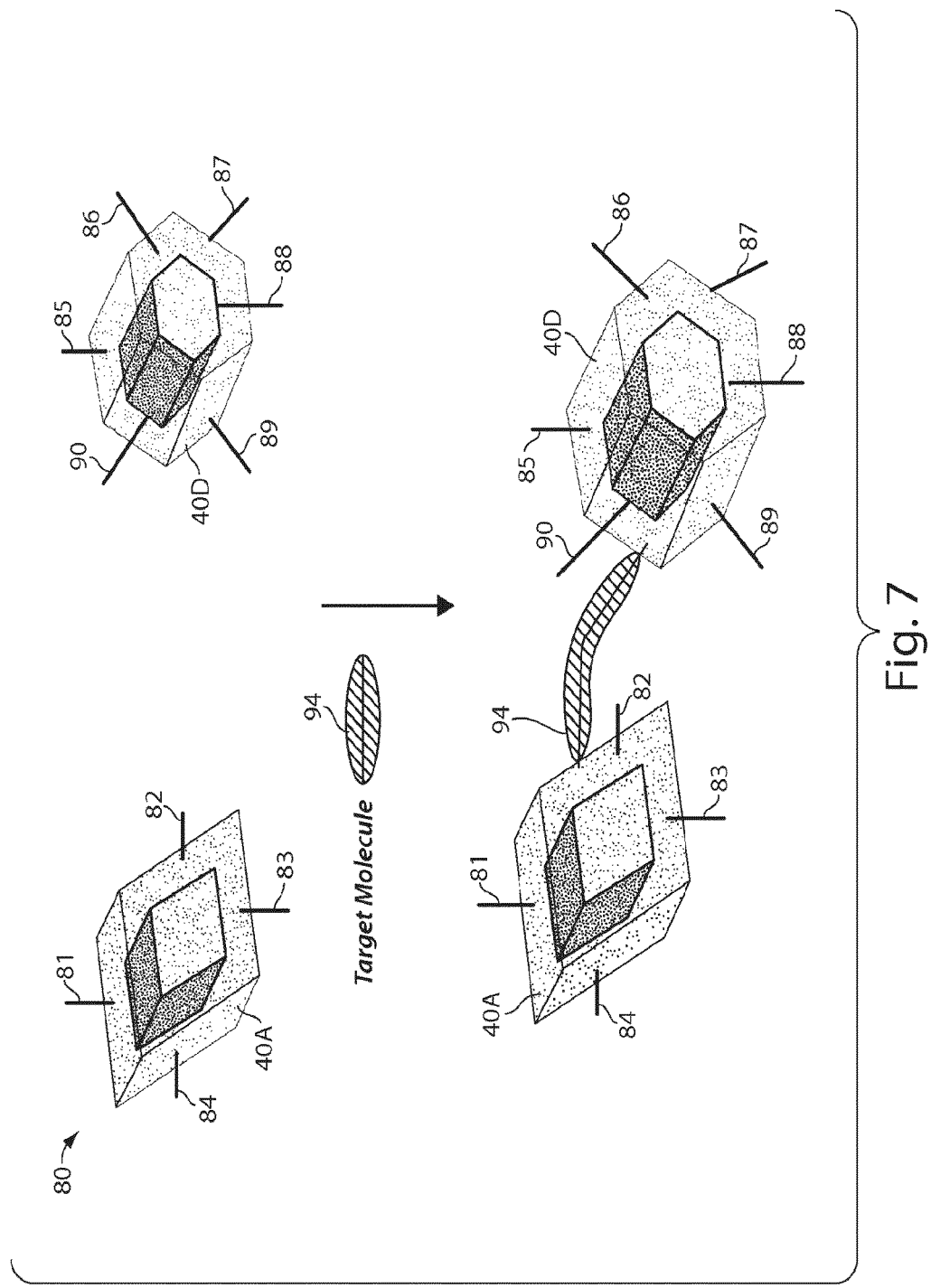
FIG. 7 shows a scheme of target-triggered self-assembly of nanostructures that can be used for surface enhanced Raman spectroscopy detection according to one set of embodiments.

In some embodiments, the nanostructures described herein (e.g., nanoparticles coated or uncoated by a nucleic acid container) can be used for multiplexed detection. Detection may involve, in some embodiments, introducing a composition suspected of comprising a target molecule (e.g., a biomolecule) to a plurality of nanostructures, and allowing the target molecule, if present, to bind to surfaces of at least two different nanostructures. An example of such a method is shown illustratively in FIG. 7. A process 80 involves the use of nanostructures 40A and nanostructure 40D, which include different components attached to different portions/sides of the nanostructure. For example, nanostructure 40A includes components 81-84 positioned on different sides of the nanostructure, and nanostructure 40D includes different components 85-90 positioned on different sides of the nanostructure. In some cases, each of the components of the nanostructure are different from one another, although in other cases, some of the components of the nanostructure may be the same while others may be different from one another. Upon introduction of a target molecule 94, binding between a portion of the target molecule and one of the components of 40A may occur, and binding between a portion of the target molecule and a component of structure 40D may occur. Depending on the particular binding site included in the target molecule, different combinations of binding between components of nanostructures 40A and 40D may occur. As shown illustratively in FIG. 7, the target molecule may include a binding site that is specific to component 82 of nanostructure 40A and a binding site that is specific to component 90 of nanostructure 40D. Using such a method, every two surfaces (e.g., one surface from one nanostructure and another surface from a different nanostructure) may be used to detect one specific target molecule.

In some embodiments, the introduction of a target molecule can trigger the recognition of two specific surfaces, and a unique signal as a result of the recognition event may be produced and/or enhanced. For example, in one set of embodiments, each of the components shown in FIG. 7 may be reporter molecules for SERS-based detection. The binding between the target molecule and two specific surfaces, one on each different nanostructure, can enhance the Raman signals from the two specific reporter molecules associated with the binding. Using such a method, a variety of different target molecules can be detected using relatively few numbers of nanostructures because the signal from the binding of each target molecule will be unique and distinguishable from others.

In some embodiments, the number of different target molecules that can be recognized by nanostructures described herein may depend, at least in part, on the number of different components (e.g., binding sites) positioned on the nanostructure. As described herein, in some cases the components are in the form of isolated components. Generally, the number of different target molecules that can be recognized using the nanostructures described herein can be determined using the formula $(n*x-1)*n*x/2$ (assuming detection of each target molecule involves binding with two nanostructures), where n is the number of nanostructures and x is the number of different binding sites (and/or sides) associated with each of the nanostructures. For example, 2 nanostructures having 5 binding sites on each nanostructure can result in the detection of $(2*5-1)*2*5/2=45$ different target molecules. The number of different target molecules that can be recognized using the nanostructures described herein, assuming detection of each target molecule involves binding with three nanostructures, can be determined using the formula $(n*x-2)*(n*x-1)*n*x/3$. In some embodiments two nanostructures (or 3, 4, 5, 6, etc. nanostructures) can be used to detect, for example, between 2 and 2,000 different target molecules (e.g., between 2 and 1,000, between 2 and 500, between 2 and 200, between 2 and 100, or between 2 and 50 different target molecules). For instance, in some embodiments two nanostructures (or 3, 4, 5, 6, etc. nanostructures) can be used to detect at least 5, at least 10, at least 20, at least 30, at least 40, at least 50, at least 70, at least one 100, at least 500, at least 1,000, or at least 1,500 different target molecules. In some cases, such numbers of target molecules can be detected in parallel. In some embodiments, a composition includes at least 2, at least 3, at least 5, at least 10, at least 20, at least 30, at least 50, or at least 100 different nanostructures, each of which can be used to detect different target molecules.

It should be appreciated that other methods of detection other than SERS-based detection can be used using the nanostructures described herein. For example, other metal-surface-enhanced luminescent probes can be used, wherein the luminescent group is utilized to replace Raman signal reporters.

Nucleic acids, in the context of the invention, include DNA and RNA, as well are various modifications thereof. Modifications include base modifications, sugar modifications, and backbone modifications. Non-limiting examples of these are provided herein. Non-limiting examples of DNA variants that may be used include L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that the nucleic acids used in the embodiments described herein may be homogeneous or heterogeneous in nature. As an example, they may be completely DNA in nature or they may be comprised of DNA and non-DNA (e.g., LNA) monomers or sequences. Thus, any combination of nucleic acid elements may be used. The nucleic acids described herein may be referred to as polymers or nucleic acid polymers. The modification may render the interactions of such polymers more or less stable under certain conditions.

The nucleic acids described herein may be obtained from natural sources, and optionally subsequently modified. They may be synthesized in vitro, and optionally may mimic a naturally occurring nucleic acid or may represent a non-naturally occurring nucleic acid (e.g., due to the present of elements that are not found in naturally occurring nucleic acids). Methods for harvesting nucleic acids from in cells, tissues or organisms are known in the art. Methods for synthesizing nucleic acids, including automated nucleic acid synthesis, are also known in the art.

The nucleic acids may have a homogenous backbone (e.g., entirely phosphodiester or entirely phosphorothioate) or a heterogeneous (or chimeric) backbone. Phosphorothioate backbone modifications render a nucleic acid less susceptible to nucleases and thus more stable (as compared to a native phosphodiester backbone nucleic acid) under certain conditions. Other linkages that may provide more stability to a nucleic acid include without limitation phosphorodithioate linkages, methylphosphonate linkages, methylphosphorothioate linkages, boranophosphonate linkages, peptide linkages, alkyl linkages, dephospho type linkages, and the like.

Nucleic acids having modified backbones, such as backbones comprising phosphorothioate linkages, and including those comprising chimeric modified backbones may be synthesized using automated techniques employing either phosphoramidate or H-phosphonate chemistries. (F. E. Eckstein, "Oligonucleotides and Analogues—A Practical Approach" *IRL Press*, Oxford, UK, 1991, and M. D. Matteucci and M. H. Caruthers, *Tetrahedron Lett.* 21, 719 (1980)) Aryl- and alkyl-phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

The nucleic acids described herein may additionally or alternatively comprise modifications in their sugars. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—($C_1$-$C_6$)alkyl-ribose, preferably 2'-O—($C_1$-$C_6$)alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'—$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

The nucleic acids may comprise modifications in their bases. Modified based include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide).

As used herein, the terms "bind" or "interact" as they relate to nucleic acids typically refer to hybridization (e.g., base-specific binding) between two or more nucleic acid sequences or strands. The term "annealing" refers to the process of heating and slowly cooling a mixture of nucleic acids (e.g., in a typical thermal cycling machine) such that the thermodynamic steady state (or one relatively near it) of hybridized elements is formed. Interaction between nucleic acids, according to certain embodiments described herein, is specific and is typically governed by the sequence of the interacting strands. These interactions include Watson-Crick binding in which complementary nucleic acid sequences hybridize to each other. These interactions may also include other binding motifs including but not limited to Hoogsteen or quadruplex binding.

It should be appreciated that other components such as small molecules, proteins, and markers may be attached to the nucleic acids described herein in some embodiments.

The following examples are intended to illustrate certain embodiments of the present invention, but are not to be construed as limiting and do not exemplify the full scope of the invention.

EXAMPLE 1

This example shows a method for forming gold nanoparticles in nucleic acid containers as described herein.

Step 1: Formation of nucleic acid containers. A nucleic acid container was formed by folding DNA using a DNA origami method. The nucleic acid container was designed using caDNAno software. To fold the DNA strands into the designed shape, 16.7 uL 200 nM M13 nucleic acid scaffold (P8064 mutation) (SEQ. ID. NO. 1), 20 uL 500 nM staple strand (obtained following the procedure described in Dietz et al., *Science*, 325:725-730, 7 Aug. 2009 and Douglas et al., *Nature*, 459: 414-418, 21 May 2009), 11 uL folding buffer (50 mM Tris, 10 mM EDTA, and 120 mM $MgCl_2$), and 44 uL water were mixed. The resulting solution was rapidly heat denatured, followed by slow cooling from 80 to 61 degrees Celsius over 100 min, then from 60 to 24 degrees Celsius over 72 h. The nucleic acid containers were purified on a 2% agarose gel (0.5×TBE+10 mM $MgCl_2$) at 70 V for 3 h in an ice-water bath. The gel was stained with Sybr Gold and the nucleic acid containers were extracted from the gel with crash-soak method.

Step 2: Seed decoration. 5 nm mono-DNA functionalized gold nanoparticle precursors were used as seeds for the growth of a templated nanoparticle. To introduce a seed into the cavity of a nucleic acid container, the purified containers (2 nM in 0.5×TBE+10 mM $MgCl_2$ buffer) were mixed with 50 nM 5 nm mono-DNA functionalized gold nanoparticles. The solution was incubated at 37 degree for 16 hours, and then slowly annealed to 24 degree (1 degree/step, 20 min/step). In order to include a single gold nanoparticle into the cavity of the nucleic acid container, the mono-DNA from the gold nanoparticle was designed to hybridize with a single complementary DNA sequence attached to inner surface of the nucleic acid container.

Excessive unbound gold nanoparticles were removed via spin centrifuge. 20 uL of the seed-decorated nucleic acid container solution was mixed with 180 uL water, and loaded into an Amicon centrifugal filter (MWCO=100 kDa, from Millipore) to be centrifuged at 14,000 g for 3 min. This step was repeated twice under the same conditions. The filter was then reversed, and spun at 1,000 g for 2 min. The residual solution was collected.

Figure 8A:
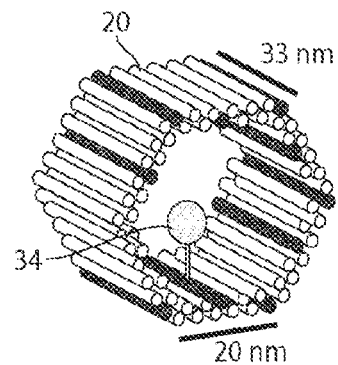
FIG. 8A shows detachment of a nanoparticle precursor into a cavity of a nucleic acid container according to one set of embodiments.

Step 3: Growth of a gold nanoparticle within a nucleic acid container. To grow a gold nanoparticle having a cross-section in the shape of a hexagon, steps 1 and 2 above were first performed to synthesize nucleic acid container 20 including a cavity having a cross-section in the shape of a hexagon, as shown in FIG. 8A. Then, a 10 uL purified seed-decorated solution was combined with a 1 uL 14 mM $HAuCl_4$ precursor solution. 1 uL 20 mM ascorbic acid was added subsequently. After 2 min, 3.5 uL of the final solution was dipped onto a copper grid. After 2 min, the solution was wiped away with filter paper, leaving the nanostructures on the grid. 3.5 uL of a 2% uranium formation was then added onto the grid to stain the resulting nanostructures. After 45 sec, the solution was wiped away with filter paper. The grid was then left for drying in order to dry the resulting nanostructures.

Figure 8B:
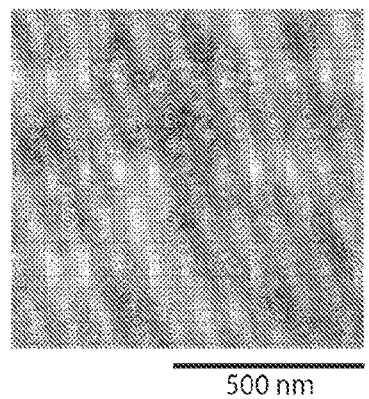
FIG. 8B is a transmission electron microscopy (TEM) image of nucleic acid containers depicted in FIG. 8A according to one set of embodiments.
Figure 8C:
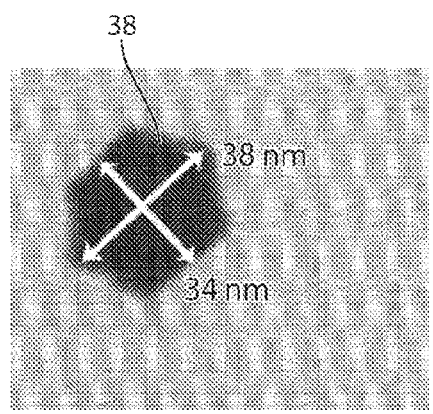
FIG. 8C is a transmission electron microscopy image of a gold nanoparticle that has been formed by templated synthesis inside the nucleic acid containers shown in FIG. 8B according to one set of embodiments.

FIGS. 8B and 8C show TEM images of the resulting nanostructures after purification. As shown in FIG. 8C, a nanoparticle 38 formed of gold had cross-sectional dimensions of 38 nm and 34 nm.

This example shows that gold nanoparticles can be formed in nucleic acid containers that act as a template during the growth of the nanoparticles. The resulting nanoparticles have shapes that are complementary to the shapes of the cavities of the nucleic acid containers.

EXAMPLE 2

This example shows a method for forming silver nanoparticles in nucleic acid containers as described herein.

Figure 9A:
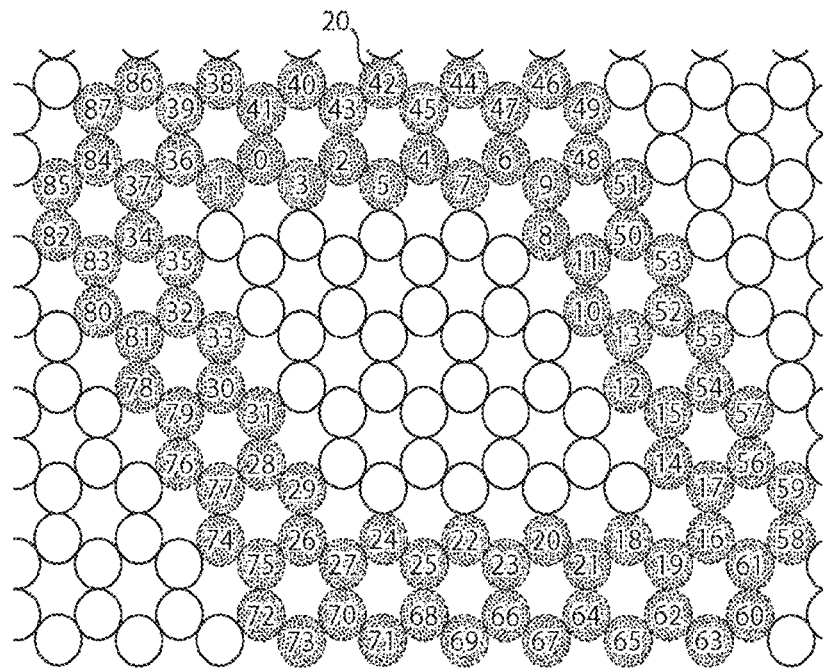
FIG. 9A shows a cross-sectional view of a nucleic acid container according to one set of embodiments.

Steps 1 and 2 described in Example 1 were performed to synthesize a nucleic acid container having a cross-section in the shape of a rhomboid, as shown in FIG. 9A. To grow a silver nanoparticle in the cavity of the nucleic acid container, a 10 uL purified seed-decorated solution was combined with 1 uL 100 mM $Mg(Ac)_2$ solution. To this mixture, 1 uL 14 mM $AgNO_3$ and 1 uL 20 mM ascorbic acid were added subsequently. 3.5 uL of the resulting solution was dipped onto a copper grid. After 2 min, the solution was wiped away with filter paper, leaving the nanostructures on the grid. 3.5 uL 2% uranium formation was then added onto the grid to stain the resulting nanostructures. After 45 sec, the solution was wiped away with filter paper. The grid was then left for drying in order to dry the resulting nanostructures.

Figure 9B:
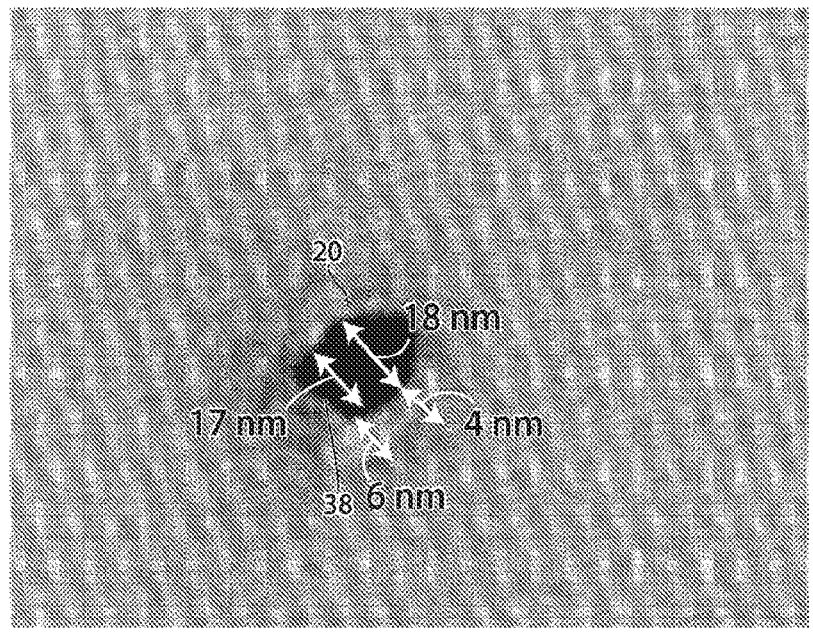
FIG. 9B is a transmission electron microscopy image of a single nanoparticle formed by templated synthesis within the nucleic acid container shown in FIG. 9A.
Figure 9C:
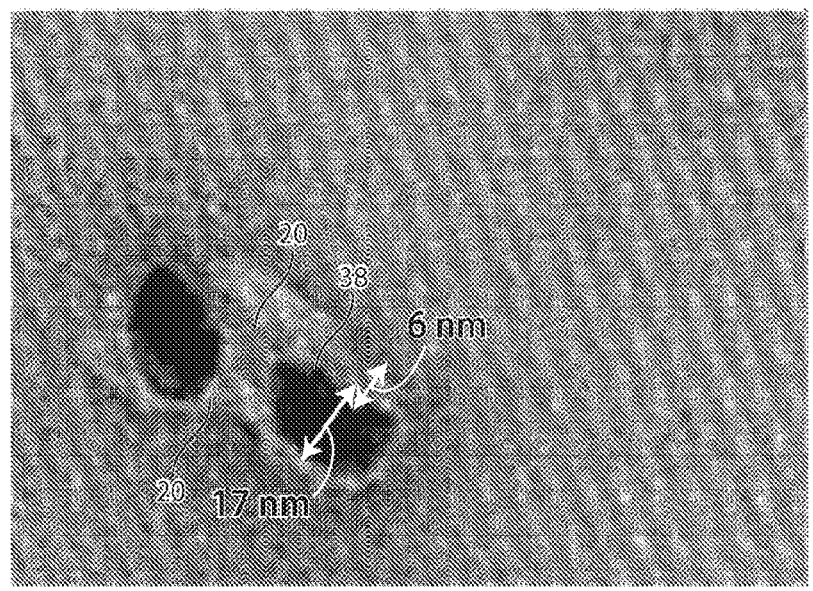
FIGS. 9C and 9D are transmission electron microscopy images showing two nanoparticles formed by dimerized nucleic acid containers according to another set of embodiments.
Figure 9D:
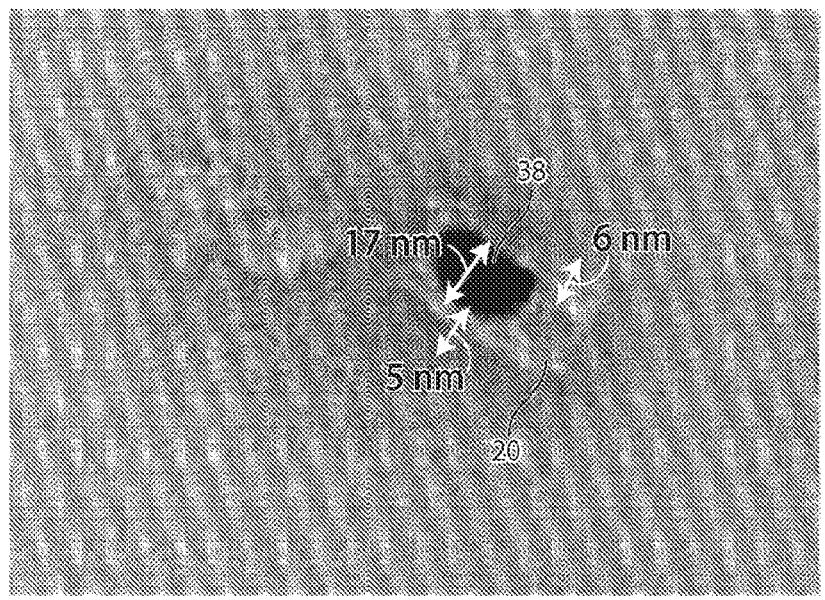

FIGS. 9B-9D show TEM images of the resulting nanostructures after purification. As shown in FIG. 9B, a nanoparticle 38 formed of silver had cross-sectional dimensions of 17 nm and 18 nm. The thickness of the walls of nucleic acid container 20 was approximately 4-6 nm. FIGS. 9C and 9D show two nanostructures that are dimerized. The dimerized structure was formed using Steps 1 and 2 described in Example 1. Prior to growing the silver nanoparticles in the cavities of the nucleic acid containers, however, two nucleic acid containers were attached to one another using complementary DNA strands.

This example shows that silver nanoparticles can be formed in nucleic acid containers that act as a template during the growth of the nanoparticles. The resulting nanoparticles have shapes that are complementary to the shapes of the cavities of the nucleic acid containers. This example also shows that nucleic acid containers can be attached to one another to form larger nanostructures.

EXAMPLE 3

This example shows a method for forming silver nanoparticles in a nucleic acid container having quantum dots associated with the inner surface of the container. The quantum dots were used to block the openings of the nucleic acid container.

Steps 1 and 2 as described in Example 2 were performed to synthesize a nucleic acid container having a cross-section in the shape of a rhomboid, as shown in FIG. 9A. To a solution of 20 uL seed-decorated origami solution, a 0.5 uL solution of 2 uM quantum dots (from Invitrogen) was added, and incubated at 35° C. for 16 hours, and then slowly cooled to room temperature for another 2 hours. Seed purification and silver growth were performed following the method described in Example 2.

Figure 10:
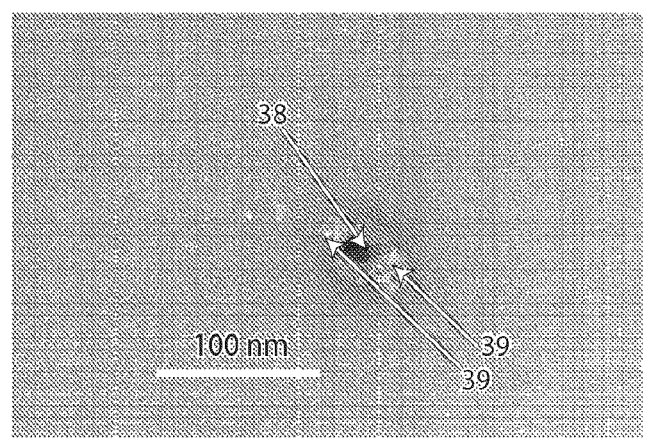
FIG. 10 is a TEM image of a nanoparticle formed inside a cavity of a nucleic acid container that includes two quantum dots associated with the container according to another set of embodiments.

FIG. 10 is a TEM image showing the resulting nanostructure after purification. A nanoparticle 38 made of silver was formed within nucleic acid container 20. Quantum dots 39 were located at the two ends of the nucleic acid container, the quantum dots having dimensions of about 20 nm.

This example shows that a silver nanoparticle can be formed in a nucleic acid container that acts as a template during the growth of the nanoparticle when both ends of the container are blocked by quantum dots. The resulting nanoparticle had a shape that was complementary to the shape of the cavity formed by the nucleic acid container and quantum dots. This example also shows that nucleic acid containers can be utilized to prepare heterogeneous structures, which are potentially applicable in solar cells and hydrogen production from water.

EXAMPLE 4

This example shows a method for designing opened nucleic acid containers and the use of the containers to direct the shape of silver nanoparticles during their formation. In this example, the M13 nucleic acid scaffold (P8064 mutation) (SEQ. ID. NO. 1) was used.

Hollow DNA containers used as molds were designed using a 3D DNA origami strategy as described herein (FIG. 11). To ensure the structural rigidity of nucleic acid (DNA) containers 20, a multi-layered square-lattice design was used to form walls 25 (e.g., sidewalls). A two-layered design made of 16-helix bundles, a three-layered design made of 18-helix bundles, and a four-layered design of 24-helix bundles were tested in different shaped DNA containers (11). The cross-section of cavities 30 of the containers were designed with distinct shapes of sub-25 nm, including rectangular, square, triangle, and ring shapes (FIG. 11A); this distinct property imparts programmability, a feature that existing hard templates lack. The thicknesses of the DNA containers were also tuned from 10 nm to 30 nm. In order to ensure metal growth within the central cavity of a single, defined DNA container, 5-nm gold nanoparticles, used as a seed 34 for silver or gold growth, were conjugated to the interior surface of the DNA container via DNA hybridization (FIG. 11B). A 21-nt single-stranded DNA was immobilized onto a seed surface, and the stoichiometry ratio between gold seeds and surface DNA was 1:1 in the reaction buffer. Multiple 21-nt ssDNAs, ranging from 3 to 25, were immobilized in the interior surface of the DNA containers with sequences complementary to those on the seed surface. Notably, in some embodiments, direct reduction of noble metals, such as silver and gold, without using seeds, may result in the metallization at the exterior surface of the DNA container. Subsequent reduction of metal precursors mediated by the seeds produced confined growth of metal nanostructures 38 within each DNA mold for specific prescribed shapes and dimensions (FIG. 11C).

In this experiment, portions of a DNA container such as DNA barrels and lids were folded by slowly annealing the staple/scaffold mixtures from 80° C. to 24° C. over 72 h. Then, the crude products were subjected to agarose gel electrophoresis (1.5% agarose gel) with 0.5×TBE/10 mM $MgCl_2$ as running buffer. The purified structures were extracted from the gel and then recovered via centrifugation. Seed decoration was executed by the incubation of opened DNA containers (e.g., barrels) with excess of 5-nm gold particles (the stoichiometry ratio between gold and DNA containers ranged from 2:1 to 5:1) at 35 C for 16 h, and then annealed to 24 C over 3 h. Excessive gold nanoparticles were removed by using a size-exclusive spin columns. To form an enclosed cavity, DNA lids were mixed with the seed-decorated DNA barrels at 35 C for 16 h, and then annealed to 24 C over 3 h. Metal precursors, such as silver nitrate for silver nanoparticle and chloroauric acid for the formation of gold nanoparticles, were then added to the purified gold-DNA barrels conjugates, followed by a reducing agent, such as ascorbic acid (AA). After several minutes to hours of growth in the dark at 4 C or room temperature, the solution was dipped onto a copper grid, and stained with uranium salt for TEM imaging.

EXAMPLE 5

This example shows a method for designing closed nucleic acid containers (e.g., boxes) and the use of the containers to direct the shape of silver nanoparticles during their formation. In this example, the M13 nucleic acid scaffold (P8064 mutation) (SEQ. ID. NO. 1) was used.

The three-dimensional confined growth of silver nanoparticles was examined using a box-shaped DNA container. Each DNA box container 20 was designed with three independent components: one barrel 47 and two square shaped lids 50 and 52 (FIG. 12). Cavity 30, surrounded by both the lids and the interior surface of the barrel, was designed with either a square- or rectangular-shaped cross-section. The rectangular DNA barrels were assembled from 88 parallel double helices. The cross-section dimensions of central cavity were designed as 8 helices by 6 helices. The sidewalls were built from both 16-helix bundles and 18-helix bundles. The lengths of the barrels were set as 6 and 9 double-helix turns, respectively. The square-shaped DNA barrel was assembled from 108 double helices. Each sidewall was constructed from 18-helix bundles. The cross-sectional dimensions of the central cavity were designed as 6 helices by 6 helices, with the length of 7 double-helix turns. A three-layered DNA lid was designed with 18 helices in width, 3 helices in thickness and 15 helices turn in length.

Figure 12A:
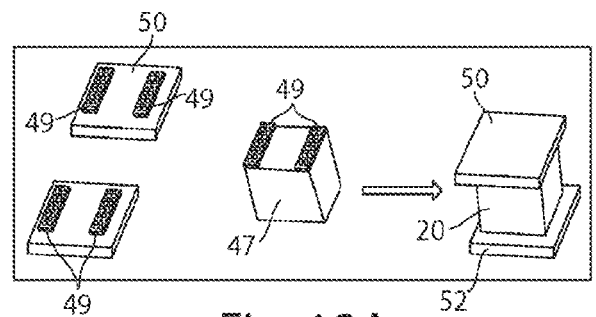
FIGS. 12A-12E are images showing the formation of closed nucleic acid containers and the use of the containers for forming nanoparticles having different shapes according to one set of embodiments.

To connect the lids onto the barrels, 6 or 16 15-nt single-stranded binding sites were introduced at both ends of the 18-helix bundles in the rectangular DNA barrel; while in the square DNA box, 13 15-nt single-stranded binding sites 49 were immobilized at each end of the DNA sidewalls (FIG. 12A). The binding sites at each bundle exhibited the same sequences. On one side of the DNA lids, 20 15-nt single-stranded DNAs with complement sequences to those on DNA barrels were introduced. The spacing between two different sequenced DNA were set to 20 nm, consistent with the spacing of binding sites at the barrels.

For both rectangular barrels and lids, the formation yields were around 10-20%, while for the square barrel, the folding yield was much lower of 5%, owing to barrel dimerization by sticky-end stacking. TEM imaging indicated the formation of the designed shapes. For both rectangular barrels, the cross-sectional dimensions of the central cavity were 20 nm×15 nm, consistent with 2.5 nm per double helix, and 15 nm×15 nm for the square shaped cavity. However, due to partial dehydration and structural deformation during TEM sample preparation for imaging, small deviations of 2 or 3 nm were also observed, as well as corner angle deviations from 90 degrees and/or or rough inner surfaces. TEM imaging also revealed the seed decoration yields for different shaped DNA barrels were approximately 74-91% (N>100).

Figure 12B:
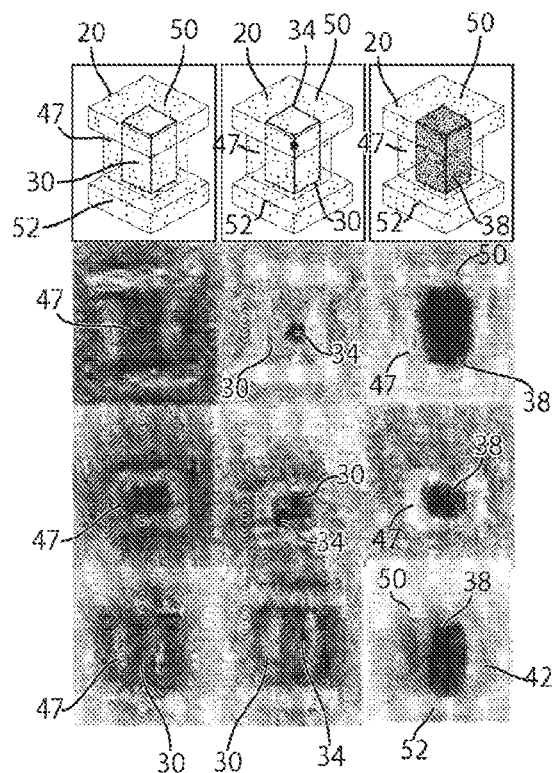
Figure 12C:
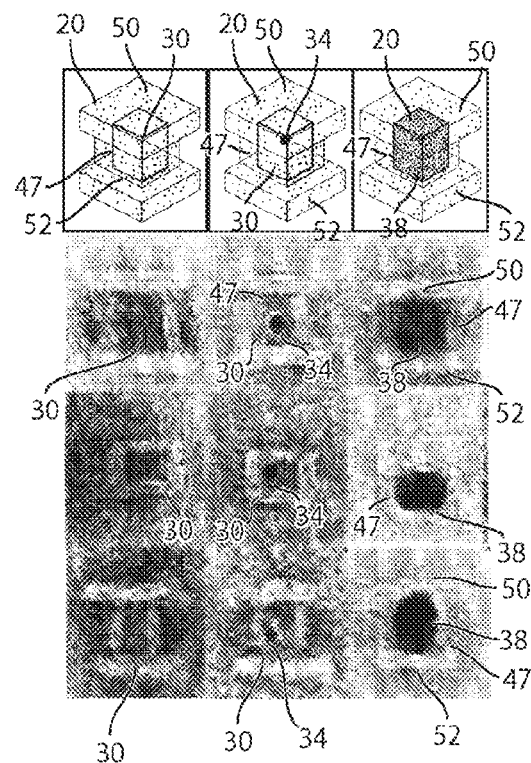
Figure 12D:
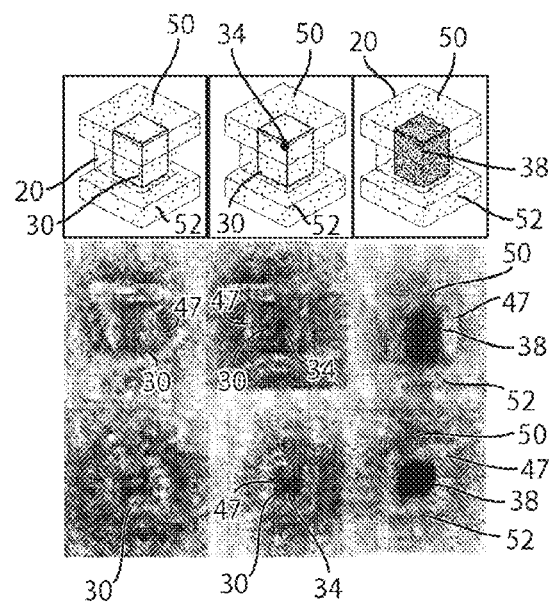

The unpurified reaction solution after lid closure was then imaged with TEM to determine the formation yield (FIGS. 12B-12D left, N>100). A rectangular DNA barrel with 20-15-30 nm dimensions was utilized to optimize the formation yield of the seed-decorated DNA box container. At a lid-to-barrel stoichiometry ratio of 3:1, including 6 binding sites on each end of the rectangular barrel, produced less than 10% box formation yield; whereas increasing the binding sites to 16 promoted the box formation yield to 31% (FIG. 12B, left). Increasing the lids-to-barrel stoichiometry ratio from 2:1 to 6:1 resulted in the slightly increment of box formation yield from 28% to 33%. At a relatively high stoichiometry ratio, i.e., 6:1, in some cases, each end of the barrel may connect to two lids, which may prevent the correct lid closure processes. The yield of defect structures was also increased from 20% in 2:1 stoichiometry ratio to 50% in 6:1 stoichiometry ratio. The formation of defective structures prevented further increments of DNA box formation yield at high stoichiometry ratios. Box closure yields for DNA barrels with 20-15-20 nm dimensions and 15-15-25 dimensions were found to be 13% and 21%, respectively (FIG. 12C-12D left), at a stoichiometry ratio of 3:1. Compared with that of the DNA box container, the formation of seed-decorated DNA box containers was with seed-decorated barrels was further lowered by a factor of around 20%, which was consistent with the formation yields of seed-decorated DNA barrels. Agarose gel electrophoresis was tested to purify the reaction solution of the seed-decorated DNA box containers. However, after the extraction of bands corresponding to the seed-decorated DNA box containers, TEM imaging revealed the presence of both opened and closed seed-decorated DNA box containers, which resulted from either small mobility differences or structural deformation during gel extraction.

The growth of silver nanoparticles was triggered by the addition of silver nitrate (1.4 mM) and ascorbic acid (2 mM). After growth for 4 to 10 min at room temperature, silver nanoparticles 38 grown within the DNA boxes were imaged by TEM (FIG. 12B right). TEM images indicated the presence of 4-8 nm-thick sidewalls after silver growth, which suggested that the DNA containers remained intact after silver growth. In rectangular DNA box containers with 20-15-30 nm dimension cavity, silver nanoparticles were grown into 20-16-30 nm dimension ( 12B, right). Rectangular cross-sections as well as rounded corners were observed in TEM images. When the cavity dimensions were reduced to 20-15-20 nm, silver nanoparticles with similar rectangular cross-shapes and 20-nm thickness were observed (FIG. 12C, right). Different maximum allowed thicknesses of silver nanoparticles in DNA box containers confirmed the confinement of DNA box containers in the thickness direction. Changing the cross-sectional dimensions of the DNA box containers from 20 nm×15 nm to 15 nm×15 nm produced silver nanoparticles with square-shaped cross-sections (FIG. 12D right). Each edge was measured to be around 16 nm in TEM image. The bigger dimensional sizes of the silver nanoparticles, compared with those of cavities, resulted from the compression of the DNA double helices by silver nanoparticle growth.

In some cases, defective DNA structures were also observed during the silver growth processes. In the growth direction confined by two two-layered DNA sidewalls made from 16-helix bundle in a rectangular DNA box container, defective structures were observed with both sidewall bending and cavity expansion; whereas in the growth direction confined by two three-layered DNA sidewalls made from 18-helix bundle, defective structures were mainly observed with expanded dimension size, e.g., from 20 nm to around 25 nm. TEM images indicated that defect yields for two-layered sidewalls was 5 times higher than that in the three-layered sidewalls (N>50). In square shaped DNA box containers with three-layered DNA sidewalls, defective structures mainly resulted from the expansion of cavity dimensions, e.g., from 15 nm to around 20 nm. The defect ratio was also dependent on reaction time and reactant concentration. When the reaction time was 4 min with 0.3 mM AgNO3 and 0.5 mM AA as reactants, the defect ratio at for the square box was decreased by 2/3.

Several other designs for lids and barrels were also tested to fabricate cavities with distinct shapes. 16-helix bundles of DNA with 10 or 15 nm lengths were introduced onto the top of 30-helix bundles. After purification, TEM images indicated the well formation of 30-helix bundles. However, in this particular experiment, both 16-helix bundles did not connect to the 30-helix bundles tightly, and could not be utilized for box formation. DNA barrels with triangular tops was also fabricated. After seed decoration and lid closure, clear spacing was observed at one vertex, which was composed of several 10-nm DNA helices. Although a triangular top was observed in the confined silver nanoparticles, the spacing between 10-nm DNA helices was expanded. This resulted from the unstable linkage of 1 or 2 staple crossovers in 10-nm DNA helices, compared to 4 to 5 staple crossovers linkage in 30-nm DNA helices. The distorted DNA barrels further evidenced that rigid and stable DNA sidewalls confined the metal growth.

Figure 12E:
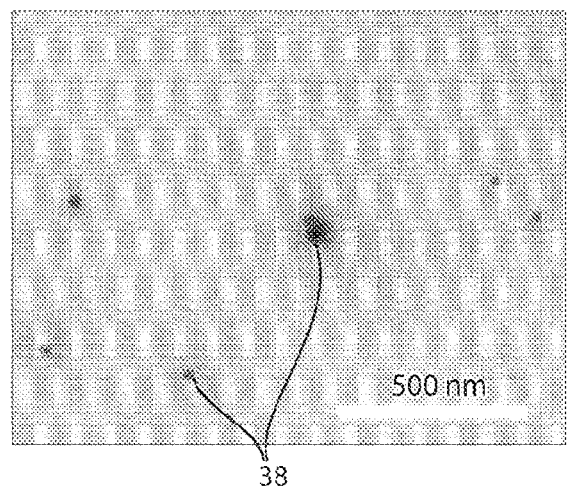

As described herein, FIGS. 12A-12D show confined growth of silver nanoparticles within a DNA box container. FIG. 12B shows design (top) and TEM images (bottom) for silver nanoparticles grown within a rectangular-shaped DNA box of 20-15-30 nm dimensions. From left to right: DNA box, seed-decorated DNA box, and silver growth within the box. FIG. 12C shows design (top) and TEM images (bottom) for silver nanoparticle grown within a rectangular-shaped DNA box of 20-15-20 nm dimensions. From left to right: DNA box, seed-decorated DNA box, and silver growth within the box. FIG. 12D shows design (top) and TEM images (bottom) for silver nanoparticle grown within a square-shaped DNA box of 15-15-25 nm dimensions. From left to right: DNA box, seed-decorated DNA box, and silver growth within the box. FIG. 12E shows zoom-out TEM images for silver nanoparticle grown within the rectangular-shaped DNA box of 20-15-30 nm dimensions.

EXAMPLE 6

This example shows a method for designing opened nucleic acid containers and the use of the containers to direct the shape of silver and gold nanoparticles during their formation. In this example, the M13 nucleic acid scaffold (P8064 mutation) (SEQ. ID. NO. 1) was used.

The generality of the confined growth of metal nanostructures in DNA molds was tested in open nucleic acid containers 20 (e.g., barrels) to demonstrate the cross-section controllability (FIG. 13). Four-layered DNA helices were connected to form walls 25 that encircled specific shaped cavities within the DNA containers. Cavities 30 were designed with three different cross-sectional shapes, e.g., an equilateral triangle (FIG. 13A), a right-angled triangle (FIG. 13B), and disk shapes (FIG. 13C). Three 21-nt single stranded binding sites were introduced at the interior surface of the containers to immobilize seeds 34.

Figure 13A:
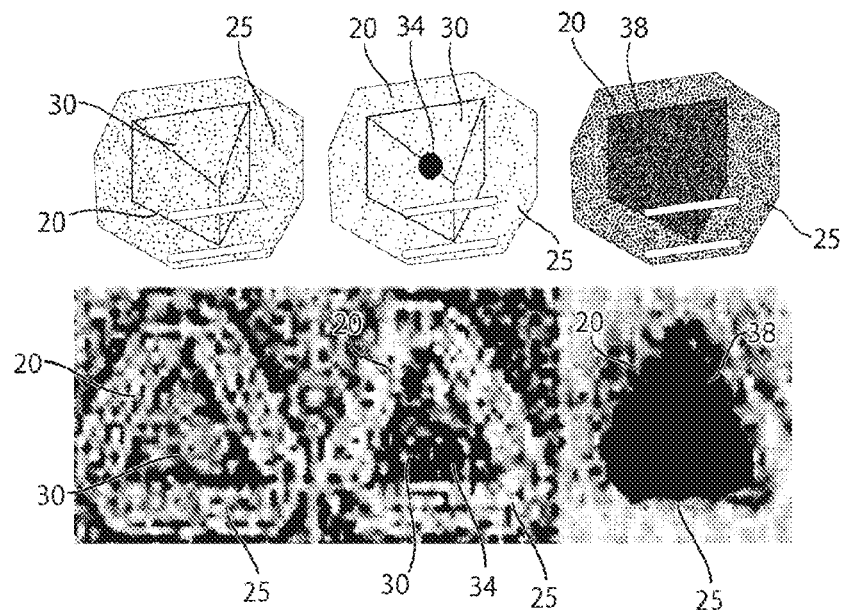
FIGS. 13A-13D are images showing the formation of open nucleic acid containers and the use of the containers for forming nanoparticles having different shapes according to one set of embodiments.
Figure 13B:
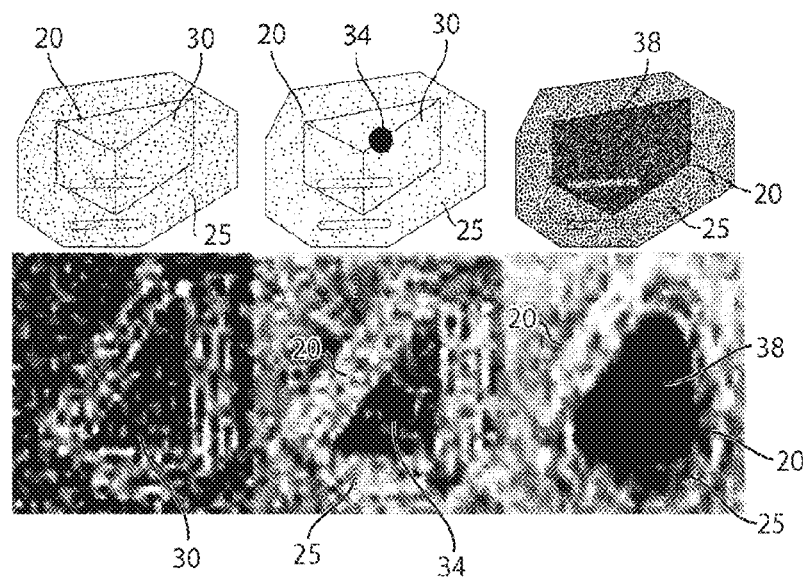
Figure 13C:
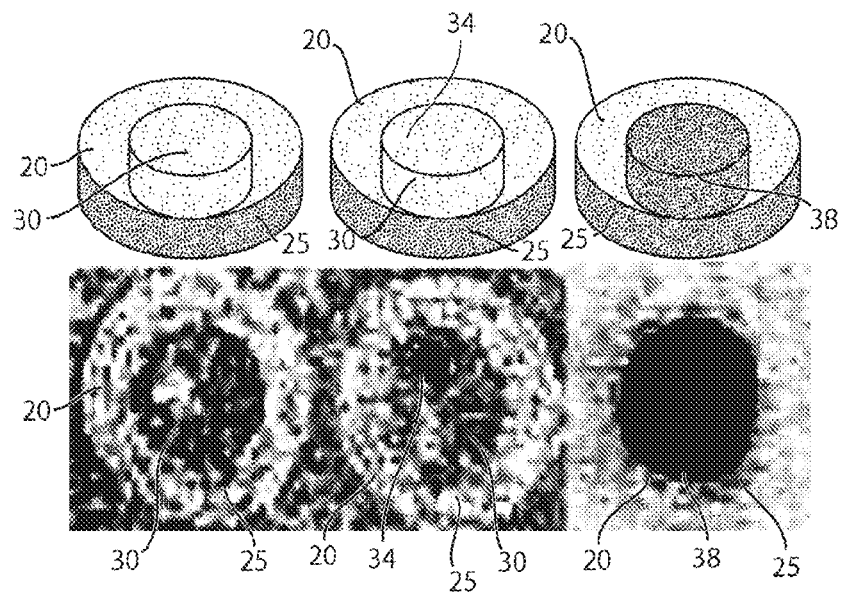

Gel purification indicated 5-10% folding yields of the DNA containers. TEM images showed that the equilateral triangle-shaped DNA channel exhibited an edge length of 25 nm with thickness of 15 nm (FIG. 13A left). In the case of the right-angled triangle, two different sets of edge dimensions, e.g., 20-24-31 nm (FIG. 13B left) and 15-29-33 nm (not shown) have been observed. Shape diversity was ascribed to the presence of 16-base single-stranded regions at the edges of the DNA containers (not shown). At different stretching statuses, single-stranded regions may exhibit distinct lengths, which in turn may produce variable container dimensions. For the DNA ring, the inner diameter of the disk-shaped container was determined to be 25 nm and the thickness was 10 nm (FIG. 13C left). After gold seed decoration, TEM imaging revealed 60-75% decoration yields for each container (N>100). Although multiple binding sites were present at the interior surface of the containers, most DNA containers were conjugated with one seed (FIG. 13A-C middle), which was ascribed to spatial repulsion among nanoparticles within the containers.

The silver nanoparticles grown within the DNA containers (for 4 to 8 min at room temperature) were imaged by TEM. Approximately 5-10% of the silver nanoparticles formed were found to have the shape of the designed cross-sections of the container in which the nanoparticles were grown (the remaining nanoparticles having the shape of spheres). In the equilateral triangle-shaped container, a fully confined silver nanoparticle exhibited an equilateral triangle-shaped cross-section, with each edge having a length of 25 nm and three round vertexes (FIG. 13A right). The DNA container remained intact after silver growth, and was found to be fully wrapped around the side surface of the grown silver nanoparticle. No obvious bending or curvature of DNA sidewalls was observed. In the center of the silver nanoparticle, a round shade with 5-nm diameter was assigned to the decorated gold seed in the DNA container. In the right-angled triangle-shaped channel with 20-24-31 nm dimensions, a right-angled silver nanoparticle was grown with 19-24-29 nm dimensions (FIG. 13B right). Similar with that in the equilateral triangle-shaped channel, round vertexes were also observed in the right-angled silver nanoparticle. In the disk-shaped channel, silver sphere was observed with cross-section diameter of 25 nm (FIG. 13C right).

In the open containers, only particles grown laterally rather than vertically were confined to the shape of the container, which resulted in the 5-10% confinement yields. Most of the unconfined particles exhibited sphere shapes.

It was observed that four-layered DNA helices increased sidewall rigidity. In the case of the equilateral triangle-shaped DNA containers, the number of defective structures having bent sidewalls was lower than those in two- and three-layered rectangular DNA containers. It was also observed that right-angled triangular containers with 15-29-33 nm dimensions also confine the silver growth within. However, the nanoparticle grown in a container having a sharp vertex including a 30-degree angle was not well formed, compared with that formed in a container having angles of 60 degrees in an equilateral triangle, or in a container having an angle of 50 degree in a right-angled triangle.

Several other open containers were also tested. Equilateral triangle-shaped DNA containers with 15-nm edge exhibited less rigid sidewalls compared with that having a 25-nm edge, owing to less staple crossovers to interconnect DNA double helices. The silver nanoparticle grown within produced triangle shaped silver nanoparticles (1%, N>100), but most of the nanostructures were sphere-like. A honeycomb lattice was employed to build hexagonal DNA containers; however, after silver growth, orientation transformation of double helices in the DNA sidewalls were observed, indicating less rigid structure of the honeycomb lattice compared with that of a square lattice.

Figure 13D:
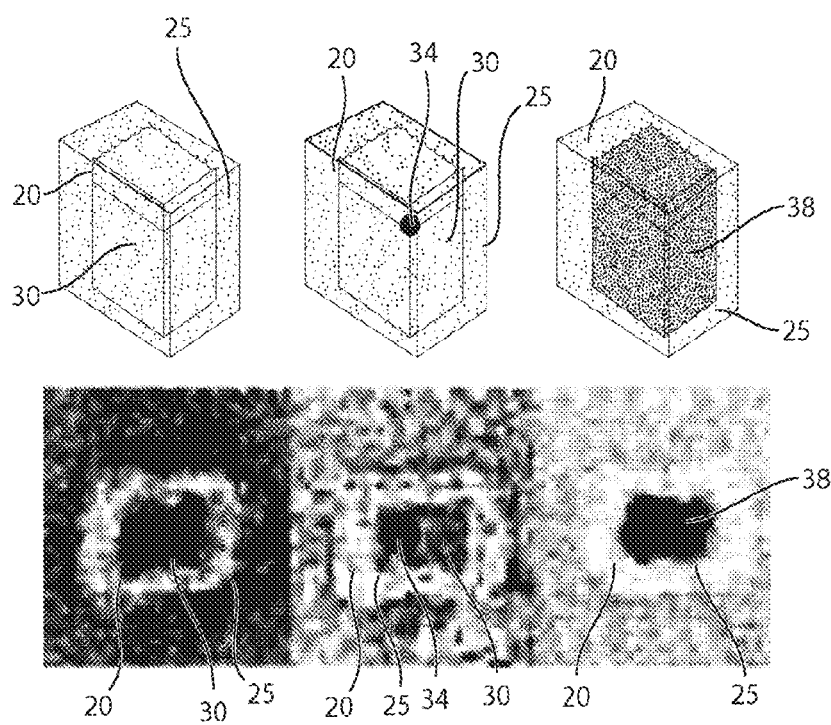

Gold nanoparticles were also grown within open rectangular DNA containers. Compared with that of silver nanoparticles, the growth kinetics of gold in 0.5×TBE/10 mM $Mg(NO3)_2$ buffer was much slower. After reaction for thirty minutes, no obvious size increment had been observed for the nanoparticle within, which was ascribed to the chelating effect of EDTA to the gold precursor. Removing EDTA from the reaction buffer significantly promoted the growth kinetics. Thirty minutes reaction produced a 15 nm×20 nm rectangular cross-shaped gold nanoparticle within the rectangular barrel (FIG. 13D right).

EXAMPLE 7

This example describes a method of performing directed self-assembly of nucleic acid (e.g., DNA) containers as described herein. In this example, the M13 nucleic acid scaffold (P8064 mutation) (SEQ. ID. NO. 1) was used.

DNA containers, including DNA containers containing inorganic nanoparticles, provide not only structural confinement but also surface addressability information. For example, for DNA containers containing nanoparticles therein, due to the sequence specificity of 3D DNA origami, each staple strand (e.g., a DNA strand) that is located near a silver nanoparticle surface can be independently addressed and modulated, which enables a surface addressability resolution down to 2.5 nm×3.4 nm on the nanoparticle surface. Each staple strand can be further modified with distinct binding features, including biotin or multiple different sequenced single-stranded regions, controlled orientations and stoichiometry ratio. Different from previous post-assembly strategies known in the art, surface addressability of DNA nanostructures enabled metal growth within a pre-assembled network of containers. Based on this feature, branched metallic trimers and quantum dot (QD)-silver heterogeneous structures were fabricated, as shown in FIG. 14.

Figure 14A:
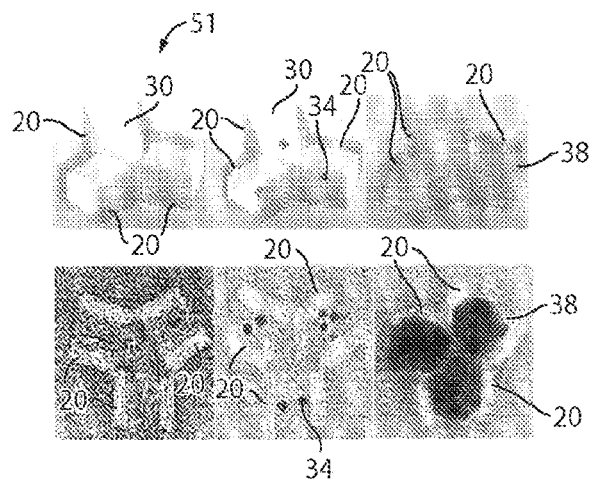
FIG. 14A are images showing the self-assembly of nucleic acid containers to form a larger container used for growing nanoparticles according to one set of embodiments.

To assemble a Y-shaped DNA container 51 from three individual DNA barrel containers 20, six single-stranded connectors were arranged into two parallel rows at one end of each rectangular barrel by the extension of specific staple strands at both 3 and 5 positions. Each row was composed of three different sequenced 15-nt single stranded DNAs, and hybridized to their complementary strands in another partner barrel. Incubation of separately prepared and purified DNA barrels (3 nM) in the presence of 10 nM gold seeds 34 produced seed-decorated Y-shaped barrels. TEM imaging indicated the 5% formation yield of seed-decorated Y-shaped barrels (FIG. 14A, left and middle). Multimers, such as pentamers and hexamers, were also observed in the unpurified solution. Silver growth within the Y-shaped barrel produced individual nanoparticles within each barrel, and a Y-shaped orientation for the trimer, as confined by the orientation of DNA barrel containers (FIG. 14A, right). The widths of silver nanoparticles 38 within each barrel were determined to be 20, 22, and 23 nm. The slightly increased width than the width of the rectangular barrel cavity (20 nm) was attributed to the spacing expansion among DNA double helices by metal growth. In the center of the Y-shape barrel where the growth frontier of silver nanoparticles encountered, three clear particle interfaces were observed, which confirmed that the as-formed silver nanoparticles were originated and assembled from three independent silver fragments. The presence of particle interfaces also indicated the low growth kinetics of different oriented crystallographic facets at the center, owing to the absence of seeds in the center of Y-shaped barrel.

Figure 14B:
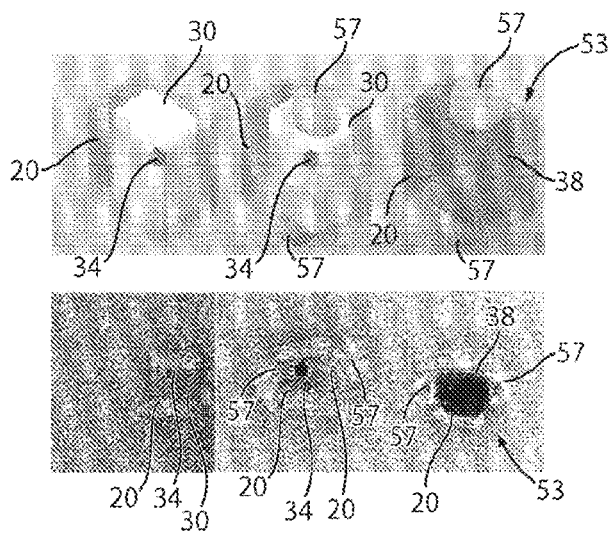
FIG. 14B are images showing the formation of a heterogeneous quantum dot-silver nanoparticle-quantum dot sandwiched structure according to one set of embodiments.

To build a heterogeneous quantum dot (QD)-silver nanoparticle-quantum dot sandwiched structure 53 as shown in FIG. 14B, 5 or 6 biotin groups were introduced at each ends of an open rectangular barrel container 20 with 20-15-30 nm dimensions and having a cavity. The quantum dots were used as lids for the containers to confine the growth of silver nanoparticles within the containers. Biotinylation of DNA container barrels was achieved by the extension of selected staples strands at 5 position via a TT spacer. The biotinylated rectangular barrel container (5 nM) was firstly incubated with gold seeds 34 (10 nM) for 17 hours, and then incubated in the presence of excessive quantum dots 53 (streptavidin-coated QDs (50 nM)) for another 17 hours. Excessive quantum dots 57 and gold seeds were removed via spin column purification. TEM imaging revealed the formation of the designed sandwiched structure between QDs and seed-decorated barrels ((FIG. 14B, left and middle)). After staining, the white spheres with 15-20 nm diameter was attributed to the PEG and streptavidin shell around QD cores. 70% seed-decorated barrels were found conjugated with two QDs at both ends (N>100). Notably, no QD was found attached to the side surface of DNA barrels. Growth mediated by the decorated gold seeds produced silver nanoparticles between two QDs, with designed QD-Ag-QD heterogeneous structures (FIG. 14B, right). The dimension sizes of Ag nanoparticle within DNA barrels were determined to be 21 nm by 30 nm, which was in consistent with the size of cavity of the container.

| NUCLEIC ACID SEQUENCES |
| --- |
| M13 nucleic acid scaffold (P8064 mutation) (SEQ ID NO: 1) |
| GAATTCGAGCTCGGTACCCGGGGATCCTCAACTGTGAGGAGGCTCACGG |
| ACGCGAAGAACAGGCACGCGTGCTGGCAGAAACCCCCGGTATGACCGTG |
| AAAACGGCCCGCCGCATTCTGGCCGCAGCACCACAGAGTGCACAGGCGC |
| GCAGTGACACTGCGCTGGATCGTCTGATGCAGGGGGCACCGGCACCGCT |
| GGCTGCAGGTAACCCGGCATCTGATGCCGTTAACGATTTGCTGAACACA |
| CCAGTGTAAGGGATGTTTATGACGAGCAAAGAAACCTTTACCCATTACC |
| AGCCGCAGGGCAACAGTGACCCGGCTCATACCGCAACCGCGCCCGGCGG |
| ATTGAGTGCGAAAGCGCCTGCAATGACCCCGCTGATGCTGGACACCTCC |
| AGCCGTAAGCTGGTTGCGTGGGATGGCACCACCGACGGTGCTGCCGTTG |
| GCATTCTTGCGGTTGCTGCTGACCAGACCAGCACCACGCTGACGTTCTA |
| CAAGTCCGGCACGTTCCGTTATGAGGATGTGCTCTGGCCGGAGGCTGCC |
| AGCGACGAGACGAAAAAACGGACCGCGTTTGCCGGAACGGCAATCAGCA |
| TCGTTTAACTTTACCCTTCATCACTAAAGGCCGCCTGTGCGGCTTTTTT |
| TACGGGATTTTTTTATGTCGATGTACACAACCGCCCAACTGCTGGCGGC |
| AAATGAGCAGAAATTTAAGTTTGATCCGCTGTTTCTGCGTCTCTTTTTC |
| CGTGAGAGCTATCCCTTCACCACGGAGAAAGTCTATCTCTCACAAATTC |
| CGGGACTGGTAAACATGGCGCTGTACGTTTCGCCGATTGTTTCCGGTGA |
| GGTTATCCGTTCCCGTGGCGGCTCCACCTCTGAAAGCTTGGCACTGGCC |
| GTCGTTTTACAACGTCGTGACTGGGAAAACCCTGGCGTTACCCAACTTA |
| ATCGCCTTGCAGCACATCCCCCTTTCGCCAGCTGGCGTAATAGCGAAGA |
| GGCCCGCACCGATCGCCCTTCCCAACAGTTGCGCAGCCTGAATGGCGAA |
| TGGCGCTTTGCCTGGTTTCCGGCACCAGAAGCGGTGCCGGAAAGCTGGC |
| TGGAGTGCGATCTTCCTGAGGCCGATACTGTCGTCGTCCCCTCAAACTG |
| GCAGATGCACGGTTACGATGCGCCCATCTACACCAACGTGACCTATCCC |
| ATTACGGTCAATCCGCCGTTTGTTCCCACGGAGAATCCGACGGGTTGTT |
| ACTCGCTCACATTTAATGTTGATGAAAGCTGGCTACAGGAAGGCCAGAC |
| GCGAATTATTTTTGATGGCGTTCCTATTGGTTAAAAAATGAGCTGATTT |
| AACAAAAATTTAATGCGAATTTTAACAAAATATTAACGTTTACAATTTA |
| AATATTTGCTTATACAATCTTCCTGTTTTTGGGGCTTTTCTGATTATCA |
| ACCGGGGTACATATGATTGACATGCTAGTTTTACGATTACCGTTCATCG |
| ATTCTCTTGTTTGCTCCAGACTCTCAGGCAATGACCTGATAGCCTTTGT |
| AGATCTCTCAAAAATAGCTACCCTCTCCGGCATTAATTTATCAGCTAGA |
| ACGGTTGAATATCATATTGATGGTGATTTGACTGTCTCCGGCCTTTCTC |
| ACCCTTTTGAATCTTTACCTACACATTACTCAGGCATTGCATTTAAAAT |
| ATATGAGGGTTCTAAAAATTTTTATCCTTGCGTTGAAATAAAGGCTTCT |
| CCCGCAAAAGTATTACAGGGTCATAATGTTTTTGGTACAACCGATTTAG |
| CTTTATGCTCTGAGGCTTTATTGCTTAATTTTGCTAATTCTTTGCCTTG |
| CCTGTATGATTTATTGGATGTTAATGCTACTACTATTAGTAGAATTGAT |
| GCCACCTTTTCAGCTCGCGCCCCAAATGAAAATATAGCTAAACAGGTTA |
| TTGACCATTTGCGAAATGTATCTAATGGTCAAACTAAATCTACTCGTTC |
| GCAGAATTGGGAATCAACTGTTATATGGAATGAAACTTCCAGACACCGT |
| ACTTTAGTTGCATATTTAAAACATGTTGAGCTACAGCATTATATTCAGC |
| AATTAAGCTCTAAGCCATCCGCAAAAATGACCTCTTATCAAAAGGAGCA |
| ATTAAAGGTACTCTCTAATCCTGACCTGTTGGAGTTTGCTTCCGGTCTG |
| GTTCGCTTTGAAGCTCGAATTAAAACGCGATATTTGAAGTCTTTCGGGC |
| TTCCTCTTAATCTTTTTGATGCAATCCGCTTTGCTTCTGACTATAATAG |
| TCAGGGTAAAGACCTGATTTTTGATTTATGGTCATTCTCGTTTTCTGAA |
| CTGTTTAAAGCATTTGAGGGGATTCAATGAATATTTATGACGATTCCG |
| CAGTATTGGACGCTATCCAGTCTAAACATTTTACTATTACCCCCTCTGG |
| CAAAACTTCTTTTGCAAAAGCCTCTCGCTATTTTGGTTTTTATCGTCGT |
| CTGGTAAACGAGGGTTATGATAGTGTTGCTCTTACTATGCCTCGTAATT |
| CCTTTTGGCGTTATGTATCTGCATTAGTTGAATGTGGTATTCCTAAATC |
| TCAACTGATGAATCTTTCTACCTGTAATAATGTTGTTCCGTTAGTTCGT |
| TTTATTAACGTAGATTTTTCTTCCCAACGTCCTGACTGGTATAATGAGC |
| CAGTTCTTAAAATCGCATAAGGTAATTCACAATGATTAAAGTTGAAATT |
| AAACCATCTCAAGCCCAATTTACTACTCGTTCTGGTGTTTCTCGTCAGG |
| GCAAGCCTTATTCACTGAATGAGCAGCTTTGTTACGTTGATTTGGGTAA |
| TGAATATCCGGTTCTTGTCAAGATTACTCTTGATGAAGGTCAGCCAGCC |
| TATGCGCCTGGTCTGTACACCGTTCATCTGTCCTCTTTCAAAGTTGGTC |
| AGTTCGGTTCCCTTATGATTGACCGTCTGCGCCTCGTTCCGGCTAAGTA |
| ACATGGAGCAGGTCGCGGATTTCGACACAATTTATCAGGCGATGATACA |
| AATCTCCGTTGTACTTTGTTTCGCGCTTGGTATAATCGCTGGGGGTCAA |
| AGATGAGTGTTTTAGTGTATTCTTTTGCCTCTTTCGTTTTAGGTTGGTG |
| CCTTCGTAGTGGCATTACGTATTTTACCCGTTTAATGGAAACTTCCTCA |
| TGAAAAAGTCTTTAGTCCTCAAAGCCTCTGTAGCCGTTGCTACCCTCGT |
| TCCGATGCTGTCTTTCGCTGCTGAGGGTGACGATCCCGCAAAAGCGGCC |
| TTTAACTCCCTGCAAGCCTCAGCGACCGAATATATCGGTTATGCGTGGG |
| CGATGGTTGTTGTCATTGTCGGCGCAACTATCGGTATCAAGCTGTTTAA |
| GAAATTCACCTCGAAAGCAAGCTGATAAACCGATACAATTAAAGGCTCC |
| TTTTGGAGCCTTTTTTTTGGAGATTTTCAACGTGAAAAAATTATTATTC |
| GCAATTCCTTTAGTTGTTCCTTTCTATTCTCACTCCGCTGAAACTGTTG |
| AAAGTTGTTTAGCAAAATCCCATACAGAAAATTCATTTACTAACGTCTG |

| NUCLEIC ACID SEQUENCES |
| --- |
| GAAAGACGACAAAACTTTAGATCGTTACGCTAACTATGAGGGCTGTCTG |
| TGGAATGCTACAGGCGTTGTAGTTTGTACTGGTGACGAAACTCAGTGTT |
| ACGGTACATGGGTTCCTATTGGGCTTGCTATCCCTGAAAATGAGGGTGG |
| TGGCTCTGAGGGTGGCGGTTCTGAGGGTGGCGGTTCTGAGGGTGGCGGT |
| ACTAAACCTCCTGAGTACGGTGATACACCTATTCCGGGCTATACTTATA |
| TCAACCCTCTCGACGGCACTTATCCGCCTGGTACTGAGCAAAACCCCGC |
| TAATCCTAATCCTTCTCTTGAGGAGTCTCAGCCTCTTAATACTTTCATG |
| TTTCAGAATAATAGGTTCCGAAATAGGCAGGGGGCATTAACTGTTTATA |
| CGGGCACTGTTACTCAAGGCACTGACCCCGTTAAAACTTATTACCAGTA |
| CACTCCTGTATCATCAAAAGCCATGTATGACGCTTACTGGAACGGTAAA |
| TTCAGAGACTGCGCTTTCCATTCTGGCTTTAATGAGGATTTATTTGTTT |
| GTGAATATCAAGGCCAATCGTCTGACCTGCCTCAACCTCCTGTCAATGC |
| TGGCGGCGGCTCTGGTGGTGGTTCGGTGGCGGCTCTGAGGGTGGTGGC |
| TCTGAGGGTGGCGGTTCTGAGGGTGGCGGCTCTGAGGGAGGCGGTTCCG |
| GTGGTGGCTCTGGTTCCGGTGATTTTGATTATGAAAAGATGGCAAACGC |
| TAATAAGGGGGCTATGACCGAAAATGCCGATGAAAACGCGCTACAGTCT |
| GACGCTAAAGGCAAACTTGATTCTGTCGCTACTGATTACGGTGCTGCTA |
| TCGATGGTTTCATTGGTGACGTTTCCGGCCTTGCTAATGGTAATGGTGC |
| TACTGGTGATTTTGCTGGCTCTAATTCCCAAATGGCTCAAGTCGGTGAC |
| GGTGATAATTCACCTTTAATGAATAATTTCCGTCAATATTTACCTTCCC |
| TCCCTCAATCGGTTGAATGTCGCCCTTTTGTCTTTGGCGCTGGTAAACC |
| ATATGAATTTTCTATTGATTGTGACAAAATAAACTTATTCCGTGGTGTC |
| TTTGCGTTTCTTTTATATGTTGCCACCTTTATGTATGTATTTTCTACGT |
| TTGCTAACATACTGCGTAATAAGGAGTCTTAATCATGCCAGTTCTTTTG |
| GGTATTCCGTTATTATTGCGTTTCCTCGGTTTCCTTCTGGTAACTTTGT |
| TCGGCTATCTGCTTACTTTTCTTAAAAAGGGCTTCGGTAAGATAGCTAT |
| TGCTATTTCATTGTTTCTTGCTCTTATTATTGGGCTTAACTCAATTCTT |
| GTGGGTTATCTCTCTGATATTAGCGCTCAATTACCCTCTGACTTTGTTC |
| AGGGTGTTCAGTTAATTCTCCCGTCTAATGCGCTTCCCTGTTTTTATGT |
| TATTCTCTGTAAAGGCTGCTATTTTCATTTTTGACGTTAAACAAAAA |
| ATCGTTTCTTATTTGGATTGGGATAAATAATATGGCTGTTTATTTTGTA |
| ACTGGCAAATTAGGCTCTGGAAAGACGCTCGTTAGCGTTGGTAAGATTC |
| AGGATAAAATTGTAGCTGGGTGCAAAATAGCAACTAATCTTGATTTAAG |
| GCTTCAAAACCTCCCGCAAGTCGGGAGGTTCGCTAAAACGCCTCGCGTT |
| CTTAGAATACCGGATAAGCCTTCTATATCTGATTTGCTTGCTATTGGGC |
| GCGGTAATGATTCCTACGATGAAAATAAAAACGGCTTGCTTGTTCTCGA |
| TGAGTGCGGTACTTGGTTTAATACCCGTTCTTGGAATGATAAGGAAAGA |
| CAGCCGATTATTGATTGGTTTCTACATGCTCGTAAATTAGGATGGGATA |

| NUCLEIC ACID SEQUENCES |
| --- |
| TTATTTTTCTTGTTCAGGACTTATCTATTGTTGATAAACAGGCGCGTTC |
| TGCATTAGCTGAACATGTTGTTTATTGTCGTCGTCTGGACAGAATTACT |
| TTACCTTTTGTCGGTACTTTATATTCTCTTATTACTGGCTCGAAAATGC |
| CTCTGCCTAAATTACATGTTGGCGTTGTAAATATGGCGATTCTCAATT |
| AAGCCCTACTGTTGAGCGTTGGCTTTATACTGGTAAGAATTTGTATAAC |
| GCATATGATACTAAACAGGCTTTTTCTAGTAATTATGATTCCGGTGTTT |
| ATTCTTATTTAACGCCTTATTTATCACACGGTCGGTATTTCAAACCATT |
| AAATTTAGGTCAGAAGATGAAATTAACTAAAATATATTTGAAAAAGTTT |
| TCTCGCGTTCTTTGTCTTGCGATTGGATTTGCATCAGCATTTACATATA |
| GTTATATAACCCAACCTAAGCCGGAGGTTAAAAAGGTAGTCTCTCAGAC |
| CTATGATTTTGATAAATTCACTATTGACTCTTCTCAGCGTCTTAATCTA |
| AGCTATCGCTATGTTTTCAAGGATTCTAAGGGAAAATTAATTAATAGCG |
| ACGATTACAGAAGCAAGGTTATTCACTCACATATATTGATTTATGTAC |
| TGTTTCCATTAAAAAAGGTAATTCAAATGAAATTGTTAAATGTAATTAA |
| TTTTGTTTTCTTGATGTTTGTTTCATCATCTTCTTTTGCTCAGGTAATT |
| GAAATGAATAATTCGCCTCTGCGCGATTTTGTAACTTGGTATTCAAAGC |
| AATCAGGCGAATCCGTTATTGTTTCTCCCGATGTAAAAGGTACTGTTAC |
| TGTATATTCATCTGACGTTAAACCTGAAAATCTACGCAATTTCTTTATT |
| TCTGTTTTACGTGCAAATAATTTTGATATGGTAGGTTCTAACCCTTCCA |
| TTATTCAGAAGTATAATCCAAACAATCAGGATTATATTGATGAATTGCC |
| ATCATCTGATAATCAGGAATATGATGATAATTCCGCTCCTTCTGGTGGT |
| TTCTTTGTTCCGCAAAATGATAATGTTACTCAAACTTTTAAAATTAATA |
| ACGTTCGGGCAAAGGATTTAATACGAGTTGTCGAATTGTTTGTAAAGTC |
| TAATACTTCTAAATCCTCAAATGTATTATCTATTGACGGCTCTAATCTA |
| TTAGTTGTTAGTGCTCCTAAAGATATTTTAGATAACCTTCCTCAATTCC |
| TTTCAACTGTTGATTTGCCAACTGACCAGATATTGATTGAGGGTTTGAT |
| ATTTGAGGTTCAGCAAGGTGATGCTTTAGATTTTTCATTTGCTGCTGGC |
| TCTCAGCGTGGCACTGTTGCAGGCGGTGTTAATACTGACCGCCTCACCT |
| CTGTTTTATCTTCTGCTGGTGGTTCGTTCGGTATTTTTAATGGCGATGT |
| TTTAGGGCTATCAGTTCGCGCATTAAAGACTAATAGCCATTCAAAAATA |
| TTGTCTGTGCCACGTATTCTTACGCTTTCAGGTCAGAAGGGTTCTATCT |
| CTGTTGGCCAGAATGTCCCTTTTATTACTGGTCGTGTGACTGGTGAATC |
| TGCCAATGTAAATAATCCATTTCAGACGATTGAGCGTCAAAATGTAGGT |
| ATTTCCATGAGCGTTTTTCCTGTTGCAATGGCTGGCGGTAATATTGTTC |
| TGGATATTACCAGCAAGGCCGATAGTTTGAGTTCTTCTACTCAGGCAAG |
| TGATGTTATTACTAATCAAAGAAGTATTGCTACAACGGTTAATTTGCGT |
| GATGGACAGACTCTTTTACTCGGTGGCCTCACTGATTATAAAAACACTT |
| CTCAGGATTCTGGCGTACCGTTCCTGTCTAAAATCCCTTTAATCGGCCT |
| CCTGTTTAGCTCCCGCTCTGATTCTAACGAGGAAAGCACGTTATACGTG |

| NUCLEIC ACID SEQUENCES |
|---|
| CTCGTCAAAGCAACCATAGTACGCGCCCTGTAGCGGCGCATTAAGCGCG |
| GCGGGTGTGGTGGTTACGCGCAGCGTGACCGCTACACTTGCCAGCGCCC |
| TAGCGCCCGCTCCTTTCGCTTTCTTCCCTTCCTTTCTCGCCACGTTCGC |
| CGGCTTTCCCCGTCAAGCTCTAAATCGGGGGCTCCCTTTAGGGTTCCGA |
| TTTAGTGCTTTACGGCACCTCGACCCCAAAAAACTTGATTTGGGTGATG |
| GTTCACGTAGTGGGCCATCGCCCTGATAGACGGTTTTTCGCCCTTTGAC |
| GTTGGAGTCCACGTTCTTTAATAGTGGACTCTTGTTCCAAACTGGAACA |
| ACACTCAACCCTATCTCGGGCTATTCTTTTGATTTATAAGGGATTTTGC |
| CGATTTCGGAACCACCATCAAACAGGATTTTCGCCTGCTGGGGCAAACC |
| AGCGTGGACCGCTTGCTGCAACTCTCTCAGGGCCAGGCGGTGAAGGGCA |
| ATCAGCTGTTGCCCGTCTCACTGGTGAAAAGAAAAACCACCCTGGCGCC |
| CAATACGCAAACCGCCTCTCCCCGCGCGTTGGCCGATTCATTAATGCAG |
| CTGGCACGACAGGTTTCCCGACTGGAAAGCGGGCAGTGAGCGCAACGCA |
| ATTAATGTGAGTTAGCTCACTCATTAGGCACCCCAGGCTTTACACTTTA |
| TGCTTCCGGCTCGTATGTTGTGTGGAATTGTGAGCGGATAACAATTTCA |
| CACAGGAAACAGCTATGACCATGATTAC |

| Sequences of staple strands for the DNA container in FIG. 8. |
|---|
| oligo1 (SEQ ID NO: 2)<br>TAACCACCCACTACGTGAACCACGTCAAAGGGCGAACCGCCT |
| oligo2 (SEQ ID NO: 3)<br>CGGGCGCAGGTGCCGTAAAGCCAGTTTGGAACAAGGTTTGCC |
| oligo3 (SEQ ID NO: 4)<br>CGGCGAACGATTTAGAGCTTGATAAATCAAAAGAAAAATCGG |
| oligo4 (SEQ ID NO: 5)<br>GTTTTTTATTAAAGAACGTGTGCAGCAAGCGGTCTGGGCGC |
| oligo5 (SEQ ID NO: 6)<br>CTAAAGGAGATAGGGTTGAGTTCCTGTTTGATGGTTTAATGA |
| oligo6 (SEQ ID NO: 7)<br>AAAGTTGTTCACTAAATGAAAGCGTTAGAATCAGAGCGAATCAGT |
| oligo7 (SEQ ID NO: 8)<br>TTCAGAGAGTGACTCCAATCACCCGGTCACGACTATGG |
| oligo8 (SEQ ID NO: 9)<br>CAGGGTGAAAGTGTAAAGCCTTTTTCACGGTCATCGTGTGTT |
| oligo9 (SEQ ID NO: 10)<br>ATCGGCCATTAATTGCGTTGCCCTGTGCACTCTGTCTGCAGC |
| oligo10 (SEQ ID NO: 11)<br>CGAGCCGTTTCCTGTGTGAAATCATAAACATCCCTGCCCTGC |
| oligo11 (SEQ ID NO: 12)<br>TGCTGCGTATCACGCTGAGTCCACGGGGTCGTAGGGCGACGTATA |
| oligo12 (SEQ ID NO: 13)<br>GTGAGCTCGGCCAGAATGCGGCGGCATCAGATGCCCAATCCG |
| oligo13 (SEQ ID NO: 14)<br>ACTAGCTGCAGGTTCCGTAGCCCGGAGCCCCCGTGGCGAACAGGA |
| oligo14 (SEQ ID NO: 15)<br>CAGCAAAGGTATGAGCCGGGTGGTCTGGTCAGCAGGTCTCGT |
| oligo 15 (SEQ ID NO: 16)<br>CAGCGGTCATTGCAGGCGCTTGTCGGTGGTGCCATACGATGC |
| oligo16 (SEQ ID NO: 17)<br>GGCTGGTGTAGAACGTCAGCGGGCCAGAGCACATCGCGGATCTCAC |
| oligo17 (SEQ ID NO: 18)<br>CCGGGCGAAGAATGCCAACGGGCAAACGCGGTCCGGGGCGGTATTT |
| oligo18 (SEQ ID NO: 19)<br>ACCTCGCACTGGGTTACGGTGCTGAACTCACAACGCGCGCGA |
| oligo19 (SEQ ID NO: 20)<br>TCCTGGTGCTCACTGTTTACACTGATAGCTGGAAGCATGTTT |
| oligo20 (SEQ ID NO: 21)<br>CGCTGGCGCTCATTTCCGTGGGTTTTCCCTTCGCTTGCC |
| oligo21 (SEQ ID NO: 22)<br>TGATTGCTAAAAAAGCCATGTGCTTTCATCAGGCTTCGC |
| oligo22 (SEQ ID NO: 23)<br>AGCAGTTTTTTTTCCAACCGCCGGTTGCTCGTTAACGGGCCGGGGG |
| oligo23 (SEQ ID NO: 24)<br>AAAAAAAAAGTTAACCCACGCGCGGGGTGCCGGTGCTGCGCGGCTC |
| oligo24 (SEQ ID NO: 25)<br>GGAATTAAGTCGAAAGGGGCGCATGGGATAGATTGTAAGAAGATTCAAT |
| oligo25 (SEQ ID NO: 26)<br>GTGTAAAACGAAGGGCGACAGTATCGTCGGATGTTAAACATATGTAGAG |
| oligo26 (SEQ ID NO: 27)<br>TCGACGGGAAAGGCAAAGGCACCGTAGCCAGAAATAATAAGAGAACATT |
| oligo27 (SEQ ID NO: 28)<br>CGCCAGGTGAAGGGATAGCTCAAACTTAAATTTCTAGCC |
| oligo28 (SEQ ID NO: 29)<br>GTGCCAATTACCAGTCCCGGATGTGTACATCGACACGTTCCGCAGC |
| oligo29 (SEQ ID NO: 30)<br>AGTAAACGGCTTAAAATTCAGAAATAGCTGAAAAGATTTAAA |

NUCLEIC ACID SEQUENCES oligo30 (SEQ ID NO: 31)
ACTAAATGTGAACCAATTCGTAAAGATCTACCCCTCATATTA oligo31 (SEQ ID NO: 32)
GCTTTCCGCGCCATTCGCCATGAGGTGG oligo32 (SEQ ID NO: 33)
CCGTAATCGTAACCGTGCATCATTACGCCAGCTGGTGGGTAA oligo33 (SEQ ID NO: 34)
TGGGAACTTGAGGGGACGACGATCGGTGCGGGCCTCAGTCAC oligo34 (SEQ ID NO: 35)
AACAACCCGGCCTCAGGAAGAGCGCAACTGTTGGGACGGCCA oligo35 (SEQ ID NO: 36)
ACGGTAAAGGAACGCCATCAACTTTCATCAACATTCCAGCCA oligo36 (SEQ ID NO: 37)
ATGCCGGACCCCGGTTGATAATCGCATTAAATTTTTTCTCCG oligo37 (SEQ ID NO: 38)
TAAGCAACAAAAGGGTGAGAAATATTCAACCGTTCAGCCCCA oligo38 (SEQ ID NO: 39)
GCCAAAGGTGGCATCAAACATGTTTTAAATACCTTTAA oligo39 (SEQ ID NO: 40)
CAAAAACATATTTTAAATGCAAGCTATTTTTGAGAACTAGCA oligo40 (SEQ ID NO: 41)
TGAAATAACCTGTTTAGTCATTCCATATAACCCAGACC oligo41 (SEQ ID NO: 42)
ATACTTTAAAAATTTTTAGAAAAAGGCTATCAGGTTCGATGA oligo42 (SEQ ID NO: 43)
GTAGCATTGAATATAATGCTGAAGAGGTCATTTTTAGAAAAC oligo43 (SEQ ID NO: 44)
TGATCAGAGCATAAAGCAGTAATGTGTAGGTTAAATTA oligo44 (SEQ ID NO: 45)
GGGGCGCAAAGTACGGTGTCTACAGGTCAGGATTACTGACTA oligo45 (SEQ ID NO: 46)
TTTCGCATCCCAATTCTGCGATAATTCGAGCTTCAATTAAGA oligo46 (SEQ ID NO: 47)
TTGCTCCATCAAAAATCAGGTAATACTGCGGAATCATGCAGA oligo47 (SEQ ID NO: 48)
GGAAGCAAAAGCGGATTGCATCCAGAGGGGGTAATGAGCAAC oligo48 (SEQ ID NO: 49)
TTGCAAAAGAAGCGAAAGTTGATAATGGTCCCCTGTA oligo49 (SEQ ID NO: 50)
ACCACATAACATTATTACAGGCAAATCAACGTAACTCAAGAG oligo50 (SEQ ID NO: 51)
CTAGTCATAAACCATAATTTTGATTAGCTCATTCTACTGCAAAAT oligo51 (SEQ ID NO: 52)
TACATAAAATAAAACGAACTACTCATTCAGTGAATGCATAGG oligo52 (SEQ ID NO: 53)
ACGAGGCTTGGGAAGAAAAATGCCCTGACGAGAAATGAACGG oligo53 (SEQ ID NO: 54)
TAAAGTAAAACAGAAGCAACTCCAGGAAGTTCTATATTGTTGTAC oligo54 (SEQ ID NO: 55)
ACTATCACTCATTATACCAGTACGAGTAGTAAATTCCAACTT oligo55 (SEQ ID NO: 56)
CAGACGATTATGCGATTTTAAAGATGGTTTAATTTATCATAA oligo56 (SEQ ID NO: 57)
AAAGCGAGAGCGAAAGACGCGTTTACGAGTAGACCATTGAAGCCT oligo57 (SEQ ID NO: 58)
GTTCGCCAAAAGCGTCCCTTTACCGAGAGTATGCAACTGAGC oligo58 (SEQ ID NO: 59)
TAATCTTCCCAGCGATTATACAGAGGCAAAAGAATATAACCGCAAT oligo59 (SEQ ID NO: 60)
CTGGCTGGAAACAAAGTACAAAAGGCACCAACCTATGAG oligo60 (SEQ ID NO: 61)
TGTACAGTTGTATCATCGCCTAAAATACGTAATGCGGCCGCTAGGT oligo61 (SEQ ID NO: 62)
TGAAAGATGTGTCGAAATCCGGGAAGTTTCCATTAACCC oligo62 (SEQ ID NO: 63)
GGGAACCCTCCATGTTACTTAGGACTAAAGACTTTCATCGGAAAAA oligo63 (SEQ ID NO: 64)
TGACGACCTGGAACTGAGGGCTTGGAACTGGTAACCCTAGTT oligo64 (SEQ ID NO: 65)
CGGTCGCAAACGAACAAGCGCACCTTCAAAAGCTGACGGAACTCAA oligo65 (SEQ ID NO: 66)
GCTTGATACCTGCTAAATAGCGTAGTTTAGTGGATAAGTACT oligo66 (SEQ ID NO: 67)
AGTTAAACACTACGCGGAGATACCAGGCAAGGCTTCTAC oligo67 (SEQ ID NO: 68)
GATCGTCAACGGGTGATAAATGGACAGACACCAGACAGGACGATAG

NUCLEIC ACID SEQUENCES oligo68
(SEQ ID NO: 69)
TCACGGTTTAAGGAACAAAACTACCACCCTCAGAGAAGGTGC oligo69
(SEQ ID NO: 70)
TAGCAACGCTTTGAGCCGGAAACGGTCACAACTTTAATTACCCGAT oligo70
(SEQ ID NO: 71)
GACTGAATTTTGTCGTCGTGTATCTTGATATGCTTTTGACCGTTCACCA oligo71
(SEQ ID NO: 72)
GAATTCAGCGTCCACAGAACCGCCGGGTTTTGGGTCAGATCCTCACTCA oligo72
(SEQ ID NO: 73)
GGAGAATAATACTGAGTCATTTTCTTAAGAGGCCCCCTAGGCAGGACCA oligo73
(SEQ ID NO: 74)
GAATTGCGCCTTTAATTGTATGCAGCGAAAGACAGTTCA oligo74
(SEQ ID NO: 75)
TCATAGTCAACTTTCAACAGTTTTCTTAAACAGCTTGCAGGG oligo75
(SEQ ID NO: 76)
GAGAGGGACCGTACTCAGGAGACGATCTAAAGTTTTCTGTAT oligo76
(SEQ ID NO: 77)
ATTAGCGACCCTCAGAACCGCAACGCCTGTAGCATGAGTGAG oligo77
(SEQ ID NO: 78)
CTCCTCAAGAGCCACCACCCTTTCGTCACCAGTACACTAAAG oligo78
(SEQ ID NO: 79)
GAAAGTAAGGGATAGCAAGCCCCATGTACCGTAACAATTTTT oligo79
(SEQ ID NO: 80)
GGTGAAAGCGGCCTCCCCCCCCTTCCATTTGGGGAGGG oligo80
(SEQ ID NO: 81)
TTTAACGGCTCAGTACCAGGCACCGCCACCCTCAGACAGCCC oligo81
(SEQ ID NO: 82)
CCGTTGATATGCCACCACGTCAGATACCATTTTACCAG oligo82
(SEQ ID NO: 83)
AGCCGCCTCAGACGATTGGCCTATAAACAGTTAATGCTGAGA oligo83
(SEQ ID NO: 84)
GTCATAGTCAGAGCCGCCACCTTAAAGCCAGAATGAATAAGT oligo84
(SEQ ID NO: 85)
ACTTGAGATTAGCGTTTGCCACCACCACCGGAACCCAGTCTC oligo85
(SEQ ID NO: 86)
GCACCATCTGTAGCGCGTTTTCCGCCACCCTCAGATCACAAA oligo86
(SEQ ID NO: 87)
CCATCGAGTAATCAGTAGCGACCACCACCAGAGCCTTGACAG oligo87
(SEQ ID NO: 88)
TATTCATTAATAACGGAATACCCGAACAAAGTTACTCAAAAA oligo88
(SEQ ID NO: 89)
AAGGTAAAACTGGCATGATTATTAAGAAAAGTAAGTTTACAG oligo89
(SEQ ID NO: 90)
ATTCAACTTATTACGCAGTATGCTATCTTACCGAAAAACAGG oligo90
(SEQ ID NO: 91)
CGCCAAAAACGTAGAAAATACAGAAACAATGAAATGGGAGAA oligo91
(SEQ ID NO: 92)
GGTAGCAAGGCCGGAAAAAGTTTGCCTTTAGCCCTCAG oligo92
(SEQ ID NO: 93)
AAAATTCAAGGTGGCAACATATTAAGCCCAATAATTGAACAA oligo93
(SEQ ID NO: 94)
TTTAGACTCCCGATTGAGGAATTAGAGCCAGATTTTCG oligo94
(SEQ ID NO: 95)
AGAGAATAAAATAAACAGCCACAAATCAGATATAGAACCAAG oligo95
(SEQ ID NO: 96)
TTAACTGAACGCTAACGAGCGAGGCGTTTTAGCGAATAATCG oligo96
(SEQ ID NO: 97)
CGCCCAAAGAACAAGCAAGCCAGAGAATATAAAGTCATGTAA oligo97
(SEQ ID NO: 98)
AAGTATTATTAGCAGCCCAGATAGCCAAAAGATATTGAGTCACCG oligo98
(SEQ ID NO: 99)
ATTCTAATCATTCCAAGAACGAGACGACGACAATACAGTAGG oligo99
(SEQ ID NO: 100)
GCGTCTTTCCATTAGACAGCAATAGTTAGCAGACAAAAACCAGTA oligo100
(SEQ ID NO: 101)
GGGAGGTCGAGCATGTAGAAAGCCTGTTTATCAACATGCGTT oligo101
(SEQ ID NO: 102)
AAGCAGCTACGGGTAATAATTGAGTAAAAGAGTCACAAAATGAAA oligo102
(SEQ ID NO: 103)
TACCGCAAAAGGTAAAGTAATCGCCATATTTAACATAGTTAA oligo103
(SEQ ID NO: 104)
GCTGTCTTGTTCAGCTAATGCCAGTATAAAGCCAAACCGACC oligo104
(SEQ ID NO: 105)
TCAACCTCCCTCTTACCAACACCCAAGAGCAATACATAATAT oligo105
(SEQ ID NO: 106)
TTTAGGCAAAACTTTTTCAAATGCTGATGCAAATCATTA

| NUCLEIC ACID SEQUENCES |
|---|
| oligo106 (SEQ ID NO: 107)<br>AATTCTGTCCGGTATTAAAGGCTTCAGTTACAACATAAGCCC |
| oligo107 (SEQ ID NO: 108)<br>GCTTAATCTAAATTTAATGGTTTTAACCTCCGGCTGAGTGAAAGCA |
| oligo108 (SEQ ID NO: 109)<br>ATACAAAGCGTTAAATAAGAAAATAGTGAATTTATTTTTCCCTACA |
| oligo109 (SEQ ID NO: 110)<br>TTTCATCGGTTATATAACTATAGTACATAAACATCTTGC |
| oligo110 (SEQ ID NO: 111)<br>GTGTGATATAGGTCTGAGAGATAAATCGATTATTCGTTT |
| oligo111 (SEQ ID NO: 112)<br>CCTAATTACAAACCTACTACTTCTTAATAGAAAATATCCGAA |
| oligo112 (SEQ ID NO: 113)<br>TGGAAACATGTAAATATATTTACGCCAAACCGACACTCATCGTAGC |
| oligo113 (SEQ ID NO: 114)<br>GCTTCTGCTACCTTTTGAAATCGCTCAAAACAACATTCCTTAGAAC |
| oligo114 (SEQ ID NO: 115)<br>TAATTAACAAAATCAAATAAGTTCTTACAGAACGCCCAA |
| oligo115 (SEQ ID NO: 116)<br>CCTTGAAAAGAGTCTAAACACGTATCATAATAGATTAATTTATTTG |
| oligo116 (SEQ ID NO: 117)<br>ATGAAACAAATCAATATATGTTAGGTTGTTCTGACTGAG |
| oligo117 (SEQ ID NO: 118)<br>AAAAGAAATTGATGATGAGAAGTATTGGCAAGAACCACCTGA |
| oligo118 (SEQ ID NO: 119)<br>AAACAGTAACCCACCAGATCCTTTGCTGAACTTAACACAGTA |
| oligo119 (SEQ ID NO: 120)<br>ACGTAATCCTAGATAATGGAATTGTCGCCATACGTGGCTGGT |
| oligo120 (SEQ ID NO: 121)<br>AACTCATCATCAATTCGCCTCAATACAGAGGGCCAACAGAAA |
| oligo121 (SEQ ID NO: 122)<br>AGATCATTTTAATTTTAAAAAATCCCACGCTAGATTCATCTG |
| oligo122 (SEQ ID NO: 123)<br>GGAATTAGTCAGATGAATATATCGCGCAGAGGCGATCGCTAT |
| oligo123 (SEQ ID NO: 124)<br>AGGATTTGCAATTCATCAATATAAAACAGAAATAAGAAGATG |
| oligo124 (SEQ ID NO: 125)<br>TTATCTATTAGAGCCGTCAATGATTGTTTGGATTACATATCA |
| oligo125 (SEQ ID NO: 126)<br>TGGTCAGTTAGACTTTACAAAATTCCTGATTATCAGCGTAGA |
| oligo126 (SEQ ID NO: 127)<br>TCACCTTGCCCGAACGTTATTGCGGAACAAAGAAAAGTACCT |
| oligo127 (SEQ ID NO: 128)<br>CTGTGAATGGAACTCAAATAACATGCGCTTAATGCGCC |
| oligo128 (SEQ ID NO: 129)<br>GTCAGTACTCAAATATCAAACACAACTCGTATTAAAAGGAGC |
| oligo129 (SEQ ID NO: 130)<br>TAAGAATTAAAAATACCGAACATCAACAGTTGAAAACATTTG |
| oligo130 (SEQ ID NO: 131)<br>CCTTACCGCCTCACGCAGACGAGCCTGGCAAGTGTAGCAAATCAA |
| oligo131 (SEQ ID NO: 132)<br>ATACTACATTTTTTTATGGAGCTAAGAAAGGAAGGGAACGGAACC |
| oligo132 (SEQ ID NO: 133)<br>GAGGCCAGCTCATGGAAATACAAAGGGACATTCTGTGAGGCG |
| oligo133 (SEQ ID NO: 134)<br>GCTACAGTTCTTTGATTAGTAACTATCGGCCTTGCACAGACA |
| oligo134 (SEQ ID NO: 135)<br>TTGCTTTAATTAACCGTTGTAATCCAGAACAATATGAAAGCG |
| oligo135 (SEQ ID NO: 136)<br>ACGTGCTAAAGAGTCTGTCCAAGCCATTGCAACAGGAGATAG |
| oligo136 (SEQ ID NO: 137)<br>GGCCGATAATCCTGAGAAGTGTTGACGCTCAATCGCCAGTCA |
| oligo137 (SEQ ID NO: 138)<br>CCGAGCTCGAATTCGTAATCA |
| oligo138 (SEQ ID NO: 139)<br>GGCCCTGTTTTCACCAGTGAGCAACATA |
| oligo139 (SEQ ID NO: 140)<br>AAAACAGACGTTAATATTTTGGGATTGA |
| oligo140 (SEQ ID NO: 141)<br>ATGAGGCCGGAGAATTAAATAGTA |
| oligo141 (SEQ ID NO: 142)<br>GAGAATGATATTCATTGAATCTAGGAAT |
| oligo142 (SEQ ID NO: 143)<br>GGGATTTGATAGTTGCGCCGAATATATT |
| oligo143 (SEQ ID NO: 144)<br>TGAATTTATGATACAGGAGTGTGCCGTC |

| NUCLEIC ACID SEQUENCES |
|---|
| oligo144 (SEQ ID NO: 145)<br>GAGTCTTTTCTATCACCCGGAAAT |
| oligo145 (SEQ ID NO: 146)<br>TGAAAATTATCCCAATCCAAAATTACCG |
| oligo146 (SEQ ID NO: 147)<br>AAATTATAAGAAAACAAAATTTTTTAA |
| oligo147 (SEQ ID NO: 148)<br>ATATTTTATAGCCCTAAAACAAGGAAGG |
| oligo148 (SEQ ID NO: 149)<br>AATGCAATACGGCGCGTCTGCGCG |
| oligo149 (SEQ ID NO: 150)<br>GGCCCTGTTTTCACCAGTGAGCAACATATTCCTCTACCACCTACATCAC |
| oligo150 (SEQ ID NO: 151)<br>AAAACAGACGTTAATATTTTGGGATTGATTCCTCTACCACCTACATCAC |
| oligo151 (SEQ ID NO: 152)<br>ATGAGGCCGGAGAATTAAATAGTATTCCTCTACCACCTACATCAC |
| oligo152 (SEQ ID NO: 153)<br>GAGAATGATATTCATTGAATCTAGGAATTTCCTCTACCACCTACATCAC |
| oligo153 (SEQ ID NO: 154)<br>GGGATTTGATAGTTGCGCCGAATATATTTTCCTCTACCACCTACATCAC |
| oligo154 (SEQ ID NO: 155)<br>TGAATTTATGATACAGGAGTGTGCCGTCTTCCTCTACCACCTACATCAC |
| oligo155 (SEQ ID NO: 156)<br>GAGTCTTTTCTATCACCCGGAAATTTCCTCTACCACCTACATCAC |
| oligo156 (SEQ ID NO: 157)<br>TGAAAATTATCCCAATCCAAAATTACCGTTCCTCTACCACCTACATCAC |
| oligo157 (SEQ ID NO: 158)<br>AAATTATAAGAAAACAAAATTTTTTAATTCCTCTACCACCTACATCAC |
| oligo158 (SEQ ID NO: 159)<br>ATATTTTATAGCCCTAAAACAAGGAAGGTTCCTCTACCACCTACATCAC |
| oligo159 (SEQ ID NO: 160)<br>AATGCAATACGGCGCGTCTGCGCGTTCCTCTACCACCTACATCAC |
| oligo160 (SEQ ID NO: 161)<br>CAAAATCAAACCTGTCGTGCCGCCCGCT |
| oligo161 (SEQ ID NO: 162)<br>AGCCGCCGCGAAACGTACAGCATCCCGT |
| oligo162 (SEQ ID NO: 163)<br>GCCCAAGGATTGCGGGAAGATACA |
| oligo163 (SEQ ID NO: 164)<br>GGAAGCCGCTTTTGCAAAAGACGTTTAC |
| oligo164 (SEQ ID NO: 165)<br>TCACGTTAAAAAAAAGGCTCCACGAGGG |
| oligo165 (SEQ ID NO: 166)<br>GAGGTTGGCCTATTTCGGAACGAAACAT |
| oligo166 (SEQ ID NO: 167)<br>GAACAGAATCCGTCACCTCAATAG |
| oligo167 (SEQ ID NO: 168)<br>AGTCAGAAATTTTATCCTGAAGACTTGC |
| oligo168 (SEQ ID NO: 169)<br>TTTACATTTTGAATACCAAGTTTAGAAT |
| oligo169 (SEQ ID NO: 170)<br>CACGACCCGCCTGCAACAGTGTAAAGCA |
| oligo170 (SEQ ID NO: 171)<br>AAAACGCCAGTAAAGGGGGAAAGC |
| oligo171 (SEQ ID NO: 172)<br>CAAAATCAAACCTGTCGTGCCGCCCGCTTATCTTCCTCACACTCCCAAA |
| oligo172 (SEQ ID NO: 173)<br>AGCCGCCGCGAAACGTACAGCATCCCGTTATCTTCCTCACACTCCCAAA |
| oligo173 (SEQ ID NO: 174)<br>GCCCAAGGATTGCGGGAAGATACATATCTTCCTCACACTCCCAAA |
| oligo174 (SEQ ID NO: 175)<br>GGAAGCCGCTTTTGCAAAAGACGTTTACTATCTTCCTCACACTCCCAAA |
| oligo175 (SEQ ID NO: 176)<br>TCACGTTAAAAAAAAGGCTCCACGAGGGTATCTTCCTCACACTCCCAAA |
| oligo176 (SEQ ID NO: 177)<br>GAGGTTGGCCTATTTCGGAACGAAACATTATCTTCCTCACACTCCCAAA |
| oligo177 (SEQ ID NO: 178)<br>GAACAGAATCCGTCACCTCAATAGTATCTTCCTCACACTCCCAAA |
| oligo178 (SEQ ID NO: 179)<br>AGTCAGAAATTTTATCCTGAAGACTTGCTATCTTCCTCACACTCCCAAA |
| oligo179 (SEQ ID NO: 180)<br>TTTACATTTTGAATACCAAGTTTAGAATTATCTTCCTCACACTCCCAAA |
| oligo180 (SEQ ID NO: 181)<br>CACGACCCGCCTGCAACAGTGTAAAGCATATCTTCCTCACACTCCCAAA |
| oligo181 (SEQ ID NO: 182)<br>AAAACGCCAGTAAAGGGGGAAAGCTATCTTCCTCACACTCCCAAA |

| NUCLEIC ACID SEQUENCES |
| --- |
| oligo182 (SEQ ID NO: 183)<br>CCAGCAGGGGGAGAGGCGGTTCTAATGA |
| oligo183 (SEQ ID NO: 184)<br>GACGTTGAGAGATAGACTTTCTGCCGCC |
| oligo184 (SEQ ID NO: 185)<br>TGTCAATTCAGCTCATTTTTTAGCGAGT |
| oligo185 (SEQ ID NO: 186)<br>GGTATGCCTGTAAATCGTTCATTT |
| oligo186 (SEQ ID NO: 187)<br>TTATAGTTGTTTAGACTGGATAGGAATT |
| oligo187 (SEQ ID NO: 188)<br>AATAGAATCAGCTTGCTTTCGTTTGCGG |
| oligo188 (SEQ ID NO: 189)<br>CAAATAATGCCTTGAGTAACAGATTAGG |
| oligo189 (SEQ ID NO: 190)<br>GAACATCGGCCAAAATCGGGCGAC |
| oligo190 (SEQ ID NO: 191)<br>GAAGCGCAGAGCCTAATTTGCATCCGGT |
| oligo191 (SEQ ID NO: 192)<br>TTTTCAGATTTCAATTACCTGTAACCTT |
| oligo192 (SEQ ID NO: 193)<br>AACCCTTCAGCAGAAGATAAACAATATC |
| oligo193 (SEQ ID NO: 194)<br>AACCCGAGTATTCCTCGAAAGGAG |
| oligo194 (SEQ ID NO: 195)<br>CCAGCAGGGGGAGAGGCGGTTCTAATGATAACATTCCTAACTTCTCATA |
| oligo195 (SEQ ID NO: 196)<br>GACGTTGAGAGATAGACTTTCTGCCGCCTAACATTCCTAACTTCTCATA |
| oligo196 (SEQ ID NO: 197)<br>TGTCAATTCAGCTCATTTTTTAGCGAGTTAACATTCCTAACTTCTCATA |
| oligo197 (SEQ ID NO: 198)<br>GGTATGCCTGTAAATCGTTCATTTTAACATTCCTAACTTCTCATA |
| oligo198 (SEQ ID NO: 199)<br>TTATAGTTGTTTAGACTGGATAGGAATTTAACATTCCTAACTTCTCATA |
| oligo199 (SEQ ID NO: 200)<br>AATAGAATCAGCTTGCTTTCGTTTGCGGTAACATTCCTAACTTCTCATA |
| oligo200 (SEQ ID NO: 201)<br>CAAATAATGCCTTGAGTAACAGATTAGGTAACATTCCTAACTTCTCATA |

| NUCLEIC ACID SEQUENCES |
| --- |
| oligo201 (SEQ ID NO: 202)<br>GAACATCGGCCAAAATCGGGCGACTAACATTCCTAACTTCTCATA |
| oligo202 (SEQ ID NO: 203)<br>GAAGCGCAGAGCCTAATTTGCATCCGGTTAACATTCCTAACTTCTCATA |
| oligo203 (SEQ ID NO: 204)<br>TTTTCAGATTTCAATTACCTGTAACCTTTAACATTCCTAACTTCTCATA |
| oligo204 (SEQ ID NO: 205)<br>AACCCTTCAGCAGAAGATAAACAATATCTAACATTCCTAACTTCTCATA |
| oligo205 (SEQ ID NO: 206)<br>AACCCGAGTATTCCTCGAAAGGAGTAACATTCCTAACTTCTCATA |
| Sequences of staple strands for the DNA container in FIG. 9. |
| oligo1 (SEQ ID NO: 207)<br>ACATCGTGAATACATTAGCGACCAGAG |
| oligo2 (SEQ ID NO: 208)<br>TTAGAAGGTCAATACCGAACACTTTTTA |
| oligo3 (SEQ ID NO: 209)<br>CCGTACTAGTATAGCCTAAATTATGTAA |
| oligo4 (SEQ ID NO: 210)<br>CGACGTTTTTTGCAATGTTTAGAAGAGAA |
| oligo5 (SEQ ID NO: 211)<br>CGAGCATCCCGTCGGGAGTTAGGCGCATA |
| oligo6 (SEQ ID NO: 212)<br>CCATATGCACTCCAACTAAAAAATTGGGCTTGAG |
| oligo7 (SEQ ID NO: 213)<br>GCGTGCCATTAAAGGCCGTTCATATTACGGTAATC |
| oligo8 (SEQ ID NO: 214)<br>AGGTGAGTTAACACTAACGTCATAGCAGCCTTTAC |
| oligo9 (SEQ ID NO: 215)<br>AGCCAGCAAATCTAAACAGGGGACGGGAGAATTAA |
| oligo10 (SEQ ID NO: 216)<br>GTTATCTTAGGAGCAATAAGAATGAAATAGCAATA |
| oligo11 (SEQ ID NO: 217)<br>AAAAGCCTGAGCAATACCTTTCCACCCTCAGAGCC |
| oligo12 (SEQ ID NO: 218)<br>CGCCATGTTTACCAAACATAGATCAAAAGCGTCAT |
| oligo13 (SEQ ID NO: 219)<br>AAACGTATGCAAATATTTCATGTTAAATAACACTG |

| NUCLEIC ACID SEQUENCES |
|---|
| oligo14 (SEQ ID NO: 220)<br>ACGCCGAATAAACAAATTCTTGTAACGAATTTTGC |
| oligo15 (SEQ ID NO: 221)<br>TTTGAGGGGACGACAACAAGATGCCCTGAACCGAT |
| oligo16 (SEQ ID NO: 222)<br>TCGGCTAATTCTGTATCAACAGCTTGCTCAACAAC |
| oligo17 (SEQ ID NO: 223)<br>GCGAGGTTTTTGTTAAATCAGATTGTATCGCCTGT |
| oligo18 (SEQ ID NO: 224)<br>GACACCACGGAATAACATACAACAAAGATGAGGAT |
| oligo19 (SEQ ID NO: 225)<br>TCCAACAGGTCTGAAGCCAGTTTTGATCAGAATGA |
| oligo20 (SEQ ID NO: 226)<br>AAAACCAGGATTAGCGGGGTTAAGTATTATCGGCG |
| oligo21 (SEQ ID NO: 227)<br>AAAGAGCTCCTGTACGTGGGACACATCCTAATTTA |
| oligo22 (SEQ ID NO: 228)<br>GCAGTGTTCAATCAAAGGCTAAATTGAGCGATGCCG |
| oligo23 (SEQ ID NO: 229)<br>AACAATTCTCGTCAAAACCGATCAAAAGGGCTTACC |
| oligo24 (SEQ ID NO: 230)<br>ATCATAGCATCAGCAGTTTGAACCCTGTGACTCCTT |
| oligo25 (SEQ ID NO: 231)<br>CAGTAGTGCCGGACAAACAGATCTACTAGGAAGGTA |
| oligo26 (SEQ ID NO: 232)<br>CCCTTAGACGCAGATGCCGCCGAAGCCCCTTCAAAG |
| oligo27 (SEQ ID NO: 233)<br>GAGAGATCGGAAAACTGACTAAAGATTAAGCCGTTC |
| oligo28 (SEQ ID NO: 234)<br>GGTGCGGGCCTCTTAACGCTCAATCTACCAGTTTCA |
| oligo29 (SEQ ID NO: 235)<br>ATAATCGATCGAGAGGGATCGAGGCTTTGAGTGTAC |
| oligo30 (SEQ ID NO: 236)<br>GATAGGTACAAACGCCGGATATCATCAAGAGTAATCT |
| oligo31 (SEQ ID NO: 237)<br>AGTCATAAGTTGCCACATTATTCATCAGTTGAGTTATACC |
| oligo32 (SEQ ID NO: 238)<br>TCTTCGCCTCCTCTCAAAAACTGGCCTAGACGGTGGAACCG |
| oligo33 (SEQ ID NO: 239)<br>CCCTCACTTTACCAGAGAATCCTTGAAGTCCCGGCCTCACC |
| oligo34 (SEQ ID NO: 240)<br>CGCCTGTGCACTCTTGAACCTGAGAGTCCCCTGAACAAAGTC |
| oligo35 (SEQ ID NO: 241)<br>AATCAACAGTTGAACATCCCTAAGAATTAGAAAGGCCGGAGA |
| oligo36 (SEQ ID NO: 242)<br>CGGTAGCGCACTCAGCCATCCACCCAACGAATGCACTGGTCT |
| oligo37 (SEQ ID NO: 243)<br>CTTCTGAGAGGTGTTATGGTTAAAACATTAAAGAAACGCAAA |
| oligo38 (SEQ ID NO: 244)<br>CGGCCTTTAGTGATTCCGGCAATAAGAGCTGAATATACCCTC |
| oligo39 (SEQ ID NO: 245)<br>GCTCATTAACAGCGGCTCTCAAGACTTTAGCCGCCGCCAGTG |
| oligo40 (SEQ ID NO: 246)<br>TGAGAAGGAATAACCTTGCTTTTTTAATCTCATTAAGGCAGG |
| oligo41 (SEQ ID NO: 247)<br>CCAATCGCAAGACAGGAAACAAAGAGGCTAAACAGTTCAGAA |
| oligo42 (SEQ ID NO: 248)<br>ATGCTGACCTTTTTATTCTGAGCCCGTATAAACAGAGTGCCT |
| oligo43 (SEQ ID NO: 249)<br>TGGGAAGTTCGCCAAGTCAGGATTTTAAGAACTGGTGTGAAT |
| oligo44 (SEQ ID NO: 250)<br>GCAAAGCCACCGCTTACCTTAAATTTCAACTTTAACAAAGCT |
| oligo45 (SEQ ID NO: 251)<br>CGTGCATTTGGTGTGCTCATTTTACCCAAATCAACACAAGAA |
| oligo46 (SEQ ID NO: 252)<br>TCATTCCATTAAACGAAAGACCGAGGGTAGCAACGCATGAGG |
| oligo47 (SEQ ID NO: 253)<br>TTCATCAACCAACCGAAAGAGGACAGATGAACGGGGCCACTA |
| oligo48 (SEQ ID NO: 254)<br>CTATTTTGCACCATTTGCGGGTGTATCACCCCCAGCGATTAT |
| oligo49 (SEQ ID NO: 255)<br>AACCCACTACACTGTTCTTTGCGACAACTTTTAAAGGGGTCA |
| oligo50 (SEQ ID NO: 256)<br>ATCACCATCAATATAATGCCTTAGAACCTTTTACCTTTATTT |
| oligo51 (SEQ ID NO: 257)<br>GAGTAATGTGTAGGCAGTCAAGAGAGATAGAGGGTTCAGGTC |

| NUCLEIC ACID SEQUENCES |
| --- |
| oligo52 (SEQ ID NO: 258)<br>TAAAGATGGAAACGTGATTAAAATACTTTGTACCATACCAGC |
| oligo53 (SEQ ID NO: 259)<br>CAAAAGAACTGGCACAATAATTAAAGGTGTGTGTTGTTGGCA |
| oligo54 (SEQ ID NO: 260)<br>AGAGCATGGGCAAAAATTACGAATAAATATTTTCAGCTGGTC |
| oligo55 (SEQ ID NO: 261)<br>CAATAGAGACGGAACGACTTGAGCCAATAATAAAGGATTATA |
| oligo56 (SEQ ID NO: 262)<br>ACTGTAGCGCGTTTTAGCACCCAATAACCGTCAGATGAATAT |
| oligo57 (SEQ ID NO: 263)<br>CCACCACACCACCCGTAGGATTAGAGAGAAGAAGACAAAATC |
| oligo58 (SEQ ID NO: 264)<br>AGAACCGAATTGCTAGACCGGTCTCTGAATTTAAGAGCAGTT |
| oligo59 (SEQ ID NO: 265)<br>GATACAGGAGTGTAATAAATCGGAAACATTTCATTTGAATTA |
| oligo60 (SEQ ID NO: 266)<br>AACGAGTAACATGATTGCTCATACAGACGACGATATTAGTTA |
| oligo61 (SEQ ID NO: 267)<br>TTACAGGGAAGAAAAACAGTAGGGCTCAGGCGATCAGGCGAT |
| oligo62 (SEQ ID NO: 268)<br>GTAGCATTCCACAGTTTTGTCATATGCGGAGGCATTTTCGAG |
| oligo63 (SEQ ID NO: 269)<br>AAACGGCACCAGTACGCCAACATGTAATAAGGTAATAATTTT |
| oligo64 (SEQ ID NO: 270)<br>TCGGTTTATAGAACGAGTAGTGGAATTGCTTTCAAGTTAATA |
| oligo65 (SEQ ID NO: 271)<br>CACTAAAACACTCACGAAGGCACATTAAATGTGAACAAATCA |
| oligo66 (SEQ ID NO: 272)<br>TCTTTGATCGCCTGATAAATTGCGAACCGATATAGCCGAGCT |
| oligo67 (SEQ ID NO: 273)<br>ATCAAAATGGCTTAGATAACTATTAATGGCGACCGTTACAAAC |
| oligo68 (SEQ ID NO: 274)<br>AAGAACGCGAGAAAACGACGACGGGAAGGATAGCTTGAATCC |
| oligo69 (SEQ ID NO: 275)<br>TCCCGACTTTGTTAAAATTCGAATTGTACGAACTGAACGAACC |
| oligo70 (SEQ ID NO: 276)<br>ATTCGCCTGAACAAAATTAACAAGTACATATGTGAGTAGTCAAT |
| oligo71 (SEQ ID NO: 277)<br>ACCAGCTGCTGCGAATAAGAGCAAACAAGAGAATATTGCCTCAAATAT |
| oligo72 (SEQ ID NO: 278)<br>GAGAGGTTGAGAGCTAGCATTGTACCCCGGTTGCTTCACGGATCCAGC |
| oligo73 (SEQ ID NO: 279)<br>GAAGCCAAGTTACCAGTATGGGCAACATATAATGGTAACATCTTTACA |
| oligo74 (SEQ ID NO: 280)<br>ATTACGCAGAAGGTATAGATTAGAGCCTATTAGATATCATTAATTATC |
| oligo75 (SEQ ID NO: 281)<br>ATCGGTTTGCGGGTTATTAATCGTATTAAATCCTTAATGGGAACGGAA |
| oligo76 (SEQ ID NO: 282)<br>AATATTAAATTCACCATTCCTGATTATTTGTTTGAAATTGCACAGTAA |
| oligo77 (SEQ ID NO: 283)<br>CGAACCCCTTTTGAAATTTCAATTACCGCACAGGGGGCGGTTAATTTT |
| oligo78 (SEQ ID NO: 284)<br>CAGTAAATCAGGTAATGCTTTGAGACTCCTCACTCGGATAAAATTTGT |
| oligo79 (SEQ ID NO: 285)<br>GGATTAAAATAGCGCAACACCCACCACCCTCATTTTCAGACGAGGCAT |
| oligo80 (SEQ ID NO: 286)<br>CGGATAACCTATTAACCTCCCATAGGTCTGAGAGAAGACGCTGAGTAA |
| oligo81 (SEQ ID NO: 287)<br>GCGGAGTGAGACGACGTTGGTAGAAAGCAGGATAGCAAGCCTGCTGCA |
| oligo82 (SEQ ID NO: 288)<br>AGACCAAAGGCCGCACGCATACGAGAAACACCCAATAGATACCAATCA |
| oligo83 (SEQ ID NO: 289)<br>CGAATTCTAATGCGAACGTTAGAGCCTAATTTGCCCAATCCAGCCAGAA |
| oligo84 (SEQ ID NO: 290)<br>CGTGGCATTTTGAATATCCTGACGCTAACGAGCGTTTTTGTTCGCCTGC |
| oligo85 (SEQ ID NO: 291)<br>AACAGGGAGAAGATTAGTCTTAAAGCGTTAGCAAGGCAAGCCACGTAAT |
| oligo86 (SEQ ID NO: 292)<br>CAAACCCCACTGCGTGCGGCGAATACCGATAGCCCCCGGGTAAAGGCTT |
| oligo87 (SEQ ID NO: 293)<br>TGCCCTGCGGCATCTTACCTGCAGCCATCTGGTCACAGCAAAAATATCA |
| oligo88 (SEQ ID NO: 294)<br>GGAGCGGTTGCGGATAAAGGTTTAGCAAACGTAGACAGATAGGATAATA |
| oligo89 (SEQ ID NO: 295)<br>ACGGCTGATAATGGGCACGTATTGTAGAATCCTCAGCGCAGAGGAAGTT |

| NUCLEIC ACID SEQUENCES |
|---|
| oligo90 (SEQ ID NO: 296)<br>GTAGATTCCGTCACATTATTCATTAAAGTATTTTGTGGCAATACCAGAA |
| oligo91 (SEQ ID NO: 297)<br>GGCAGCCCGGTCCGTGCAACTGCTGTAGCTCAACATTAATTGGTCATTT |
| oligo92 (SEQ ID NO: 298)<br>TAACGGAAACGTCAGTGGCATCATTTGGGAATTAGTTAGCAAGCGTCAG |
| oligo93 (SEQ ID NO: 299)<br>ACAAACAACAGGAGTCAGAGCCGCCACCCACCGGATTTGCCATTCGGTC |
| oligo94 (SEQ ID NO: 300)<br>TAGGCATTATACACCGGAATATAAGGCCTTCTGACCCGGAAGTACCAGG |
| oligo95 (SEQ ID NO: 301)<br>GAGAATACTCCAAACAAAAGGAGCCTTTTGAATTTGAACGCGTTCCTTA |
| oligo96 (SEQ ID NO: 302)<br>ATTCTCAACAGTTGAGGATCCTAAAACATAAGCAAAAATAAACAGATAA |
| oligo97 (SEQ ID NO: 303)<br>TCAGAAAACAGGAAGCTCATTTAGGAACTCCATGTGAACGAGGCGGCAA |
| oligo98 (SEQ ID NO: 304)<br>GTAAAAATCTACAATAGCGGTGCCGGTTCAGACGTCATACCGCCAGCAC |
| oligo99 (SEQ ID NO: 305)<br>CGATGAATTTATCCAGTTACAATATTTACATTAAACGTTTTAGTGTCGA |
| oligo100 (SEQ ID NO: 306)<br>AGAGAGAAACGATTCTTTCCAATCAGCTACAATTTTGGCTATAAAACAG |
| oligo101 (SEQ ID NO: 307)<br>GCCCAATACTAACAACTAAAAAGGAATTACCTTGCGTTGCCACGCTGAG |
| oligo102 (SEQ ID NO: 308)<br>GCTATTGGAGTTAACTGAACATGGAATAACATAAAAAGCATCGAGGAAG |
| oligo103 (SEQ ID NO: 309)<br>TTTAAATGCGATATTCGCTGATAAATTACTTCGTTAACGGCTGGTTTGA |
| oligo104 (SEQ ID NO: 310)<br>ACCGATTGCCAAAGCCAGCTTTTGCAGGCGCTTTCCCGAACGAGAAGCC |
| oligo105 (SEQ ID NO: 311)<br>GAGGGAGATAGTAGTGAAAAGCCAATGAACAGAATCAATTCTGCGAACG |
| oligo106 (SEQ ID NO: 312)<br>AGCATTATTATTTAAGGGTTAGAACCTCACGCAAACAAAGAAAGCTAA |
| oligo107 (SEQ ID NO: 313)<br>AAAATCAATTATCATTCAGGTCAATATAATCCTGACAGATGATCACAAT |
| oligo108 (SEQ ID NO: 314)<br>AACCATCAGAGCACACGTCAGCGTGGTGTATCAAAAACATCCACATTCA |
| oligo109 (SEQ ID NO: 315)<br>GCAAAACTTAGTTTGACCATTTTAAATATTTTTTCTTGCCGTGAAGGGT |
| oligo110 (SEQ ID NO: 316)<br>TAGCCCCCACAGTTGATTCCCAAGTTTGCCTTTAGGCCGGAACCCTTTT |
| oligo111 (SEQ ID NO: 317)<br>GGTGTCTGGCGAATTATTCCGTCCGGCCGATAGCATTTGGGGCGCGAGC |
| oligo112 (SEQ ID NO: 318)<br>GCCTCCCTCAGAGCCGCCAATAAAGTACAGTAGATCGTAATCAGTAGCG |
| oligo113 (SEQ ID NO: 319)<br>CGGAACCTCATTCCATATATTCAAGTTATGATGAACCAAATCCCGTAAA |
| oligo114 (SEQ ID NO: 320)<br>TCAAAATAGAACCACGCCGCCATTGGCCCAAACAACTGGTAACGGGTC |
| oligo115 (SEQ ID NO: 321)<br>ATTCGAGGAAAGACCATCAAATTATAGTATATTCAGTCCAATTAGTAAA |
| oligo116 (SEQ ID NO: 322)<br>TCAGACGAGCATTGTCAAGAAATTGCTTGGAGAAAATTACCAAGCCAGC |
| oligo117 (SEQ ID NO: 323)<br>ACATGGCAATGGAAATCGACATAAAATTCTGTAAATTAGATTACTACAG |
| oligo118 (SEQ ID NO: 324)<br>CCATAACGATAGCTCGTCGCTATTAATTGTGTACAGCGCAGAAGCAAAC |
| oligo119 (SEQ ID NO: 325)<br>TTAATGCTTTCGGAAGTGCCGTGATATACAGGAGGCCACCCTCAGAACC |
| oligo120 (SEQ ID NO: 326)<br>AAAGAAGGAATTACTAATGCAGATACATAGGAATAGGTAACGCAACTGT |
| oligo121 (SEQ ID NO: 327)<br>AGTAAGAGAGAGGCGTAAACTTTTTCAAGGGGATGCAATAGGAACATTA |
| oligo122 (SEQ ID NO: 328)<br>TTTACGGTCAGAACCGCCACCGTACCGTAAAGCTGGCGAAAGATATATT |
| oligo123 (SEQ ID NO: 329)<br>TCACCAGGTGATAACATAATTACTAGAATAGTATCGTCTTTCTAAATGA |
| oligo124 (SEQ ID NO: 330)<br>TCATAGTTAAACTAACGGAACAACCCATCTCAGAGTATCATAACCCTCG |
| oligo125 (SEQ ID NO: 331)<br>TAAACAACGAATAAAGCTCAGGAAGATCTTAACAATAAAGCCCGCTATT |
| oligo126 (SEQ ID NO: 332)<br>ATTTTCTTGAAAATTAAAGTAACGACAATAAACAATAATGCACTTAAAC |
| oligo127 (SEQ ID NO: 333)<br>TTCACGTGTATGGGTCTAAAGACAGCCCAGTTTCGGCCACCCTGTATCA |

NUCLEIC ACID SEQUENCES oligo128
(SEQ ID NO: 334)
AAGGCTAAAATAATATCCCGCTGCCAGTTTCCGGGCTAATTGAGAATCG oligo129
(SEQ ID NO: 335)
ATATTCGGTCGCCACAGTGAAATGGTTTTGATAGAAAGGAACAGCCAGC oligo130
(SEQ ID NO: 336)
CATCGCCCTTTTGCACAGCGAGTAACAAGTAGAAAAGTCCTGGACAGTA oligo131
(SEQ ID NO: 337)
TGCGCCGCAGCAGCCAAGTACTTTTCATATTACCGGAAGCCTTTAGTTG oligo132
(SEQ ID NO: 338)
GGCTGGCAACTTTTAAAACGAAGAATAAATCCGCGACCTGCGCAAGAAC oligo133
(SEQ ID NO: 339)
AACTGACCTGACCTTTTGAGGCTTGCAGGATTCTCGCCAGCTATCCGGT oligo134
(SEQ ID NO: 340)
ACTAAAGACTTTTTGCTACAGTCACCCTACAATGATTCGAGGAATTGTA oligo135
(SEQ ID NO: 341)
GTAAAATGTTTTTACGCACTCGCTGTCTCCTGTTTCCAGACGCCGACAA oligo136
(SEQ ID NO: 342)
TAAACGGACCAAGCGTACAACGGAGATTAGGTTTTCGCCCAAAAGAATA

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising:

growing a nanoparticle from a nanoparticle precursor inside a nucleic acid container by applying a stimulus to the nanoparticle precursor positioned inside of the nucleic acid container, wherein the nucleic acid container is a template for formation of the nanoparticle, wherein the nanoparticle has a different shape than the nanoparticle precursor, wherein the nanoparticle comprises at least one surface portion having a shape that is complementary to a shape of an inner surface portion of the nucleic acid container having a predetermined three-dimensional structure at the sub-nanometer level, and wherein the nanoparticle and the nucleic acid container have a three-dimensional shape that includes at least 4 different sides.

2. A method as in claim 1, wherein the nanoparticle comprises an inorganic nanoparticle.

3. A method as in claim 1, wherein the nanoparticle precursor comprises a monomer of an organic polymer, an enzyme, or a peptide.

4. A method as in claim 1, wherein the nanoparticle precursor has a cross-sectional dimension of less than or equal to 50 nm.

5. A method as in claim 1, wherein the nanoparticle has a shape that is complementary to a shape of the inner surfaces of the nucleic acid container.

6. A method as in claim 1, wherein the nanoparticle is an inorganic nanoparticle.

7. A method as in claim 1, wherein the nanoparticle comprises a polymer.

8. A method as in claim 1, wherein the nanoparticle has at least one cross-sectional dimension that is less than or equal to 1 micron.

9. A method as in claim 1, wherein the nanoparticle has an aspect ratio of at least 2:1.

10. A method as in claim 1, further comprising attaching an isolated nucleic acid strand comprising DNA and/or RNA to a surface of the nanoparticle.

11. A method as in claim 1, wherein the nucleic acid container comprises a cavity having a volume, and at least 60% -of the volume is filled with the nanoparticle.

12. A method as in claim 1, wherein the nucleic acid container comprises a cavity in the shape of a polyhedron.

13. A method as in claim 1, wherein the nucleic acid container comprises at least one lid that can be open or closed.

14. A method as in claim 1, wherein the nucleic acid container comprises a cavity, and a cross-sectional dimension of the cavity is less than or equal to 1 micron.

15. A method as in claim 1, wherein the nucleic acid container comprises a nucleic acid having a molecular weight of at least 640 kDa.

16. A method as in claim 1, wherein the nucleic acid container comprises a cavity having a pre-designed three-dimensional structure, and the shape of the nanoparticle is formed, at least in part, by molding against the cavity.

17. A method as in claim 1, wherein the growing step comprises controlling ion diffusion kinetics to control the growth kinetics and/or composition of the nanoparticle.

18. A method as in claim 1, further comprising attaching a protein, a peptide, a marker, or a second nanoparticle to a surface of the nanoparticle.

19. A method as in claim 1, wherein the nanoparticle is formed using a nanoparticle precursor solution.

20. A method as in claim 1, wherein the stimulus is an external force, a chemical component.

21. A method as in claim 20, wherein the stimulus is selected from the group consisting of heat, light, pressure, electrical potential, magnetic force, electromagnetic force, a chemical component.

* * * * *

SEQUENCE LISTING

```
<160> NUMBER OF SEQ ID NOS: 342

<210> SEQ ID NO 1
<211> LENGTH: 8064
<212> TYPE: DNA
<213> ORGANISM: Artificial Sequence
<220> FEATURE:
<223> OTHER INFORMATION: Synthetic Polynucleotide

<400> SEQUENCE: 1
gaattcgagc tcggtacccg gggatcctca actgtgagga ggctcacgga cgcgaagaac      60
aggcacgcgt gctggcagaa accccggta tgaccgtgaa aacggcccgc cgcattctgg     120
ccgcagcacc acagagtgca caggcgcgca gtgacactgc gctggatcgt ctgatgcagg     180
gggcaccggc accgctggct gcaggtaacc cggcatctga tgccgttaac gatttgctga     240
acacaccagt gtaagggatg tttatgacga gcaaagaaac ctttacccat taccagccgc     300
agggcaacag tgacccggct cataccgcaa ccgcgcccgg cggattgagt gcgaaagcgc     360
```

```
ctgcaatgac cccgctgatg ctggacacct ccagccgtaa gctggttgcg tgggatggca    420
ccaccgacgg tgctgccgtt ggcattcttg cggttgctgc tgaccagacc agcaccacgc    480
tgacgttcta caagtccggc acgttccgtt atgaggatgt gctctggccg gaggctgcca    540
gcgacgagac gaaaaaacgg accgcgtttg ccggaacggc aatcagcatc gtttaacttt    600
acccttcatc actaaaggcc gcctgtgcgg cttttttac gggattttt tatgtcgatg    660 tacacaaccg cccaactgct ggcggcaaat gagcagaaat ttaagtttga tccgctgttt    720
ctgcgtctct ttttccgtga gagctatccc ttcaccacgg agaaagtcta tctctcacaa    780
attccgggac tggtaaacat ggcgctgtac gtttcgccga ttgtttccgg tgaggttatc    840
cgttcccgtg gcggctccac ctctgaaagc ttggcactgg ccgtcgtttt acaacgtcgt    900
gactgggaaa accctggcgt tacccaactt aatcgcttg cagcacatcc cccttcgcc    960 agctggcgta atagcgaaga ggcccgcacc gatcgccctt ccaacagtt gcgcagcctg    1020 aatggcgaat ggcgctttgc ctggtttccg gcaccagaag cggtgccgga agctggctg    1080 gagtgcgatc ttcctgaggc cgatactgtc gtcgtcccct caaactggca gatgcacggt    1140
tacgatgcgc ccatctacac caacgtgacc tatcccatta cggtcaatcc gccgtttgtt    1200
cccacggaga atccgacggg ttgttactcg ctcacattta atgttgatga aagctggcta    1260
caggaaggcc agacgcgaat tattttgat ggcgttccta ttggttaaaa atgagctga    1320 tttaacaaaa atttaatgcg aattttaaca aaatattaac gtttacaatt taaatatttg    1380
cttatacaat cttcctgttt ttggggcttt tctgattatc aaccgggta catatgattg    1440 acatgctagt tttacgatta ccgttcatcg attctcttgt ttgctccaga ctctcaggca    1500
atgacctgat agcctttgta gatctctcaa aaatagctac cctctccggc attaatttat    1560
cagctagaac ggttgaatat catattgatg gtgatttgac tgtctccggc ctttctcacc    1620
cttttgaatc tttacctaca cattactcag gcattgcatt taaaatatat gagggttcta    1680
aaaattttta tccttgcgtt gaaataaagg cttctcccgc aaaagtatta cagggtcata    1740 atgttttgg tacaaccgat ttagctttat gctctgaggc tttattgctt aattttgcta    1800
attctttgcc ttgcctgtat gatttattgg atgttaatgc tactactatt agtagaattg    1860
atgccacctt ttcagctcgc gccccaaatg aaaatatagc taaacaggtt attgaccatt    1920
tgcgaaatgt atctaatggt caaactaaat ctactcgttc gcagaattgg gaatcaactg    1980
ttatatggaa tgaaacttcc agacaccgta ctttagttgc atatttaaaa catgttgagc    2040
tacagcatta tattcagcaa ttaagctcta agccatccgc aaaaatgacc tcttatcaaa    2100
aggagcaatt aaaggtactc tctaatcctg acctgttgga gtttgcttcc ggtctggttc    2160
gctttgaagc tcgaattaaa acgcgatatt tgaagtcttt cgggcttcct cttaatcttt    2220
ttgatgcaat ccgctttgct tctgactata atagtcaggg taaagacctg attttttgatt    2280 tatggtcatt ctcgttttct gaactgttta aagcatttga ggggattca atgaatattt    2340 atgacgattc cgcagtattg gacgctatcc agtctaaaca ttttactatt accccctctg    2400
gcaaaacttc ttttgcaaaa gcctctcgct attttggttt ttatcgtcgt ctggtaaacg    2460
agggttatga tagtgttgct cttactatgc ctcgtaattc cttttggcgt tatgtatctg    2520
cattagttga atgtggtatt cctaaatctc aactgatgaa tctttctacc tgtaataatg    2580
ttgttccgtt agttcgtttt attaacgtag attttttcttc ccaacgtcct gactggtata    2640
atgagccagt tcttaaaatc gcataaggta attcacaatg attaaagttg aaattaaacc    2700
atctcaagcc caatttacta ctcgttctgg tgtttctcgt cagggcaagc cttattcact    2760
```

```
gaatgagcag ctttgttacg ttgatttggg taatgaatat ccggttcttg tcaagattac    2820
tcttgatgaa ggtcagccag cctatgcgcc tggtctgtac accgttcatc tgtcctcttt    2880
caaagttggt cagttcggtt cccttatgat tgaccgtctg cgcctcgttc cggctaagta    2940
acatggagca ggtcgcggat ttcgacacaa tttatcaggc gatgatacaa atctccgttg    3000
tactttgttt cgcgcttggt ataatcgctg ggggtcaaag atgagtgttt tagtgtattc    3060
ttttgcctct ttcgttttag gttggtgcct tcgtagtggc attacgtatt ttacccgttt    3120
aatggaaact tcctcatgaa aaagtcttta gtcctcaaag cctctgtagc cgttgctacc    3180
ctcgttccga tgctgtcttt cgctgctgag ggtgacgatc ccgcaaaagc ggcctttaac    3240
tccctgcaag cctcagcgac cgaatatatc ggttatgcgt gggcgatggt tgttgtcatt    3300
gtcggcgcaa ctatcggtat caagctgttt aagaaattca cctcgaaagc aagctgataa    3360
accgatacaa ttaaaggctc cttttggagc cttttttttg gagattttca acgtgaaaaa    3420
attattattc gcaattcctt tagttgttcc tttctattct cactccgctg aaactgttga    3480
aagttgttta gcaaaatccc atacagaaaa ttcatttact aacgtctgga agacgacaa     3540 aactttagat cgttacgcta actatgaggg ctgtctgtgg aatgctacag gcgttgtagt    3600
ttgtactggt gacgaaactc agtgttacgg tacatgggtt cctattgggc ttgctatccc    3660
tgaaaatgag ggtggtggct ctgagggtgg cggttctgag ggtggcggtt ctgagggtgg    3720
cggtactaaa cctcctgagt acggtgatac acctattccg ggctatactt atatcaaccc    3780
tctcgacggc acttatccgc ctggtactga gcaaaacccc gctaatccta atccttctct    3840
tgaggagtct cagcctctta atactttcat gtttcagaat aataggttcc gaaataggca    3900
gggggcatta actgtttata cgggcactgt tactcaaggc actgacccc gttaaaactta    3960 ttaccagtac actcctgtat catcaaaagc catgtatgac gcttactgga acggtaaatt    4020
cagagactgc gctttccatt ctggctttaa tgaggattta tttgtttgtg aatatcaagg    4080
ccaatcgtct gacctgcctc aacctcctgt caatgctggc ggcggctctg gtggtggttc    4140
tggtggcggc tctgagggtg gtggctctga gggtggcggt tctgagggtg cggctctga    4200 gggaggcggt tccggtggtg gctctggttc cggtgatttt gattatgaaa agatggcaaa    4260
cgctaataag ggggctatga ccgaaaatgc cgatgaaaac gcgctacagt ctgacgctaa    4320
aggcaaactt gattctgtcg ctactgatta cggtgctgct atcgatggtt tcattggtga    4380
cgtttccggc cttgctaatg gtaatggtgc tactggtgat tttgctggct ctaattccca    4440
aatggctcaa gtcggtgacg gtgataattc acctttaatg aataatttcc gtcaatattt    4500
accttccctc cctcaatcgg ttgaatgtcg cccttttgtc tttggcgctg gtaaaccata    4560
tgaattttct attgattgtg acaaaataaa cttattccgt ggtgtctttg cgtttctttt    4620
atatgttgcc acctttatgt atgtattttc tacgtttgct aacatactgc gtaataagga    4680
gtcttaatca tgccagttct ttttgggtatt ccgttattat tgcgtttcct cggtttcctt    4740
ctggtaactt tgttcggcta tctgcttact tttcttaaaa agggcttcgg taagatagct    4800
attgctattt cattgtttct tgctcttatt attgggctta actcaattct tgtgggttat    4860
ctctctgata ttagcgctca attaccctct gactttgttc agggtgttca gttaattctc    4920
ccgtctaatg cgcttccctg tttttatgtt attctctctg taaaggctgc tattttcatt    4980
tttgacgtta aacaaaaaat cgtttcttat ttggattggg ataaataata tggctgttta    5040
ttttgtaact ggcaaattag gctctggaaa gacgctcgtt agcgttggta agattcagga    5100
```

```
taaaattgta gctgggtgca aaatagcaac taatcttgat ttaaggcttc aaaacctccc    5160
gcaagtcggg aggttcgcta aaacgcctcg cgttcttaga ataccggata agccttctat    5220
atctgatttg cttgctattg ggcgcggtaa tgattcctac gatgaaaata aaaacggctt    5280
gcttgttctc gatgagtgcg gtacttggtt taatacccgt tcttggaatg ataaggaaag    5340
acagccgatt attgattggt ttctacatgc tcgtaaatta ggatgggata ttattttct     5400 tgttcaggac ttatctattg ttgataaaca ggcgcgttct gcattagctg aacatgttgt    5460
ttattgtcgt cgtctggaca gaattacttt accttttgtc ggtactttat attctcttat    5520
tactggctcg aaaatgcctc tgcctaaatt acatgttggc gttgttaaat atggcgattc    5580
tcaattaagc cctactgttg agcgttggct ttatactggt aagaatttgt ataacgcata    5640
tgatactaaa caggcttttt ctagtaatta tgattccggt gtttattctt atttaacgcc    5700
ttatttatca cacggtcggt atttcaaacc attaaattta ggtcagaaga tgaaattaac    5760
taaaatatat ttgaaaaagt tttctcgcgt tctttgtctt gcgattggat ttgcatcagc    5820
atttacatat agttatataa cccaacctaa gccggaggtt aaaaaggtag tctctcagac    5880
ctatgatttt gataaattca ctattgactc ttctcagcgt cttaatctaa gctatcgcta    5940
tgttttcaag gattctaagg gaaaattaat taatagcgac gatttacaga agcaaggtta    6000
ttcactcaca tatattgatt tatgtactgt ttccattaaa aaggtaatt caaatgaaat     6060 tgttaaatgt aattaatttt gttttcttga tgtttgtttc atcatcttct tttgctcagg    6120
taattgaaat gaataattcg cctctgcgcg attttgtaac ttggtattca aagcaatcag    6180
gcgaatccgt tattgtttct cccgatgtaa aaggtactgt tactgtatat tcatctgacg    6240
ttaaacctga aaatctacgc aatttcttta tttctgtttt acgtgcaaat aattttgata    6300
tggtaggttc taacccttcc attattcaga gtataatcc aaacaatcag gattatattg      6360
atgaattgcc atcatctgat aatcaggaat atgatgataa ttccgctcct tctggtggtt    6420
tctttgttcc gcaaaatgat aatgttactc aaacttttaa aattaataac gttcgggcaa    6480
aggatttaat acgagttgtc gaattgtttg taaagtctaa tacttctaaa tcctcaaatg    6540
tattatctat tgacggctct aatctattag ttgttagtgc tcctaaagat attttagata    6600
accttcctca attccttca actgttgatt tgccaactga ccagatattg attgagggtt      6660
tgatatttga ggttcagcaa ggtgatgctt tagattttc atttgctgct ggctctcagc      6720
gtggcactgt tgcaggcggt gttaatactg accgcctcac ctctgtttta tcttctgctg    6780
gtggttcgtt cggtattttt aatggcgatg ttttagggct atcagttcgc gcattaaaga    6840
ctaatagcca ttcaaaaata ttgtctgtgc cacgtattct tacgctttca ggtcagaagg    6900
gttctatctc tgttggccag aatgtccctt ttattactgg tcgtgtgact ggtgaatctg    6960
ccaatgtaaa taatccattt cagacgattg agcgtcaaaa tgtaggtatt tccatgagcg    7020 ttttcctgt tgcaatggct ggcggtaata ttgttctgga tattaccagc aaggccgata    7080
gtttgagttc ttctactcag gcaagtgatg ttattactaa tcaaagaagt attgctacaa    7140
cggttaattt gcgtgatgga cagactcttt tactcggtgg cctcactgat tataaaaaca    7200
cttctcagga ttctggcgta ccgttcctgt ctaaaatccc tttaatcggc ctcctgttta    7260
gctcccgctc tgattctaac gaggaaagca cgttatacgt gctcgtcaaa gcaaccatag    7320
tacgcgccct gtagcggcgc attaagcgcg gcgggtgtgg tggttacgcg cagcgtgacc    7380
gctacacttg ccagcgccct agcgcccgct cctttcgctt tcttcccttc ctttctcgcc    7440
acgttcgccg gctttccccg tcaagctcta aatcggggg tccctttagg gttccgattt    7500
```

```
agtgctttac ggcacctcga ccccaaaaaa cttgatttgg gtgatggttc acgtagtggg   7560
ccatcgccct gatagacggt ttttcgccct ttgacgttgg agtccacgtt ctttaatagt   7620
ggactcttgt tccaaactgg aacaacactc aaccctatct cgggctattc ttttgattta   7680
taagggattt tgccgatttc ggaaccacca tcaaacagga ttttcgcctg ctggggcaaa   7740
ccagcgtgga ccgcttgctg caactctctc agggccaggc ggtgaagggc aatcagctgt   7800
tgcccgtctc actggtgaaa agaaaaacca ccctggcgcc caatacgcaa accgcctctc   7860
cccgcgcgtt ggccgattca ttaatgcagc tggcacgaca ggtttcccga ctggaaagcg   7920
ggcagtgagc gcaacgcaat taatgtgagt tagctcactc attaggcacc ccaggcttta   7980
cactttatgc ttccggctcg tatgttgtgt ggaattgtga gcggataaca atttcacaca   8040
ggaaacagct atgaccatga ttac                                          8064
```

<210> SEQ ID NO 2
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 2

```
taaccaccca ctacgtgaac cacgtcaaag ggcgaaccgc ct                         42
```

<210> SEQ ID NO 3
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 3

```
cgggcgcagg tgccgtaaag ccagtttgga acaaggtttg cc                         42
```

<210> SEQ ID NO 4
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 4

```
cggcgaacga tttagagctt gataaatcaa aagaaaaatc gg                         42
```

<210> SEQ ID NO 5
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 5

```
gttttttttat taaagaacgt gtgcagcaag cggtctgggc gc                        42
```

<210> SEQ ID NO 6
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 6
ctaaaggaga tagggttgag ttcctgtttg atggtttaat ga                42

<210> SEQ ID NO 7
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 7
aaagttgttc actaaatgaa agcgttagaa tcagagcgaa tcagt             45

<210> SEQ ID NO 8
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 8
ttcagagagt gactccaatc acccggtcac gactatgg                     38

<210> SEQ ID NO 9
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 9
cagggtgaaa gtgtaaagcc tttttcacgg tcatcgtgtg tt                42

<210> SEQ ID NO 10
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 10
atcggccatt aattgcgttg ccctgtgcac tctgtctgca gc                42

<210> SEQ ID NO 11
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 11
cgagccgttt cctgtgtgaa atcataaaca tccctgccct gc                42

<210> SEQ ID NO 12
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 12
tgctgcgtat cacgctgagt ccacggggtc gtagggcgac gtata             45

<210> SEQ ID NO 13
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 13
gtgagctcgg ccagaatgcg gcggcatcag atgcccaatc cg        42

<210> SEQ ID NO 14
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 14
actagctgca ggttccgtag cccggagccc ccgtggcgaa cagga     45

<210> SEQ ID NO 15
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 15
cagcaaaggt atgagccggg tggtctggtc agcaggtctc gt        42

<210> SEQ ID NO 16
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 16
cagcggtcat tgcaggcgct tgtcggtggt gccatacgat gc        42

<210> SEQ ID NO 17
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 17
ggctggtgta gaacgtcagc gggccagagc acatcgcgga tctcac    46

<210> SEQ ID NO 18
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 18
ccgggcgaag aatgccaacg ggcaaacgcg gtccggggcg gtattt    46

<210> SEQ ID NO 19
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 19
acctcgcact gggttacggt gctgaactca caacgcgcgc ga        42

<210> SEQ ID NO 20
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 20
tcctggtgct cactgtttac actgatagct ggaagcatgt tt                      42

<210> SEQ ID NO 21
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 21
cgctggcgct catttccgtg ggttttccct tcgcttgcc                          39

<210> SEQ ID NO 22
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 22
tgattgctaa aaaagccatg tgctttcatc aggcttcgc                          39

<210> SEQ ID NO 23
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 23
agcagttttt tttccaaccg ccggttgctc gttaacgggc cggggg                  46

<210> SEQ ID NO 24
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 24
aaaaaaaaag ttaacccacg cgcggggtgc cggtgctgcg cggctc                  46

<210> SEQ ID NO 25
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 25
ggaattaagt cgaaaggggc gcatgggata gattgtaaga agattcaat               49

<210> SEQ ID NO 26
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 26
gtgtaaaacg aagggcgaca gtatcgtcgg atgttaaaca tatgtagag             49

<210> SEQ ID NO 27
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 27
tcgacgggaa aggcaaaggc accgtagcca gaataataa gagaacatt             49

<210> SEQ ID NO 28
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 28
cgccaggtga agggatagct caaacttaaa tttctagcc                       39

<210> SEQ ID NO 29
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 29
gtgccaatta ccagtcccgg atgtgtacat cgacacgttc cgcagc               46

<210> SEQ ID NO 30
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 30
agtaaacggc ttaaaattca gaaatagctg aaaagattta aa                   42

<210> SEQ ID NO 31
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 31
actaaatgtg aaccaattcg taaagatcta cccctcatat ta                   42

<210> SEQ ID NO 32
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 32
gctttccgcg ccattcgcca tgaggtgg                                   28

<210> SEQ ID NO 33

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 33
ccgtaatcgt aaccgtgcat cattacgcca gctggtgggt aa                              42

<210> SEQ ID NO 34
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 34
tgggaacttg agggacgac gatcggtgcg ggcctcagtc ac                               42

<210> SEQ ID NO 35
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 35
aacaacccgg cctcaggaag agcgcaactg ttgggacggc ca                              42

<210> SEQ ID NO 36
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 36
acggtaaagg aacgccatca actttcatca acattccagc ca                              42

<210> SEQ ID NO 37
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 37
atgccggacc ccggttgata atcgcattaa attttttctc cg                              42

<210> SEQ ID NO 38
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 38
taagcaacaa aagggtgaga aatattcaac cgttcagccc ca                              42

<210> SEQ ID NO 39
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 39
```
gccaaaggtg gcatcaaaca tgtttttaaat acctttaa                                  38

<210> SEQ ID NO 40
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 40
caaaaacata ttttaaatgc aagctatttt tgagaactag ca                              42

<210> SEQ ID NO 41
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 41
tgaaataacc tgtttagtca ttccatataa cccagacc                                   38

<210> SEQ ID NO 42
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 42
atactttaaa aatttttaga aaaaggctat caggttcgat ga                              42

<210> SEQ ID NO 43
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 43
gtagcattga atataatgct gaagaggtca ttttagaaa ac                               42

<210> SEQ ID NO 44
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 44
tgatcagagc ataaagcagt aatgtgtagg ttaaatta                                   38

<210> SEQ ID NO 45
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 45
ggggcgcaaa gtacggtgtc tacaggtcag gattactgac ta                              42

<210> SEQ ID NO 46
<211> LENGTH: 42
<212> TYPE: DNA

```
<213> ORGANISM: Artificial Sequence
<220> FEATURE:
<223> OTHER INFORMATION: Synthetic Polynucleotide

<400> SEQUENCE: 46
tttcgcatcc caattctgcg ataattcgag cttcaattaa ga                             42

<210> SEQ ID NO 47
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 47
ttgctccatc aaaaatcagg taatactgcg gaatcatgca ga                             42

<210> SEQ ID NO 48
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 48
ggaagcaaaa gcggattgca tccagagggg gtaatgagca ac                             42

<210> SEQ ID NO 49
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 49
ttgcaaaaag aagcgaaagt tgataatggt cccctgta                                  38

<210> SEQ ID NO 50
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 50
accacataac attattacag gcaaatcaac gtaactcaag ag                             42

<210> SEQ ID NO 51
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 51
ctagtcataa accataattt tgattagctc attctactgc aaaat                          45

<210> SEQ ID NO 52
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 52
tacataaaat aaaacgaact actcattcag tgaatgcata gg                             42
```

<210> SEQ ID NO 53
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 53
acgaggcttg ggaagaaaaa tgccctgacg agaaatgaac gg                    42

<210> SEQ ID NO 54
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 54
taaagtaaaa cagaagcaac tccaggaagt tctatattgt tgtac                 45

<210> SEQ ID NO 55
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 55
actatcactc attataccag tacgagtagt aaattccaac tt                    42

<210> SEQ ID NO 56
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 56
cagacgatta tgcgatttta aagatggttt aatttatcat aa                    42

<210> SEQ ID NO 57
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 57
aaagcgagag cgaaagacgc gtttacgagt agaccattga agcct                 45

<210> SEQ ID NO 58
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 58
gttcgccaaa agcgtcccctt taccgagagt atgcaactga gc                   42

<210> SEQ ID NO 59
<211> LENGTH: 46
<212> TYPE: DNA
<213> ORGANISM: Artificial Sequence
<220> FEATURE:

<223> OTHER INFORMATION: Synthetic Polynucleotide

<400> SEQUENCE: 59
taatcttccc agcgattata cagaggcaaa agaatataac cgcaat            46

<210> SEQ ID NO 60
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 60
ctggctggaa acaaagtaca aaaggcacca acctatgag                    39

<210> SEQ ID NO 61
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 61
tgtacagttg tatcatcgcc taaaatacgt aatgcggccg ctaggt            46

<210> SEQ ID NO 62
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 62
tgaaagatgt gtcgaaatcc gggaagtttc cattaaccc                    39

<210> SEQ ID NO 63
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 63
gggaaccctc catgttactt aggactaaag actttcatcg gaaaaa            46

<210> SEQ ID NO 64
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 64
tgacgacctg gaactgaggg cttggaactg gtaaccctag tt                42

<210> SEQ ID NO 65
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 65
cggtcgcaaa cgaacaagcg caccttcaaa agctgacgga actcaa            46

<210> SEQ ID NO 66
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 66
gcttgatacc tgctaaatag cgtagtttag tggataagta ct                          42

<210> SEQ ID NO 67
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 67
agttaaacac tacgcggaga taccaggcaa ggcttctac                              39

<210> SEQ ID NO 68
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 68
gatcgtcaac gggtgataaa tggacagaca ccagacagga cgatag                      46

<210> SEQ ID NO 69
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 69
tcacggttta aggaacaaaa ctaccaccct cagagaaggt gc                          42

<210> SEQ ID NO 70
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 70
tagcaacgct tgagccgga aacggtcaca actttaatta cccgat                       46

<210> SEQ ID NO 71
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 71
gactgaattt tgtcgtcgtg tatcttgata tgcttttgac cgttcacca                   49

<210> SEQ ID NO 72
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 72
gaattcagcg tccacagaac cgccgggttt tgggtcagat cctcactca        49

<210> SEQ ID NO 73
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 73
ggagaataat actgagtcat tttcttaaga ggcccctag gcaggacca          49

<210> SEQ ID NO 74
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 74
gaattgcgcc tttaattgta tgcagcgaaa gacagttca                    39

<210> SEQ ID NO 75
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 75
tcatagtcaa ctttcaacag ttttcttaaa cagcttgcag gg                42

<210> SEQ ID NO 76
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 76
gagagggacc gtactcagga gacgatctaa agttttctgt at                42

<210> SEQ ID NO 77
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 77
attagcgacc ctcagaaccg caacgcctgt agcatgagtg ag                42

<210> SEQ ID NO 78
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 78
ctcctcaaga gccaccaccc tttcgtcacc agtacactaa ag                42

<210> SEQ ID NO 79
<211> LENGTH: 42

<210> SEQ ID NO 79
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 79
gaaagtaagg gatagcaagc cccatgtacc gtaacaattt tt     42

<210> SEQ ID NO 80
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 80
ggtgaaagcg gcctcccccc ccttccattt ggggaggg     38

<210> SEQ ID NO 81
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 81
tttaacggct cagtaccagg caccgccacc ctcagacagc cc     42

<210> SEQ ID NO 82
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 82
ccgttgatat gccaccacgt cagataccat tttaccag     38

<210> SEQ ID NO 83
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 83
agccgcctca gacgattggc ctataaacag ttaatgctga ga     42

<210> SEQ ID NO 84
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 84
gtcatagtca gagccgccac cttaaagcca gaatgaataa gt     42

<210> SEQ ID NO 85
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 85
acttgagatt agcgtttgcc accaccaccg gaacccagtc tc        42

<210> SEQ ID NO 86
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 86
gcaccatctg tagcgcgttt tccgccaccc tcagatcaca aa        42

<210> SEQ ID NO 87
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 87
ccatcgagta atcagtagcg accaccacca gagccttgac ag        42

<210> SEQ ID NO 88
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 88
tattcattaa taacggaata cccgaacaaa gttactcaaa aa        42

<210> SEQ ID NO 89
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 89
aaggtaaaac tggcatgatt attaagaaaa gtaagtttac ag        42

<210> SEQ ID NO 90
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 90
attcaactta ttacgcagta tgctatctta ccgaaaaaca gg        42

<210> SEQ ID NO 91
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 91
cgccaaaaac gtagaaaata cagaaacaat gaaatgggag aa        42

<210> SEQ ID NO 92
<211> LENGTH: 38
<212> TYPE: DNA
<213> ORGANISM: Artificial Sequence

```
<220> FEATURE:
<223> OTHER INFORMATION: Synthetic Polynucleotide

<400> SEQUENCE: 92
ggtagcaagg ccggaaaaag tttgccttta gccctcag                               38

<210> SEQ ID NO 93
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 93
aaaattcaag gtggcaacat attaagccca ataattgaac aa                          42

<210> SEQ ID NO 94
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 94
tttagactcc cgattgagga attagagcca gattttcg                               38

<210> SEQ ID NO 95
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 95
agagaataaa ataaacagcc acaaatcaga tatagaacca ag                          42

<210> SEQ ID NO 96
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 96
ttaactgaac gctaacgagc gaggcgtttt agcgaataat cg                          42

<210> SEQ ID NO 97
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 97
cgcccaaaga acaagcaagc cagagaatat aaagtcatgt aa                          42

<210> SEQ ID NO 98
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 98
aagtattatt agcagcccag atagccaaaa gatattgagt caccg                       45
```

<210> SEQ ID NO 99
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 99
attctaatca ttccaagaac gagacgacga caatacagta gg                              42

<210> SEQ ID NO 100
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 100
gcgtctttcc attagacagc aatagttagc agacaaaaac cagta                           45

<210> SEQ ID NO 101
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 101
gggaggtcga gcatgtagaa agcctgttta tcaacatgcg tt                              42

<210> SEQ ID NO 102
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 102
aagcagctac gggtaataat tgagtaaaag agtcacaaaa tgaaa                           45

<210> SEQ ID NO 103
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 103
taccgcaaaa ggtaaagtaa tcgccatatt taacatagtt aa                              42

<210> SEQ ID NO 104
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 104
gctgtcttgt tcagctaatg ccagtataaa gccaaaccga cc                              42

<210> SEQ ID NO 105
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 105
tcaacctccc tcttaccaac acccaagagc aatacataat at                              42

<210> SEQ ID NO 106
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 106
tttaggcaaa acttttttcaa atgctgatgc aaatcatta                                 39

<210> SEQ ID NO 107
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 107
aattctgtcc ggtattaaag gcttcagtta caacataagc cc                              42

<210> SEQ ID NO 108
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 108
gcttaatcta aatttaatgg ttttaacctc cggctgagtg aaagca                          46

<210> SEQ ID NO 109
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 109
atacaaagcg ttaaataaga aaatagtgaa tttattttc cctaca                           46

<210> SEQ ID NO 110
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 110
tttcatcggt tatataacta tagtacataa acatcttgc                                  39

<210> SEQ ID NO 111
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 111
gtgtgatata ggtctgagag ataaatcgat tattcgttt                                  39

<210> SEQ ID NO 112

<210> SEQ ID NO 112
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 112
cctaattaca aacctactac ttcttaatag aaaatatccg aa             42

<210> SEQ ID NO 113
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 113
tggaaacatg taaatatatt tacgccaaac cgacactcat cgtagc         46

<210> SEQ ID NO 114
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 114
gcttctgcta cctttgaaa tcgctcaaaa caacattcct tagaac          46

<210> SEQ ID NO 115
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 115
taattaacaa aatcaaataa gttcttacag aacgcccaa                 39

<210> SEQ ID NO 116
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 116
ccttgaaaag agtctaaaca cgtatcataa tagattaatt tatttg         46

<210> SEQ ID NO 117
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 117
atgaaacaaa tcaatatatg ttaggttgtt ctgactgag                 39

<210> SEQ ID NO 118
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 118
aaaagaaatt gatgatgaga agtattggca agaaccacct ga                              42

<210> SEQ ID NO 119
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 119
aaacagtaac ccaccagatc ctttgctgaa cttaacacag ta                              42

<210> SEQ ID NO 120
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 120
acgtaatcct agataatgga attgtcgcca tacgtggctg gt                              42

<210> SEQ ID NO 121
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 121
aactcatcat caattcgcct caatacagag ggccaacaga aa                              42

<210> SEQ ID NO 122
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 122
agatcatttt aattttaaaa aatcccacgc tagattcatc tg                              42

<210> SEQ ID NO 123
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 123
ggaattagtc agatgaatat atcgcgcaga ggcgatcgct at                              42

<210> SEQ ID NO 124
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 124
aggatttgca attcatcaat ataaaacaga aataagaaga tg                              42

<210> SEQ ID NO 125
<211> LENGTH: 42
<212> TYPE: DNA

<210> SEQ ID NO 126
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 125
ttatctatta gagccgtcaa tgattgtttg gattacatat ca        42

<210> SEQ ID NO 126
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 126
tggtcagtta gactttacaa aattcctgat tatcagcgta ga        42

<210> SEQ ID NO 127
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 127
tcaccttgcc cgaacgttat tgcggaacaa agaaaagtac ct        42

<210> SEQ ID NO 128
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 128
ctgtgaatgg aactcaaata acatgcgctt aatgcgcc        38

<210> SEQ ID NO 129
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 129
gtcagtactc aaatatcaaa cacaactcgt attaaaagga gc        42

<210> SEQ ID NO 130
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 130
taagaattaa aaataccgaa catcaacagt tgaaacatt tg        42

<210> SEQ ID NO 131
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 131
ccttaccgcc tcacgcagac gagcctggca agtgtagcaa atcaa        45

<210> SEQ ID NO 132
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 132
atactacatt tttttatgga gctaagaaag gaagggaacg gaacc                           45

<210> SEQ ID NO 133
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 133
gaggccagct catggaaata caaagggaca ttctgtgagg cg                              42

<210> SEQ ID NO 134
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 134
gctacagttc tttgattagt aactatcggc cttgcacaga ca                              42

<210> SEQ ID NO 135
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 135
ttgctttaat taaccgttgt aatccagaac aatatgaaag cg                              42

<210> SEQ ID NO 136
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 136
acgtgctaaa gagtctgtcc aagccattgc aacaggagat ag                              42

<210> SEQ ID NO 137
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 137
ggccgataat cctgagaagt gttgacgctc aatcgccagt ca                              42

<210> SEQ ID NO 138
<211> LENGTH: 21
<212> TYPE: DNA
<213> ORGANISM: Artificial Sequence
<220> FEATURE:

<223> OTHER INFORMATION: Synthetic Polynucleotide

<400> SEQUENCE: 138
ccgagctcga attcgtaatc a                                          21

<210> SEQ ID NO 139
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 139
ggccctgttt tcaccagtga gcaacata                                   28

<210> SEQ ID NO 140
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 140
aaaacagacg ttaatatttt gggattga                                   28

<210> SEQ ID NO 141
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 141
atgaggccgg agaattaaat agta                                       24

<210> SEQ ID NO 142
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 142
gagaatgata ttcattgaat ctaggaat                                   28

<210> SEQ ID NO 143
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 143
gggatttgat agttgcgccg aatatatt                                   28

<210> SEQ ID NO 144
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 144
tgaatttatg atacaggagt gtgccgtc                                   28

-continued

```
<210> SEQ ID NO 145
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 145
gagtcttttc tatcacccgg aaat                                            24

<210> SEQ ID NO 146
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 146
tgaaaattat cccaatccaa aattaccg                                        28

<210> SEQ ID NO 147
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 147
aaattataag aaaacaaaat tttttaa                                         28

<210> SEQ ID NO 148
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 148
atattttata gccctaaaac aaggaagg                                        28

<210> SEQ ID NO 149
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 149
aatgcaatac ggcgcgtctg cgcg                                            24

<210> SEQ ID NO 150
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 150
ggccctgttt tcaccagtga gcaacatatt cctctaccac ctacatcac                 49

<210> SEQ ID NO 151
<211> LENGTH: 49
<212> TYPE: DNA
<213> ORGANISM: Artificial Sequence
<220> FEATURE:
<223> OTHER INFORMATION: Synthetic Polynucleotide
```

-continued

<400> SEQUENCE: 151
aaaacagacg ttaatatttt gggattgatt cctctaccac ctacatcac        49

<210> SEQ ID NO 152
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 152
atgaggccgg agaattaaat agtattcctc taccacctac atcac        45

<210> SEQ ID NO 153
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 153
gagaatgata ttcattgaat ctaggaattt cctctaccac ctacatcac        49

<210> SEQ ID NO 154
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 154
gggatttgat agttgcgccg aatatatttt cctctaccac ctacatcac        49

<210> SEQ ID NO 155
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 155
tgaatttatg atacaggagt gtgccgtctt cctctaccac ctacatcac        49

<210> SEQ ID NO 156
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 156
gagtcttttc tatcacccgg aaatttcctc taccacctac atcac        45

<210> SEQ ID NO 157
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 157
tgaaaattat cccaatccaa aattaccgtt cctctaccac ctacatcac        49

<210> SEQ ID NO 158
<211> LENGTH: 49

```
<212> TYPE: DNA
<213> ORGANISM: Artificial Sequence
<220> FEATURE:
<223> OTHER INFORMATION: Synthetic Polynucleotide

<400> SEQUENCE: 158
aaattataag aaaacaaaat tttttaatt cctctaccac ctacatcac        49

<210> SEQ ID NO 159
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 159
atattttata gccctaaaac aaggaaggtt cctctaccac ctacatcac        49

<210> SEQ ID NO 160
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 160
aatgcaatac ggcgcgtctg cgcgttcctc taccacctac atcac            45

<210> SEQ ID NO 161
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 161
caaaatcaaa cctgtcgtgc cgcccgct                               28

<210> SEQ ID NO 162
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 162
agccgccgcg aaacgtacag catcccgt                               28

<210> SEQ ID NO 163
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 163
gcccaaggat tgcgggaaga taca                                   24

<210> SEQ ID NO 164
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 164
```
ggaagccgct tttgcaaaag acgtttac                                              28

<210> SEQ ID NO 165
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 165
tcacgttaaa aaaaggctc cacgaggg                                               28

<210> SEQ ID NO 166
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 166
gaggttggcc tatttcggaa cgaaacat                                              28

<210> SEQ ID NO 167
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 167
gaacagaatc cgtcacctca atag                                                  24

<210> SEQ ID NO 168
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 168
agtcagaaat tttatcctga agacttgc                                              28

<210> SEQ ID NO 169
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 169
tttacatttt gaataccaag tttagaat                                              28

<210> SEQ ID NO 170
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 170
cacgacccgc ctgcaacagt gtaaagca                                              28

<210> SEQ ID NO 171
<211> LENGTH: 24
<212> TYPE: DNA
<213> ORGANISM: Artificial Sequence

```
<220> FEATURE:
<223> OTHER INFORMATION: Synthetic Polynucleotide

<400> SEQUENCE: 171
aaaacgccag taaaggggga aagc                                          24

<210> SEQ ID NO 172
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 172
caaaatcaaa cctgtcgtgc cgcccgctta tcttcctcac actcccaaa               49

<210> SEQ ID NO 173
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 173
agccgccgcg aaacgtacag catcccgtta tcttcctcac actcccaaa               49

<210> SEQ ID NO 174
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 174
gcccaaggat tgcgggaaga tacatatctt cctcacactc ccaaa                   45

<210> SEQ ID NO 175
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 175
ggaagccgct tttgcaaaag acgtttacta tcttcctcac actcccaaa               49

<210> SEQ ID NO 176
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 176
tcacgttaaa aaaaggctc cacgagggta tcttcctcac actcccaaa                49

<210> SEQ ID NO 177
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 177
gaggttggcc tatttcggaa cgaaacatta tcttcctcac actcccaaa               49
```

<210> SEQ ID NO 178
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 178
gaacagaatc cgtcacctca atagtatctt cctcacactc ccaaa                45

<210> SEQ ID NO 179
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 179
agtcagaaat tttatcctga agacttgcta tcttcctcac actcccaaa            49

<210> SEQ ID NO 180
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 180
tttacatttt gaataccaag tttagaatta tcttcctcac actcccaaa            49

<210> SEQ ID NO 181
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 181
cacgacccgc ctgcaacagt gtaaagcata tcttcctcac actcccaaa            49

<210> SEQ ID NO 182
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 182
aaaacgccag taaggggga aagctatctt cctcacactc ccaaa                 45

<210> SEQ ID NO 183
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 183
ccagcagggg gagaggcggt tctaatga                                   28

<210> SEQ ID NO 184
<211> LENGTH: 28
<212> TYPE: DNA
<213> ORGANISM: Artificial Sequence
<220> FEATURE:
<223> OTHER INFORMATION: Synthetic Polynucleotide

```
<400> SEQUENCE: 184
gacgttgaga gatagacttt ctgccgcc                                              28

<210> SEQ ID NO 185
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 185
tgtcaattca gctcattttt tagcgagt                                              28

<210> SEQ ID NO 186
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 186
ggtatgcctg taaatcgttc attt                                                  24

<210> SEQ ID NO 187
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 187
ttatagttgt ttagactgga taggaatt                                              28

<210> SEQ ID NO 188
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 188
aatagaatca gcttgctttc gtttgcgg                                              28

<210> SEQ ID NO 189
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 189
caaataatgc cttgagtaac agattagg                                              28

<210> SEQ ID NO 190
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 190
gaacatcggc caaaatcggg cgac                                                  24

<210> SEQ ID NO 191
```

```
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 191
gaagcgcaga gcctaatttg catccggt                                          28

<210> SEQ ID NO 192
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 192
ttttcagatt tcaattacct gtaacctt                                          28

<210> SEQ ID NO 193
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 193
aacccttcag cagaagataa acaatatc                                          28

<210> SEQ ID NO 194
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 194
aacccgagta ttcctcgaaa ggag                                              24

<210> SEQ ID NO 195
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 195
ccagcagggg gagaggcggt tctaatgata acattcctaa cttctcata                   49

<210> SEQ ID NO 196
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 196
gacgttgaga gatagacttt ctgccgccta acattcctaa cttctcata                   49

<210> SEQ ID NO 197
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 197
```

```
tgtcaattca gctcattttt tagcgagtta acattcctaa cttctcata          49
```

<210> SEQ ID NO 198
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 198

```
ggtatgcctg taaatcgttc attttaacat tcctaacttc tcata              45
```

<210> SEQ ID NO 199
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 199

```
ttatagttgt ttagactgga taggaattta acattcctaa cttctcata          49
```

<210> SEQ ID NO 200
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 200

```
aatagaatca gcttgctttc gtttgcggta acattcctaa cttctcata          49
```

<210> SEQ ID NO 201
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 201

```
caaataatgc cttgagtaac agattaggta acattcctaa cttctcata          49
```

<210> SEQ ID NO 202
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 202

```
gaacatcggc caaaatcggg cgactaacat tcctaacttc tcata              45
```

<210> SEQ ID NO 203
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 203

```
gaagcgcaga gcctaatttg catccggtta acattcctaa cttctcata          49
```

<210> SEQ ID NO 204
<211> LENGTH: 49
<212> TYPE: DNA

```
<213> ORGANISM: Artificial Sequence
<220> FEATURE:
<223> OTHER INFORMATION: Synthetic Polynucleotide

<400> SEQUENCE: 204
ttttcagatt tcaattacct gtaaccttta acattcctaa cttctcata                49

<210> SEQ ID NO 205
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 205
aacccttcag cagaagataa acaatatcta acattcctaa cttctcata                49

<210> SEQ ID NO 206
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 206
aacccgagta ttcctcgaaa ggagtaacat tcctaacttc tcata                    45

<210> SEQ ID NO 207
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 207
acatcgtgaa tacattagcg accagag                                        27

<210> SEQ ID NO 208
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 208
ttagaaggtc aataccgaac acttttta                                       28

<210> SEQ ID NO 209
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 209
ccgtactagt atagcctaaa ttatgtaa                                       28

<210> SEQ ID NO 210
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 210
cgacgttttt tgcaatgttt agaagagaa                                      29
```

<210> SEQ ID NO 211
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 211
cgagcatccc gtcgggagtt aggcgcata                                        29

<210> SEQ ID NO 212
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 212
ccatatgcac tccaactaaa aaattgggct tgag                                  34

<210> SEQ ID NO 213
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 213
gcgtgccatt aaaggccgtt catattacgg taatc                                 35

<210> SEQ ID NO 214
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 214
aggtgagtta acactaacgt catagcagcc tttac                                 35

<210> SEQ ID NO 215
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 215
agccagcaaa tctaaacagg ggacgggaga attaa                                 35

<210> SEQ ID NO 216
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 216
gttatcttag gagcaataag aatgaaatag caata                                 35

<210> SEQ ID NO 217
<211> LENGTH: 35
<212> TYPE: DNA
<213> ORGANISM: Artificial Sequence
<220> FEATURE:

<223> OTHER INFORMATION: Synthetic Polynucleotide

<400> SEQUENCE: 217
aaaagcctga gcaatacctt tccaccctca gagcc					35

<210> SEQ ID NO 218
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 218
cgccatgttt accaaacata gatcaaaagc gtcat					35

<210> SEQ ID NO 219
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 219
aaacgtatgc aaatatttca tgttaaataa cactg					35

<210> SEQ ID NO 220
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 220
acgccgaata aacaaattct tgtaacgaat tttgc					35

<210> SEQ ID NO 221
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 221
tttgagggga cgacaacaag atgccctgaa ccgat					35

<210> SEQ ID NO 222
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 222
tcggctaatt ctgtatcaac agcttgctca acaac					35

<210> SEQ ID NO 223
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 223
gcgaggtttt tgttaaatca gattgtatcg cctgt					35

```
<210> SEQ ID NO 224
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 224
gacaccacgg aataacatac aacaaagatg aggat                          35

<210> SEQ ID NO 225
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 225
tccaacaggt ctgaagccag ttttgatcag aatga                          35

<210> SEQ ID NO 226
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 226
aaaaccagga ttagcggggt taagtattat cggcg                          35

<210> SEQ ID NO 227
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 227
aaagagctcc tgtacgtggg acacatccta attta                          35

<210> SEQ ID NO 228
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 228
gcagtgttca atcaaaggct aaattgagcg atgccg                         36

<210> SEQ ID NO 229
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 229
aacaattctc gtcaaaaccg atcaaagggc cttacc                         36

<210> SEQ ID NO 230
<211> LENGTH: 36
<212> TYPE: DNA
<213> ORGANISM: Artificial Sequence
<220> FEATURE:
<223> OTHER INFORMATION: Synthetic Polynucleotide
```

<400> SEQUENCE: 230
atcatagcat cagcagtttg aaccctgtga ctcctt                              36

<210> SEQ ID NO 231
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 231
cagtagtgcc ggacaaacag atctactagg aaggta                              36

<210> SEQ ID NO 232
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 232
cccttagacg cagatgccgc cgaagcccct tcaaag                              36

<210> SEQ ID NO 233
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 233
gagagatcgg aaaactgact aaagattaag ccgttc                              36

<210> SEQ ID NO 234
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 234
ggtgcgggcc tcttaacgct caatctacca gtttca                              36

<210> SEQ ID NO 235
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 235
ataatcgatc gagagggatc gaggctttga gtgtac                              36

<210> SEQ ID NO 236
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 236
gataggtaca aacgccggat atcatcaaga gtaatct                             37

<210> SEQ ID NO 237
<211> LENGTH: 40

<210> SEQ ID NO 237
<211> LENGTH: (not shown)
<212> TYPE: DNA
<213> ORGANISM: Artificial Sequence
<220> FEATURE:
<223> OTHER INFORMATION: Synthetic Polynucleotide

<400> SEQUENCE: 237
agtcataagt tgccacatta ttcatcagtt gagttatacc                                40

<210> SEQ ID NO 238
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 238
tcttcgcctc ctctcaaaaa ctggcctaga cggtggaacc g                              41

<210> SEQ ID NO 239
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 239
ccctcacttt accagagaat ccttgaagtc ccggcctcac c                              41

<210> SEQ ID NO 240
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 240
cgcctgtgca ctcttgaacc tgagagtccc ctgaacaaag tc                             42

<210> SEQ ID NO 241
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 241
aatcaacagt tgaacatccc taagaattag aaaggccgga ga                             42

<210> SEQ ID NO 242
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 242
cggtagcgca ctcagccatc cacccaacga atgcactggt ct                             42

<210> SEQ ID NO 243
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 243
cttctgagag gtgttatggt taaaacatta aagaaacgca aa                              42

<210> SEQ ID NO 244
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 244
cggcctttag tgattccggc aataagagct gaatatacccc tc                             42

<210> SEQ ID NO 245
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 245
gctcattaac agcggctctc aagactttag ccgccgccag tg                              42

<210> SEQ ID NO 246
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 246
tgagaaggaa taaccttgct tttttaatct cattaaggca gg                              42

<210> SEQ ID NO 247
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 247
ccaatcgcaa gacaggaaac aaagaggcta aacagttcag aa                              42

<210> SEQ ID NO 248
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 248
atgctgacct ttttattctg agcccgtata aacagagtgc ct                              42

<210> SEQ ID NO 249
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 249
tgggaagttc gccaagtcag gattttaaga actggtgtga at                              42

<210> SEQ ID NO 250
<211> LENGTH: 42
<212> TYPE: DNA
<213> ORGANISM: Artificial Sequence

```
<220> FEATURE:
<223> OTHER INFORMATION: Synthetic Polynucleotide

<400> SEQUENCE: 250
gcaaagccac cgcttacctt aaatttcaac tttaacaaag ct                              42

<210> SEQ ID NO 251
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 251
cgtgcatttg gtgtgctcat tttacccaaa tcaacacaag aa                              42

<210> SEQ ID NO 252
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 252
tcattccatt aaacgaaaga ccgagggtag caacgcatga gg                              42

<210> SEQ ID NO 253
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 253
ttcatcaacc aaccgaaaga ggacagatga acggggccac ta                              42

<210> SEQ ID NO 254
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 254
ctattttgca ccatttgcgg gtgtatcacc cccagcgatt at                              42

<210> SEQ ID NO 255
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 255
aacccactac actgttcttt gcgacaactt ttaaaggggt ca                              42

<210> SEQ ID NO 256
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 256
atcaccatca atataatgcc ttagaaccct ttacctttat tt                              42
```

<210> SEQ ID NO 257
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 257
gagtaatgtg taggcagtca agagagatag agggttcagg tc                    42

<210> SEQ ID NO 258
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 258
taaagatgga acgtgatta aaatactttg taccatacca gc                     42

<210> SEQ ID NO 259
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 259
caaaagaact ggcacaataa ttaaaggtgt gtgttgttgg ca                    42

<210> SEQ ID NO 260
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 260
agagcatggg caaaaattac gaataaatat tttcagctgg tc                    42

<210> SEQ ID NO 261
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 261
caatagagac ggaacgactt gagccaataa taaaggatta ta                    42

<210> SEQ ID NO 262
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 262
actgtagcgc gttttagcac ccaataaccg tcagatgaat at                    42

<210> SEQ ID NO 263
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 263
ccaccacacc acccgtagga ttagagagaa gaagacaaaa tc                          42

<210> SEQ ID NO 264
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 264
agaaccgaat tgctagaccg gtctctgaat ttaagagcag tt                          42

<210> SEQ ID NO 265
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 265
gatacaggag tgtaataaat cggaaacatt tcatttgaat ta                          42

<210> SEQ ID NO 266
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 266
aacgagtaac atgattgctc atacagacga cgatattagt ta                          42

<210> SEQ ID NO 267
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 267
ttacagggaa gaaaaacagt agggctcagg cgatcaggcg at                          42

<210> SEQ ID NO 268
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 268
gtagcattcc acagttttgt catatgcgga ggcattttcg ag                          42

<210> SEQ ID NO 269
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 269
aaacggcacc agtacgccaa catgtaataa ggtaataatt tt                          42

<210> SEQ ID NO 270

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 270
tcggtttata gaacgagtag tggaattgct ttcaagttaa ta        42

<210> SEQ ID NO 271
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 271
cactaaaaca ctcacgaagg cacattaaat gtgaacaaat ca        42

<210> SEQ ID NO 272
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 272
tctttgatcg cctgataaat tgcgaaccga tatagccgag ct        42

<210> SEQ ID NO 273
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 273
atcaaaatgg cttagataac tattaatggc gaccgttaca aac        43

<210> SEQ ID NO 274
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 274
aagaacgcga gaaaaacgac gacgggaagg atagcttgaa tcc        43

<210> SEQ ID NO 275
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 275
tcccgacttt gttaaaattc gaattgtacg aactgaacga acc        43

<210> SEQ ID NO 276
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 276

```
attcgcctga acaaaattaa caagtacata tgtgagtagt caa              43
```

<210> SEQ ID NO 277
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 277

```
accagctgct gcgaataaga gcaaacaaga gaatattgcc tcaaatat          48
```

<210> SEQ ID NO 278
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 278

```
gagaggttga gagctagcat tgtaccccgg ttgcttcacg gatccagc          48
```

<210> SEQ ID NO 279
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 279

```
gaagccaagt taccagtatg ggcaacatat aatggtaaca tctttaca          48
```

<210> SEQ ID NO 280
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 280

```
attacgcaga aggtatagat tagagcctat tagatatcat taattatc          48
```

<210> SEQ ID NO 281
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 281

```
atcggtttgc gggttattaa tcgtattaaa tccttaatgg gaacggaa          48
```

<210> SEQ ID NO 282
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 282

```
aatattaaat tcaccattcc tgattatttg tttgaaattg cacagtaa          48
```

<210> SEQ ID NO 283
<211> LENGTH: 48
<212> TYPE: DNA

```
<213> ORGANISM: Artificial Sequence
<220> FEATURE:
<223> OTHER INFORMATION: Synthetic Polynucleotide

<400> SEQUENCE: 283
cgaacccctt tgaaatttc aattaccgca caggggggcgg ttaattttt          48

<210> SEQ ID NO 284
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 284
cagtaaatca ggtaatgctt tgagactcct cactcggata aaatttgt            48

<210> SEQ ID NO 285
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 285
ggattaaaat agcgcaacac ccaccaccct cattttcaga cgaggcat            48

<210> SEQ ID NO 286
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 286 cggataaacct attaacctcc cataggtctg agagaagacg ctgagtaa           48

<210> SEQ ID NO 287
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 287
gcggagtgag acgacgttgg tagaaagcag gatagcaagc ctgctgca            48

<210> SEQ ID NO 288
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 288
agaccaaagg ccgcacgcat acgagaaaca cccaatagat accaatca            48

<210> SEQ ID NO 289
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 289
cgaattctaa tgcgaacgtt agagcctaat ttgcccaatc cagccagaa          49
```

<210> SEQ ID NO 290
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 290
cgtggcattt tgaatatcct gacgctaacg agcgttttg ttcgcctgc                49

<210> SEQ ID NO 291
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 291
aacagggaga agattagtct taaagcgtta gcaaggcaag ccacgtaat                 49

<210> SEQ ID NO 292
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 292
caaaccccac tgcgtgcggc gaataccgat agcccccggg taaaggctt                 49

<210> SEQ ID NO 293
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 293
tgccctgcgg catcttacct gcagccatct ggtcacagca aaaatatca                 49

<210> SEQ ID NO 294
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 294
ggagcggttg cggataaagg tttagcaaac gtagacagat aggataata                 49

<210> SEQ ID NO 295
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 295
acggctgata atgggcacgt attgtagaat cctcagcgca gaggaagtt                 49

<210> SEQ ID NO 296
<211> LENGTH: 49
<212> TYPE: DNA
<213> ORGANISM: Artificial Sequence
<220> FEATURE:

<223> OTHER INFORMATION: Synthetic Polynucleotide

<400> SEQUENCE: 296
gtagattccg tcacattatt cattaaagta ttttgtggca ataccagaa        49

<210> SEQ ID NO 297
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 297
ggcagcccgg tccgtgcaac tgctgtagct caacattaat tggtcattt        49

<210> SEQ ID NO 298
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 298
taacggaaac gtcagtggca tcatttggga attagttagc aagcgtcag        49

<210> SEQ ID NO 299
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 299
acaaacaaca ggagtcagag ccgccaccca ccggatttgc cattcggtc        49

<210> SEQ ID NO 300
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 300
taggcattat acaccggaat ataaggcctt ctgacccgga agtaccagg        49

<210> SEQ ID NO 301
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 301
gagaatactc caaacaaaag gagccttttg aatttgaacg cgttccttta        49

<210> SEQ ID NO 302
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 302
attctcaaca gttgaggatc ctaaaacata agcaaaaata aacagataa        49

```
<210> SEQ ID NO 303
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 303
tcagaaaaca ggaagctcat ttaggaactc catgtgaacg aggcggcaa        49

<210> SEQ ID NO 304
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 304
gtaaaaatct acaatagcgg tgccggttca gacgtcatac cgccagcac        49

<210> SEQ ID NO 305
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 305
cgatgaattt atccagttac aatatttaca ttaaacgttt tagtgtcga        49

<210> SEQ ID NO 306
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 306
agagagaaac gattctttcc aatcagctac aattttggct ataaaacag        49

<210> SEQ ID NO 307
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 307
gcccaatact aacaactaaa aaggaattac cttgcgttgc cacgctgag        49

<210> SEQ ID NO 308
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 308
gctattggag ttaactgaac atggaataac ataaaaagca tcgaggaag        49

<210> SEQ ID NO 309
<211> LENGTH: 48
<212> TYPE: DNA
<213> ORGANISM: Artificial Sequence
<220> FEATURE:
<223> OTHER INFORMATION: Synthetic Polynucleotide
```

<400> SEQUENCE: 309
tttaaatgcg atattcgctg ataaattact tcgttaacgg ctggtttg        48

<210> SEQ ID NO 310
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 310
accgattgcc aaagccagct tttgcaggcg ctttcccgaa cgagaagcc       49

<210> SEQ ID NO 311
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 311
gagggagata gtagtgaaaa gccaatgaac agaatcaatt ctgcgaacg       49

<210> SEQ ID NO 312
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 312
agcattatta tttaagggtt agaacctcac gcaaacaaaa gaaagctaa       49

<210> SEQ ID NO 313
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 313
aaaatcaatt atcattcagg tcaatataat cctgacagat gatcacaat       49

<210> SEQ ID NO 314
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 314
aaccatcaga gcacacgtca gcgtggtgta tcaaaaacat ccacattca       49

<210> SEQ ID NO 315
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 315
gcaaaactta gtttgaccat tttaaatatt ttttcttgcc gtgaagggt       49

<210> SEQ ID NO 316
<211> LENGTH: 49

```
<212> TYPE: DNA
<213> ORGANISM: Artificial Sequence
<220> FEATURE:
<223> OTHER INFORMATION: Synthetic Polynucleotide

<400> SEQUENCE: 316
tagcccccac agttgattcc caagtttgcc tttaggccgg aacccttttt          49

<210> SEQ ID NO 317
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 317
ggtgtctggc gaattattcc gtccggccga tagcatttgg ggcgcgagc           49

<210> SEQ ID NO 318
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 318
gcctccctca gagccgccaa taaagtacag tagatcgtaa tcagtagcg           49

<210> SEQ ID NO 319
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 319
cggaacctca ttccatatat tcaagttatg atgaaccaaa tcccgtaaa           49

<210> SEQ ID NO 320
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 320
tcaaaataga accacgccgc cattggccca aacaactggt aacggggtc           49

<210> SEQ ID NO 321
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 321
attcgaggaa agaccatcaa attatagtat attcagtcca attagtaaa           49

<210> SEQ ID NO 322
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 322
```
tcagacgagc attgtcaaga aattgcttgg agaaaattac caagccagc         49

<210> SEQ ID NO 323
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 323
acatggcaat ggaaatcgac ataaaattct gtaaattaga ttactacag          49

<210> SEQ ID NO 324
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 324
ccataacgat agctcgtcgc tattaattgt gtacagcgca gaagcaaac          49

<210> SEQ ID NO 325
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 325
ttaatgcttt cggaagtgcc gtgatataca ggaggccacc ctcagaacc          49

<210> SEQ ID NO 326
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 326
aaagaaggaa ttactaatgc agatacatag gaataggtaa cgcaactgt          49

<210> SEQ ID NO 327
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 327
agtaagagag aggcgtaaac tttttcaagg ggatgcaata ggaacatta          49

<210> SEQ ID NO 328
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 328
tttacggtca gaaccgccac cgtaccgtaa agctggcgaa agatatatt          49

<210> SEQ ID NO 329
<211> LENGTH: 49
<212> TYPE: DNA
<213> ORGANISM: Artificial Sequence

```
<220> FEATURE:
<223> OTHER INFORMATION: Synthetic Polynucleotide

<400> SEQUENCE: 329
tcaccaggtg ataacataat tactagaata gtatcgtctt tctaaatga                49

<210> SEQ ID NO 330
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 330
tcatagttaa actaacggaa caacccatct cagagtatca taaccctcg                49

<210> SEQ ID NO 331
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 331
taaacaacga ataaagctca ggaagatctt aacaataaag cccgctatt                49

<210> SEQ ID NO 332
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 332
attttcttga aaattaaagt aacgacaata aacaataatg cacttaaac                49

<210> SEQ ID NO 333
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 333
ttcacgtgta tgggtctaaa gacagcccag tttcggccac cctgtatca                49

<210> SEQ ID NO 334
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 334
aaggctaaaa taatatcccg ctgccagttt ccgggctaat tgagaatcg                49

<210> SEQ ID NO 335
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 335
atattcggtc gccacagtga aatggttttg atagaaagga acagccagc                49
```

<210> SEQ ID NO 336
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 336
catcgccctt ttgcacagcg agtaacaagt agaaaagtcc tggacagta                49

<210> SEQ ID NO 337
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 337
tgcgccgcag cagccaagta cttttcatat taccggaagc ctttagttg                49

<210> SEQ ID NO 338
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 338
ggctggcaac ttttaaaacg aagaataaat ccgcgacctg cgcaagaac                49

<210> SEQ ID NO 339
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 339
aactgacctg accttttgag gcttgcagga ttctcgccag ctatccggt                49

<210> SEQ ID NO 340
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 340
actaaagact ttttgctaca gtcaccctac aatgattcga ggaattgta                49

<210> SEQ ID NO 341
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 341
gtaaaatgtt tttacgcact cgctgtctcc tgtttccaga cgccgacaa                49

<210> SEQ ID NO 342
<211> LENGTH: 49
<212> TYPE: DNA
<213> ORGANISM: Artificial Sequence
<220> FEATURE:
<223> OTHER INFORMATION: Synthetic Polynucleotide

```
<400> SEQUENCE: 342
taaacggacc aagcgtacaa cggagattag gttttcgccc aaaagaata                49
```